US012161659B2

(12) United States Patent
Lu et al.

(10) Patent No.: US 12,161,659 B2
(45) **Date of Patent: *Dec. 10, 2024**

(54) COMPOSITIONS AND METHODS FOR THE DELIVERY OF NUCLEIC ACIDS

(71) Applicant: CASE WESTERN RESERVE UNIVERSITY, Cleveland, OH (US)

(72) Inventors: Zheng-Rong Lu, Cleveland, OH (US); Anthony Malamas, Cleveland, OH (US); Maneesh Gujrati, Cleveland, OH (US); Da Sun, Cleveland, OH (US)

(73) Assignee: CASE WESTERN RESERVE UNIVERSITY, Cleveland, OH (US)

(*) Notice: Subject to any disclaimer, the term of this patent is extended or adjusted under 35 U.S.C. 154(b) by 419 days.

This patent is subject to a terminal disclaimer.

(21) Appl. No.: 17/487,562

(22) Filed: Sep. 28, 2021

(65) Prior Publication Data

US 2022/0226362 A1 Jul. 21, 2022

Related U.S. Application Data

(63) Continuation of application No. 14/743,298, filed on Jun. 18, 2015, now Pat. No. 11,129,845.

(60) Provisional application No. 62/090,687, filed on Dec. 11, 2014, provisional application No. 62/013,961, filed on Jun. 18, 2014.

(51) Int. Cl.

| | |
|---|---|
| ***A61K 31/713*** | (2006.01) |
| ***A61K 47/00*** | (2006.01) |
| ***A61K 48/00*** | (2006.01) |
| ***C07K 5/062*** | (2006.01) |
| ***C12N 15/11*** | (2006.01) |
| *C12N 15/113* | (2010.01) |

(52) U.S. Cl.

CPC ........ *A61K 31/713* (2013.01); *A61K 48/0033* (2013.01); *C07K 5/0606* (2013.01); *C12N 15/111* (2013.01); *C12N 15/113* (2013.01); *C12N 2310/14* (2013.01); *C12N 2320/31* (2013.01); *C12N 2320/32* (2013.01)

(58) Field of Classification Search

None

See application file for complete search history.

(56) References Cited

U.S. PATENT DOCUMENTS

| | | | |
|---|---|---|---|
| 5,622,718 | A | 4/1997 | Al-Shamkhani et al. |
| 5,700,848 | A | 12/1997 | Soon-Shiong et al. |
| 6,472,506 | B1 | 10/2002 | Moreau et al. |
| 2001/0003598 | A1 | 6/2001 | Cherian et al. |
| 2003/0161791 | A1 | 8/2003 | Bentley et al. |
| 2004/0028745 | A1 | 2/2004 | Bouhadir et al. |
| 2005/0271705 | A1 | 12/2005 | Hughes et al. |
| 2008/0221208 | A1 | 9/2008 | Palczewski et al. |
| 2011/0288170 | A1 | 11/2011 | Palczewski et al. |

FOREIGN PATENT DOCUMENTS

| | | | |
|---|---|---|---|
| CN | 101745119 | A | 6/2010 |
| GB | 1334980 | A | 10/1973 |
| WO | 2008/042686 | A3 | 10/2008 |

OTHER PUBLICATIONS

Malamas et al.; "Design and evaluation of new pH-sensitive amphiphilic cationic lipids for siRNA delivery"; Journal of Controlled Release; online Jun. 21, 2013, 171:296-307; https://doi.org/10.1016/j.jconrel.2013.06.019.

Samuel Zalipsky, et al.; "Peptide attachment to extremities of liposomal surface grafted PEG chains: preparation of the long-circulating form of laminin pentapeptide, YIGSR"; Bioconjugate Chemistry 1995 6 (6), 705-708 DOI: 10.1021/bc00036a008 Zalipsky et al., Bioconj. chem., 1995, 6:705-708.

Xu, Rongzuo; "Design, Synthesis and Evaluation of Innovative Carriers for Delivery of MR Contrast Agents nd Nucleic Acids"; Dissertation Dec. 2019.

Sun, Da, et al.; "Synthesis and Evaluation of PH-Sensitive Multifunctional Lipids for Efficient Delivery of CRISPR/CAS9 in Gene Editing"; Bioconjugate Chem. 2019, 30, 667-678.

Wang, et al., "A Multifunctional and Reversibly Polymerizable Carrier for Efficient siRNA delivery"; ScienceDirect; Biomaterials vol. 29, Issue 1, Jan. 2008, pp. 15-22; https://doi.org/10.1016/j.biomaterials.2007.08.048.

(Continued)

*Primary Examiner* — Ileana Popa

(74) *Attorney, Agent, or Firm* — Tarolli, Sundheim, Covell & Tummino LLP

(57) ABSTRACT

A compound comprising formula (I):

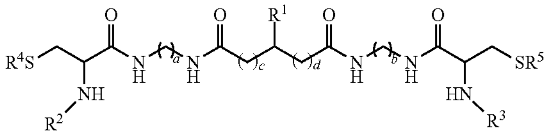

wherein $R^1$ is an alkylamino group or a group containing at least one aromatic group;

$R^2$ and $R^3$ are independently an aliphatic group or hydrophobic group;

$R^4$ and $R^5$ are independently H, a substituted or unsubstituted alkyl group, an alkenyl group, an acyl group, an aromatic group, polymer, a targeting group, or a detectable moiety;

a, b, c, and d are independently an integer from 1 to 10; and pharmaceutically acceptable salts thereof.

21 Claims, 44 Drawing Sheets

Specification includes a Sequence Listing.

(56) References Cited

OTHER PUBLICATIONS

Xu-Li Wang, et al.; "Novel Polymerizable Surfactants with pH-Sensitive Amphiphilicity and Cell Membrane Disruption for Efficient siRNA Delivery"; Bioconjugate Chemistry 2007 18 (6), 2169-2177; DOI: 10.1021/bc700285q.

Xu-Li Wang, et al.; "Targeted Systemic Delivery of a Therapeutic siRNA with a Multifunctional Carrier Controls Tumor Proliferation in Mice"; Molecular Pharmaceutics 2009 6 (3), 738-746; DOI: 10.1021/mp800192d Wang, et al., Mol. Pharm., 2009, 6:738-746.

Kummitha CM, et al.; "Albumin pre-coating enhances intracellular siRNA delivery of multifunctional amphiphile/siRNA nanoparticles"; International Journal Nanomedicine. 2012;7:5205-5214. doi:10.2147/IJN.S34288.

Zonghua Liu, et al.; "Polysaccharides-based Nanoparticles as Drug Delivery Systems"; Advanced Drug Delivery Reviews 60; Sep. 16, 2008; 256 pgs.; www.elsevier.com/locate/addr.

a)

b)

c)

(A)

ECO Cationic Lipid

Mal-PEG (5000)-NHS

RGD Peptide - c(RGDfK)

Mal-PEG (5000)-RED
(RGD-PEG)

(B)

(A)

(B)

A

B

C

D

E

A

B

C

COMPOSITIONS AND METHODS FOR THE DELIVERY OF NUCLEIC ACIDS

RELATED APPLICATION

This application claims priority from U.S. Provisional Application Nos. 62/013,961, filed Jun. 18, 2014, and 62/090,687, filed Dec. 11, 2014, the subject matter of which are incorporated herein by reference in their entirety.

GOVERNMENT FUNDING

This invention was made with government support under EB000489 awarded by the National Institutes of Health. The government has certain rights in the invention.

BACKGROUND

RNA interference (RNAi) is a natural antisense mechanism that cells possess to regulate the expression of genes at the mRNA level. This process relies on the ability of short fragments (19-23 nucleotides in length) of double stranded small interfering RNA (siRNA) to recognize and guide complementary mRNA transcripts into the RNA-induced silencing complex (RISC). Once translocated into the RISC complexes, the mRNA transcripts are cleaved and ultimately degraded inside the cell, rendering them ineffective for translation into proteins. Meanwhile, the siRNAs are preserved and constantly recycled for further silencing events. The ability to synthetically design siRNAs against particular mRNA sequences has triggered numerous clinical and preclinical studies to tailor RNAi induced silencing against a variety of disease-related genetic transcripts.

Delivery of siRNA with nanoparticles is desirable in order to overcome their susceptibility to serum nucleases and their ability to stimulate the innate immune system upon intravenous injection. The use of nanoparticles can also prevent the possibility of off-target side effects. Nanoparticles are also required for successful siRNA therapies because they can facilitate intracellular release following uptake by tumor cells. Endocytosis has been identified as a dominant cellular uptake mechanism, whereby foreign material delivered to cells will be sequestered into endosomal compartments and ultimately degraded after fusion with lysosomes. As a result, siRNA therapy faces an additional delivery barrier because access to the RISC complexes in the cytoplasm is necessary for effective treatment. Viral vectors have evolved for millions of years to become efficient carriers at introducing their genetic material into host cells. As a result, adenoviruses and retroviruses are currently explored as possible gene therapy vectors, but the success they have shown in vivo is masked by their potential to severely trigger the immune response. Compared to viral vectors, non-viral or synthetic vectors have many advantages, such as low immunogenicity, low production cost, and ease of modification, thus making them very attractive for siRNA delivery platforms. However, much research is still required in order to improve upon the low transfection efficiencies of most current non-viral vectors.

Cationic lipid constructs are widely used as alternatives to viral nanoparticles. They form nanoparticles through the electrostatic interaction with the negatively-charged siRNA. Such nanoparticles, or lipoplexes, can be designed to exhibit similar characteristics and behaviors to those observed with viral vectors by utilizing pH sensitive moieties that facilitate endosomal escape. This is typically accomplished by incorporating an amine-rich head group with an overall slightly acidic pKa into the cationic lipid structure. Once they become protonated in the acidic endosomal-lysosomal compartments, cationic lipoplexes are able to participate in membrane fusion and degradation events by inducing an electrostatic flip-flop reorganization of anionic phospholipids in the membrane bilayer. This extensive transfer of lipids neutralizes the charge interactions that govern particle formation, causing the inevitable dissociation of siRNA from the lipoplexes, followed by and subsequent release into the cytoplasm.

SUMMARY

Embodiments described herein relate to compounds used to form multifunctional pH-sensitive carriers that are designed to condense nucleic acids and deliver the condensed nucleic acids to cells. The compounds can include a protonable amino head group, which can complex with nucleic acids, fatty acid or lipid tails, which can participate in hydrophobic condensation, and two cystenyl residues capable of forming disulfide bridges via autooxidation.

In some embodiments, the compound includes formula (I):

(I)

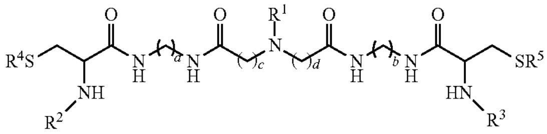

wherein $R^1$ is an alkylamino group or a group containing at least one aromatic group; $R^2$ and $R^3$ are independently an aliphatic group or a hydrophobic group derived, for example, from a fatty acid; $R^4$ and $R^5$ are independently H, a substituted or unsubstituted alkyl group, an alkenyl group, an acyl group, an aromatic group, polymer, a targeting group, or a detectable moiety; a, b, c, and d are independently an integer from 1 to 10 (e.g., a, b, c, and d are each 2); and pharmaceutically acceptable salts thereof.

In some embodiments, $R^1$ can include at least one of:

$-(CH_2)_eNR^6R^7$;

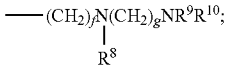

or

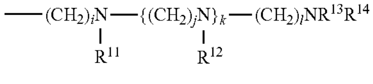

where $R^6$, $R^7$, $R^8$, $R^9$, $R^{10}$, $R^{11}$, $R^{12}$, $R^{13}$, and $R^{14}$ are independently hydrogen, an alkyl group, a hydrophobic group, or a nitrogen containing substituent; and e, f, g, i, j, k, and 1, are an integer from 1 to 10. For example, $R^1$ can include at least one of $CH_2CH_2NH_2$, $CH_2CH_2NHCH_2CH_2NHCH_2CH_2NH$, or $CH_2CH_2NHCH_2CH_2CH_2CH_2NHCH_2CH_2CH_2NH$.

In other embodiments, $R^2$ and $R^3$ are independently a hydrophobic group derived from oleic acid or linoleic acid and are the same or different.

In some embodiments, $R^4$ and $R^5$ are independently H, a substituted or unsubstituted polymer, a targeting group, or a detectable moiety.

In some embodiments, the compound can have the formulas:

(ECO)

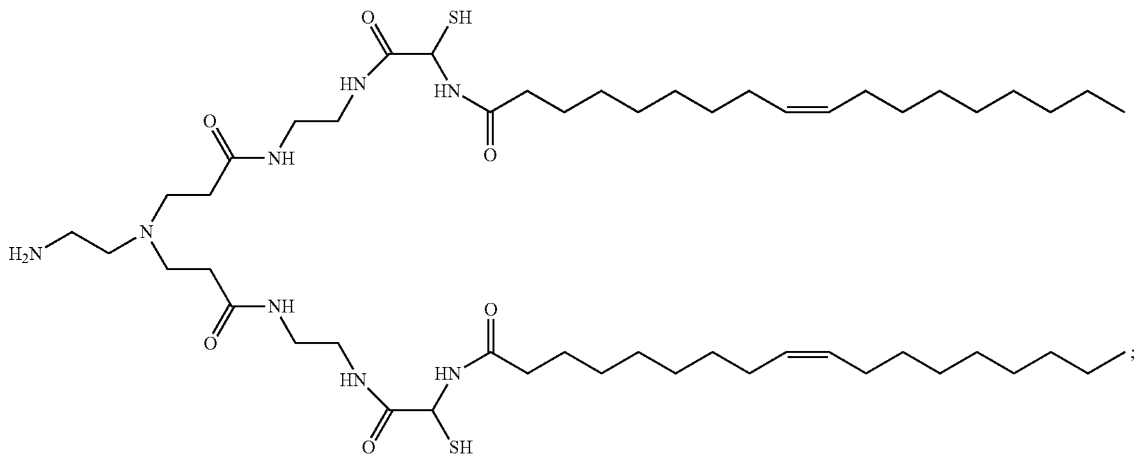

(ECL)

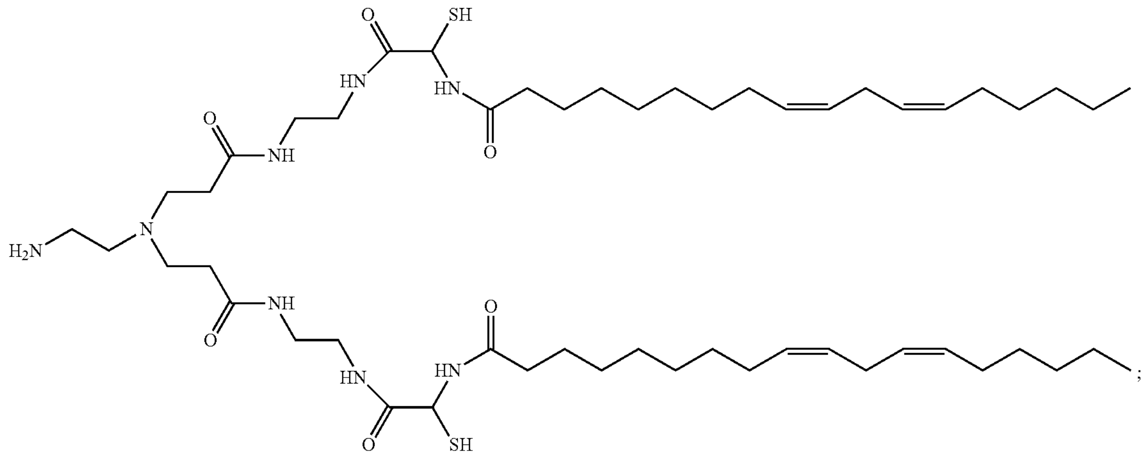

or pharmaceutically acceptable salts thereof.

In other embodiments, a targeting group can be covalently attached to the compound by a linker. The targeting group can be a peptide, a protein, an antibody, or an antibody fragment. The linker can include a polyamino acid group, a polyalkylene group, or a polyethyelene glycol group. The linker can also include an acid labide bond that is hydrolyzable in an endolyssomal environment following uptake to cells, such as cancer cells.

E) Quantification of whole body tumors from D. (data represents mean±SE, n=5, *p≤0.05).

FIGS. 37(A-C) illustrate plots showing zeta potential of A) ECO/siRNA, B) PEG-ECO/siRNA, and C) PEG(HZ)-ECO/siRNA nanoparticles incubated in PBS solutions at pH levels corresponding to stages of intracellular trafficking (pHs 7.4, 6.5, 5.4).

Figure 38:
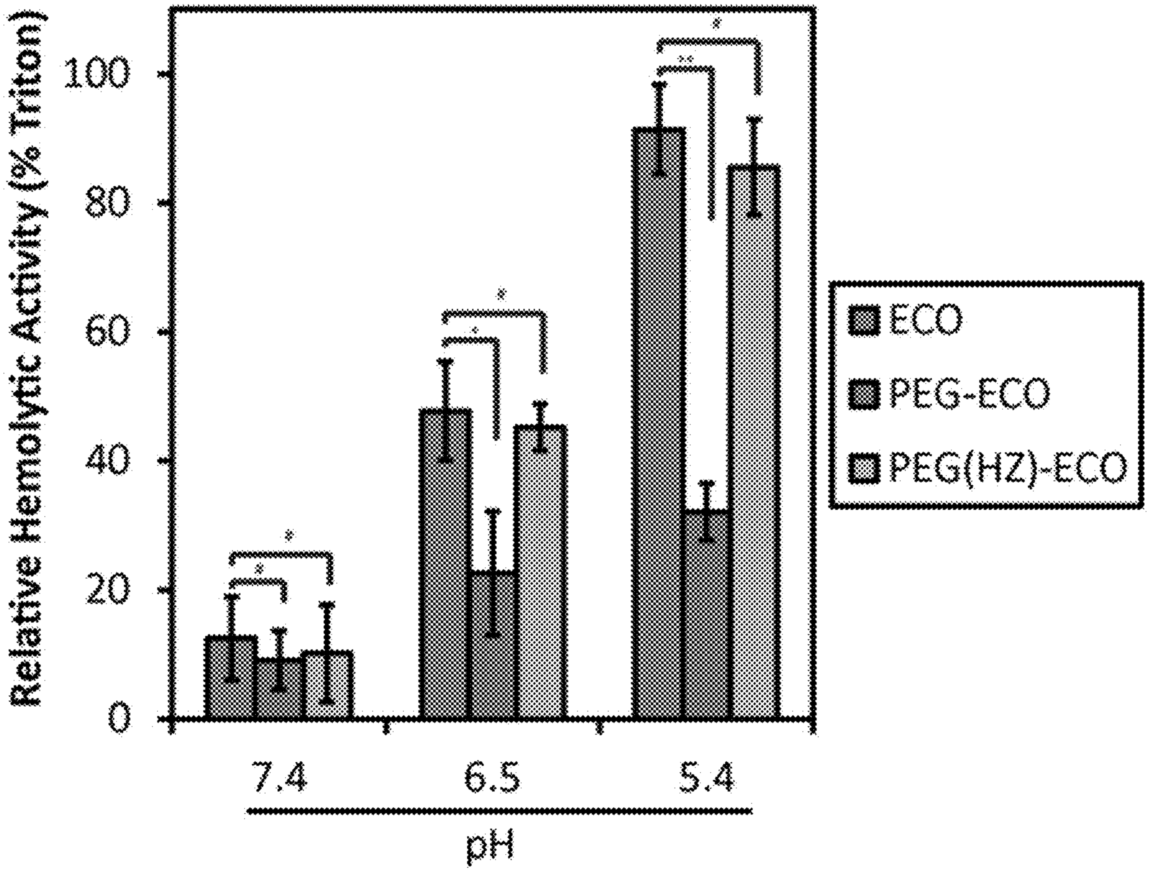

FIG. 38 illustrates a plot showing the comparison of hemolytic activity of ECO, PEG-ECO, and PEG(HZ)-ECO siRNA nanoparticles at pH levels corresponding to stages of intracellular trafficking. Relative hemolytic activity was calculated with respect to the hemolytic activity of 1% Triton-X-100.

FIGS. 39(A-C) illustrate a graph, plot, and image showing A) Cellular uptake of unmodified, PEG-, PEG(HZ)-, RGD-PEG-, and RGD-PEG(HZ)-modified ECO/siRNA nanoparticles quantified with flow cytometry using an AF647-labeled siRNA. B) Luciferase silencing of unmodified, PEG-, PEG(HZ)-, RGD-PEG-, and RGD-PEG(HZ)-modified ECO/siRNA nanoparticles in MDA-MB-231-luc triple-negative breast cancer cells. C) Confocal microscopy images of MDA-MB-231 cells incubated with RGD-PEG-, and RGD-PEG(HZ)-modified ECO/siRNA nanoparticles at 10 min, 3 hr, and 6 hr. DAPI, cell nucleus (blue); Lysotracker DND-26, lysosomes (green); siRNA, AF-647 (red).

FIGS. 40(A-D) illustrate in vivo luciferase silencing efficiency following a single i.v. treatment with various surface-modified ECO/siRNA nanoparticles (1.0 mg/kg siRNA dose). A) Quantification of bioluminescence signal from ROIs drawn over the tumor. B) Representative BLI images of the different treatment groups. Tumor accumulation and retention of surface-modified ECO/siRNA nanoparticles following i.v. administration. C) Representative FMT images of a single mouse from each treatment group over 24 hours post-treatment with nanoparticles formulated with an AF647-tagged siRNA. An ROI was drawn over the area containing the tumor. D) Quantification of fluorescence signal from each ROI. Flow cytometry and confocal microscopy analysis of single cell suspensions obtained from primary MDA-MB-231 mammary fat pad tumors following i.v. administration of various surface modified ECO/siRNA nanoparticles.

Figure 41A:
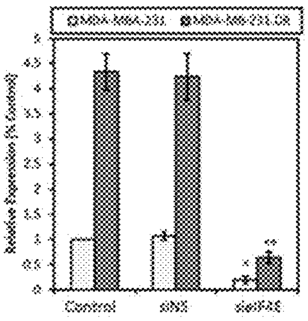
Figure 41B:
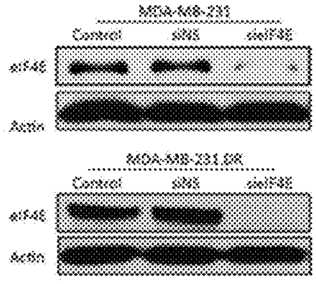

FIGS. 41(A-C) illustrate evaluation of eIF4E mRNA and protein expression as determined by A) qRT-PCR and B) western blot analysis in MDA-MB-231 and MDA-MB-231.DR cells 5 days following treatment with RGD-PEG(HZ)-ECO/siRNA nanoparticles (N/P=8) delivering either sieIF4E or siNS (100 nM). C) Dose-response curves as determined by MTT assay of MDA-MB-231 and MDA-MB-231.DR cells treated with varying concentrations of PTX following prior treatment with RGD-PEG(HZ)-ECO/siRNA nanoparticles delivering sieIF4E or siNS. Cells were first treated with RGD-PEG(HZ)-ECO/siRNA nanoparticles for 48 hours followed by treatment with varying concentrations of PTX for an additional 48 hours.

FIGS. 42(A-F) illustrate in vivo efficacy of combination therapy involving PTX and RGD-PEG(HZ)-ECO/sieIF4E nanoparticles. Alternating treatment of siRNA nanoparticles and PTX every 6 days began after 4 weeks once the primary tumors reach an average of 150 $mm^3$. A) Quantification of bioluminescent imaging over the course of the experiment (data represents mean±SE, n=5, *p≤0.05, **p≤0.01) and B) BLI images at week 10. C) Tumor growth was monitored using digital caliper measurements (data represents mean±SE, n=5, *p≤0.05, **p≤0.01). D) Primary tumors were resected at week 10 and E) final tumor weights were obtained (data represents mean±SE, n=5, *p≤0.05, **p≤0.01). F) Semi-quantitative real-time quantification of eIF4E mRNA expression from the resected primary tumors (data represents mean±SE, n=5, *p≤0.05, **p≤0.0, #p>0.05).

FIGS. 43(A-D) illustrate images showing immunofluorescent staining of A) eIF4E B) VEGF C) Cyclin D1 and D) survivin from primary tumor samples.

Figure 44A:
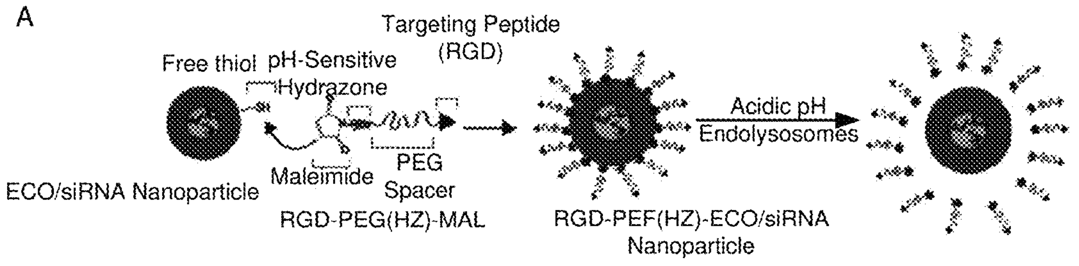
Figure 44B:
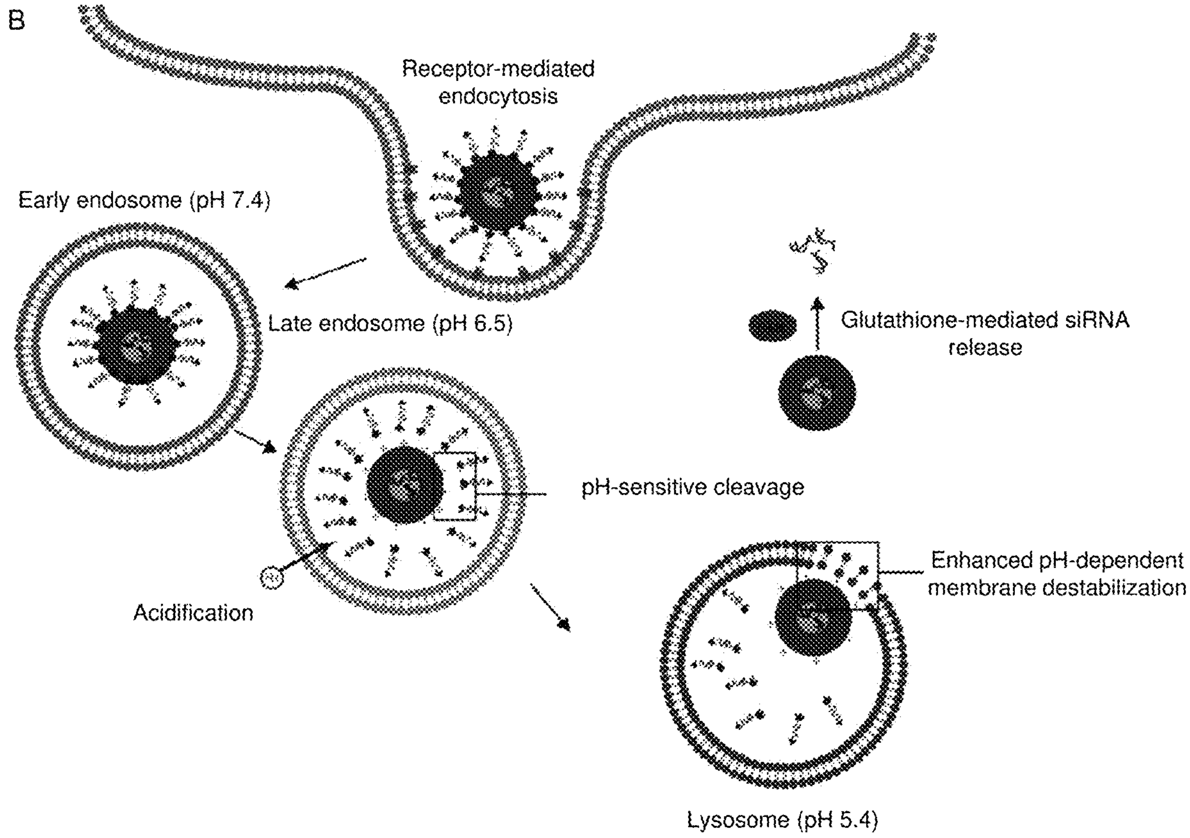

FIGS. 44(A-B) illustrates a schematic drawing showing: A) pH-sensitive surface modification of ECO/siRNA nanoparticles with RGD-PEG(HZ)-maleimide. B) RGD-PEG(HZ)-ECO/siRNA nanoparticles facilitate receptor-mediated cellular internalization resulting in trafficking of the nanoparticles into the late endosomes. Within the late endosomes, the increasingly acidic environment cleaves the hydrazone linkage to promote shedding of the PEG layer and expose the core ECO/siRNA nanoparticle. Next, the intrinsic pH-sensitive nature of ECO promotes endosomal escape by enhancing interactions with the anionic charged lipid bilayer of the endolysosomes. Once release into the cytosol, endogenous glutathione (GSH) mediates reduction of disulfide bonds formed within ECO/siRNA nanoparticles to release the siRNA cargo. Upon release, free siRNA is able to initiate RNAi-induced gene silencing.

DETAILED DESCRIPTION

Methods involving conventional molecular biology techniques are described herein. Such techniques are generally known in the art and are described in detail in methodology treatises, such as *Current Protocols in Molecular Biology*, ed. Ausubel et al., Greene Publishing and Wiley-Interscience, New York, 1992 (with periodic updates). Unless otherwise defined, all technical terms used herein have the same meaning as commonly understood by one of ordinary skill in the art to which the present invention pertains. Commonly understood definitions of molecular biology terms can be found in, for example, Rieger et al., *Glossary of Genetics: Classical and Molecular,* 5th Ed., Springer-Verlag: New York, 1991, and Lewin, *Genes V*, Oxford University Press: New York, 1994. The definitions provided herein are to facilitate understanding of certain terms used frequently herein and are not meant to limit the scope of the present invention.

It must be noted that, as used in the specification and the appended claims, the singular forms "a," "an" and "the" include plural referents unless the context clearly dictates otherwise. Thus, for example, reference to "a pharmaceutical carrier" includes mixtures of two or more such carriers, and the like. "Optional" or "optionally" means that the subsequently described event or circumstance can or cannot occur, and that the description includes instances where the event or circumstance occurs and instances where it does not. For example, the phrase "optionally substituted lower alkyl" means that the lower alkyl group can or cannot be substituted and that the description includes both unsubstituted lower alkyl and lower alkyl where there is substitution.

The term "alkenyl group" is defined herein as a $C_2$-$C_{20}$ alkyl group possessing at least one C═C double bond.

The term "alkyl group" as used herein is a branched or unbranched saturated hydrocarbon group of 1 to 25 carbon atoms, such as methyl, ethyl, n-propyl, isopropyl, n-butyl, isobutyl, t-butyl, pentyl, hexyl, heptyl, octyl, decyl, tetradecyl, hexadecyl, eicosyl, tetracosyl and the like. A "lower alkyl" group is an alkyl group containing from one to six carbon atoms.

The term "acyl" group as used herein is represented by the formula C(O)R, where R is an organic group such as, for example, an alkyl or aromatic group as defined herein.

The term "alkylene group" as used herein is a group having two or more $CH_2$ groups linked to one another. The alkylene group can be represented by the formula $(CH_2)_a$, where a is an integer of from 2 to 25.

The term "aromatic group" as used herein is any group containing an aromatic group including, but not limited to, benzene, naphthalene, etc. The term "aromatic" also includes "heteroaryl group," which is defined as an aromatic group that has at least one heteroatom incorporated within the ring of the aromatic group. Examples of heteroatoms include, but are not limited to, nitrogen, oxygen, sulfur, and phosphorus. The aryl group can be substituted or unsubstituted. The aryl group can be substituted with one or more groups including, but not limited to, alkyl, alkynyl, alkenyl, aryl, halide, nitro, amino, ester, ketone, aldehyde, hydroxy, carboxylic acid, or alkoxy.

The terms "cancer" or "tumor" refer to any neoplastic growth in a subject, including an initial tumor and any metastases. The terms "cancer cell" or "tumor cell" can refer to cells that divide at an abnormal (i.e., increased) rate.

The phrase "nitrogen containing substituent" is defined herein as any amino group. The term "amino group" is defined herein as a primary, secondary, or tertiary amino group. In the alternative, the nitrogen containing substituent can be a quaternary ammonium group. The nitrogen containing substituent can be an aromatic or cycloaliphatic group, where the nitrogen atom is either part of the ring or directly or indirectly attached by one or more atoms (i.e., pendant) to the ring. The nitrogen containing substituent can be an alkylamino group having the formula $RNH_2$, where R is a branched or straight alkyl group, and the amino group can be substituted or unsubstituted.

The term "nucleic acid" refers to oligonucleotides, nucleotides, polynucleotides, or to a fragment of any of these, to DNA or RNA (e.g., mRNA, rRNA, tRNA, miRNA, siRNA) of genomic or synthetic origin which may be single-stranded or double-stranded and may represent a sense or antisense strand, to peptide nucleic acids, or to any DNA-like or RNA-like material, natural or synthetic in origin, including, e.g., iRNA, ribonucleoproteins (e.g., iRNPs). The term can also encompass nucleic acids containing known analogues of natural nucleotides, as well as nucleic acid-like structures with synthetic backbones.

The term "subject" can refer to any animal, including, but not limited to, humans and non-human animals (e.g., rodents, arthropods, insects, fish (e.g., zebrafish)), non-human primates, ovines, bovines, ruminants, lagomorphs, porcines, caprines, equines, canines, felines, ayes, etc.), which is to be the recipient of a particular treatment. Typically, the terms "patient" and "subject" are used interchangeably herein in reference to a human subject.

The terms "inhibit," "silencing," and "attenuating" can refer to a measurable reduction in expression of a target mRNA (or the corresponding polypeptide or protein) as compared with the expression of the target mRNA (or the corresponding polypeptide or protein) in the absence of an interfering RNA molecule of the present invention. The reduction in expression of the target mRNA (or the corresponding polypeptide or protein) is commonly referred to as "knock-down" and is reported relative to levels present following administration or expression of a non-targeting control RNA.

Embodiments described herein relate to compounds used to form multifunctional pH-sensitive carriers that are designed to condense nucleic acids and deliver the condensed nucleic acids to cells. The compounds can include a protonable amino head group, fatty acid or lipid tails, and two cysteine residues.

The protonable amino head group can complex with a nucleic acids to form nanoparticles for delivery of nucleic acids to cells. The amines in the head groups contribute to the essential pH-sensitive characteristic of the carrier system, which is important for improving endosomal escape and RNAi-mediated silencing efficiency. Greater protonation of the amino head groups can occur in the relatively acidic environment (pH=5-6) of the endosome and lysosome compartments after cellular uptake. This enhances electrostatic interactions between the cationic carriers and the anionic phospholipids of endosomal/lysosomal membranes, promoting the bilayer destabilization and nanoparticle charge neutralization events required for efficient cytosolic release of their nucleic acid payload. By affecting the number of amines, and thus overall pKa, of the cationic carrier, the choice of head group can ultimately determine the degree to which such protonation can occur. The pH-sensitive property of the carrier system is essential so that the nanoparticles do not affect the integrity of the outer cell membrane and cause cell death, but instead are able to selectively fuse with and destabilize the endosomal and lysosomal membranes.

The cysteine residues can form disulfide bridges via autooxidation and react with functional groups of other compounds, such as those containing thiol groups. Once the nucleic acid is complexed with the compound, the thiol groups can produce disulfide (S—S) bonds or bridges by autooxidation to form oligomers and polymers or crosslinking. The disulfide bonds can stabilize the nanoparticles of the nucleic acid and compound and help achieve release of the nucleic acid once the nanoparticle is in the cell.

For example, when the nucleic acid is siRNA, the cleavage of disulfide bonds in the siRNA delivery systems in reductive cytoplasm can facilitate cytoplasm-specific release of siRNA. The compounds will be stable in the plasma at very low free thiol concentration (e.g., 15 μM). When the de compounds are incorporated into target cells, the high concentration of thiols present in the cell (e.g., cytoplasm) will reduce the disulfide bonds to facilitate the dissociation and release of the nucleic acid.

The disulfide bonds can be readily produced by reacting the same or different compounds before complexation with nucleic acid or during the complexation in the presence of an oxidant. The oxidant can be air, oxygen or other chemical oxidants. Depending upon the dithiol compound selected and oxidative conditions, the degree of disulfide formation can vary in free polymers or in complexes with nucleic acids. Thus, the compounds including two cysteine residues are monomers, and the monomers can be dimerized, oligomerized, or polymerized depending upon the reaction conditions.

The fatty acid or lipid tails groups can participate in hydrophobic condensation and help form compact, stable nanoparticles with the nucleic acids and introduce amphiphilic properties to facilitate pH sensitive escape of nanoparticles from endosomal and lysosomal compartments. This is particularly useful when the compounds are used as in vivo delivery devices.

In general, the transfection efficiency of carriers has been shown to decrease with increasing alkyl chain length and saturation of the lipid tail groups. When saturated, shorter aliphatic chains (C12 and C14) favor higher rates of intermembrane lipid mixing and reportedly allow for better transfection efficiencies in vitro, as compared to in vivo, whereas the opposite is true for longer chains (C16 and C18). Typically, saturated fatty acids greater than 14 carbons in length are not favorable for nucleic acid transfections due to their elevated phase transition temperature and overall less fluidity than those that are unsaturated. However, it has been discovered that there exists a limit, at which point an increase in unsaturation and lipid fluidity is inversely correlated to transfection efficiency, primarily because some degree of rigidity is required for particle stability, as evidenced by the widespread use of cholesterol in lipid nanoparticle formulations.

Advantageously, multifunctional pH-sensitive carriers formed using the compounds have improved stability when administered systemically to a subject, protect condensed nucleic acids from degradation, and promote endosomal escape and cytosolic release upon cellular uptake.

In some embodiments, a targeting group can be attached to the compound by, for example, a thiol group of a cysteine residue. The targeting group can be useful in the delivery of nucleic acids into cells. The targeting group can be a peptide, an antibody, an antibody fragment or one of their derivatives. For example, target-specific peptides can be conjugated directly to the compound or indirectly via a linker (e.g., polyethylene glycol) prior or during the formation of nanoparticles. Depending upon the selection of the targeting group, the targeting group can be covalently bonded to either the thiol group of the cysteine residues.

In one aspect, the targeting group is indirectly attached to the compound by a linker. Examples of linkers include, but are not limited to, a polyamine group, a polyalkylene group, a polyamino acid group or a polyethylene glycol group. The selection of the linker as well as the molecular weight of the linker can vary depending upon the desired properties. In one aspect, the linker is polyethylene glycol having a molecular weight from 500 to 10,000, 500 to 9,000, 500 to 8,000, 500 to 7,000, or 2,000 to 5,000. In certain aspects, the targeting group is first reacted with the linker in a manner such that the targeting group is covalently attached to the linker. For example, the linker can possess one or more groups that can react with an amino group present on a peptide. The linker also possesses additional groups that react with and form covalent bonds with the compounds described herein. For example, the linker can possess maleimide groups that readily react with the thiol groups. The selection of functional groups present on the linker can vary depending upon the functional groups present on the compound. In one aspect, the targeting group is a peptide such as, for example, an RGD peptide or bombesin peptide that is covalently attached to polyethylene glycol.

In some embodiment, the linker can include an acid labide bond, such as formed by incorporation of a hydrazone into the linker that is hydrolyzable in an endolyssomal environment following uptake to cells, such as cancer cells. For example, the linker can be covalently linked to the compound by at least one of a covalent hydrolyzable ester, covalent hydrolyzable amide, covalent photodegradable urethane, covalent hydrolyzable ester, or covalent hydrolyzable acrylate-thiol linkage. Following cellular uptake of the compound, within the late endosomes, the increasingly acidic environment can cleave the acid labile linkage to promote shedding of a polymer linker, such as PEG, and expose the core of the compound/nucleic complex nanoparticle.

In other aspects, it is also desirable to attach the targeting group to a nanoparticle produced by the compounds described herein. For example, after a nanoparticle composed of a nucleic acid has been produced using the compounds and techniques described herein, the targeting group can be attached to the nanoparticle via a linker.

In some embodiments, the compound can include formula (I):

(I)

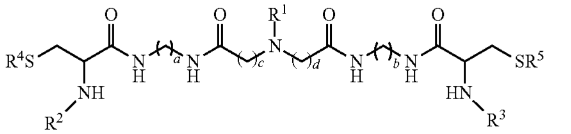

wherein $R^1$ is an alkylamino group or a group containing at least one aromatic group; $R^2$ and $R^3$ are independently an aliphatic group or a hydrophobic group, derived, for example, from a fatty acid;

$R^4$ and $R^5$ are independently H, a substituted or unsubstituted alkyl group, an alkenyl group, an acyl group, an aromatic group, polymer, a targeting group, or a detectable moiety; a, b, c, and d are independently an integer from 1 to 10 (e.g., a, b, c, and d are each 2); and pharmaceutically acceptable salts thereof.

In some embodiments, $R^1$ can include at least one of:

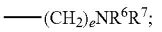

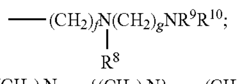 or

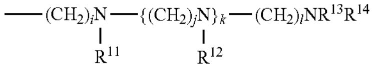

where $R^6$, $R^7$, $R^8$, $R^9$, $R^{10}$, $R^{11}$, $R^{12}$, $R^{13}$, and $R^{14}$ are independently hydrogen, an alkyl group, a hydrophobic group, or a nitrogen containing substituent; and e, f, g, i, j, k, and 1, are an integer from 1 to 10.

For example, $R^1$ can include at least one of $CH_2NH_2$, $CH_2CH_2NH_2$, $CH_2CH_2CH_2NH_2$, $CH_2CH_2CH_2CH_2NH_2$, $CH_2CH_2CH_2CH_2CH_2NH_2$, $CH_2NHCH_2CH_2CH_2NH_2$, $CH_2CH_2NHCH_2CH_2CH_2NH_2$, $CH_2CH_2CH_2NHCH_2CH_2CH_2CH_2NHCH_2CH_2CH_2NH_2$, $CH_2CH_2NHCH_2CH_2CH_2CH_2NH_2$, $CH_2CH_2NHCH_2CH_2CH_2NHCH_2CH_2CH_2HN_2$, or $CH_2CH_2NH(CH_2CH_2NH)_dCH_2CH_2NH_2$, where d is from 0 to 10.

In some embodiments, $R^1$ can be $CH_2CH_2NH_2$ or $CH_2CH_2NHCH_2CH_2CH_2NHCH_2CH_2CH_2HN_2$.

In other embodiments, $R^2$ and $R^3$ are independently an aliphatic group or a hydrophobic group derived from fatty acid, such as oleic acid or linoleic acid, and are the same or different. The additional double bond in linoleic acid introduces an extra kink into the hydrocarbon backbone, giving the compound a broader conical shape than oleic acid and increasing its fluidity. When incorporated into a nanoparticle structure, the extra degree of unsaturation elevates the propensity to form the hexagonal phase during an impending membrane fusion event of cellular uptake.

In some embodiments, $R^4$ and $R^5$ are independently H, a substituted or unsubstituted polymer, a targeting group, or a detectable moiety.

In some embodiments, the compound can have the formulas:

(ECO)

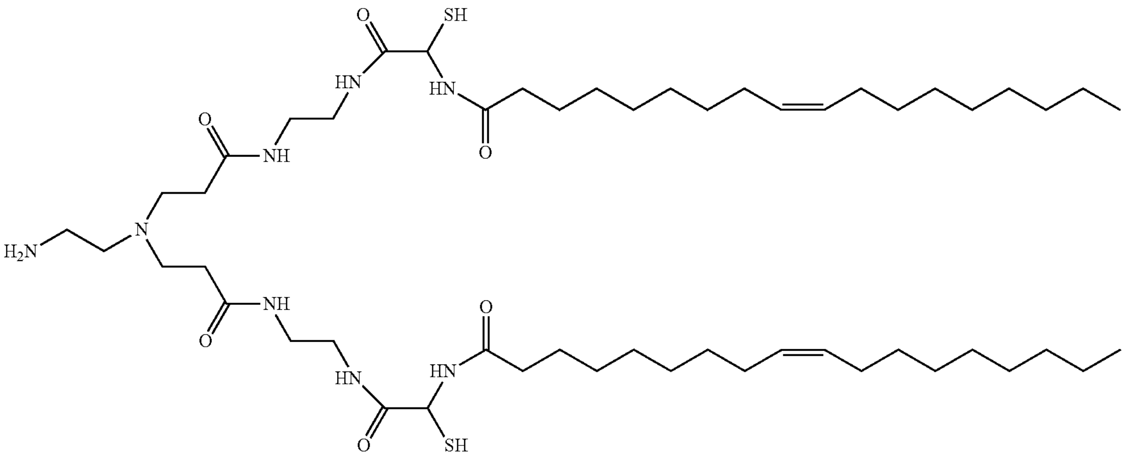

;

(ECL)

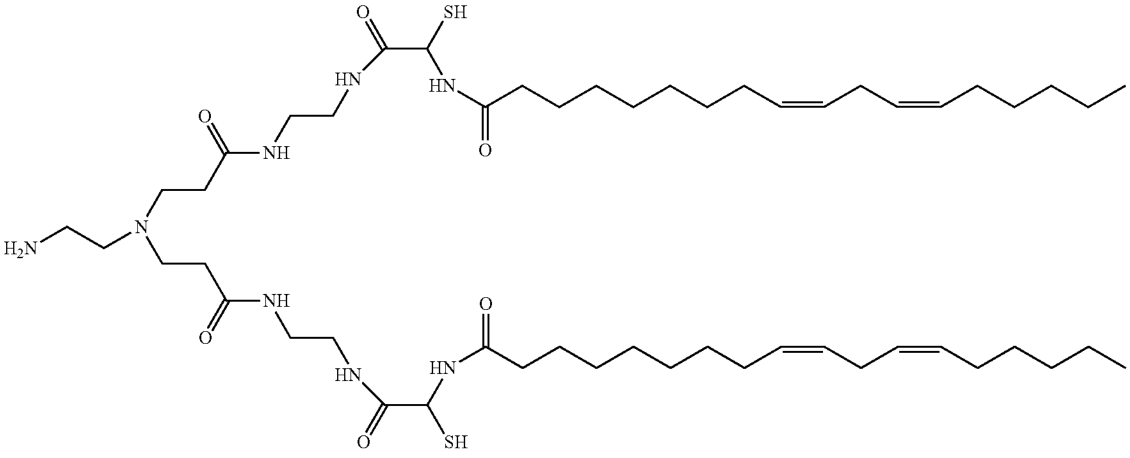

;

or pharmaceutically acceptable salts thereof.

Figure 2:
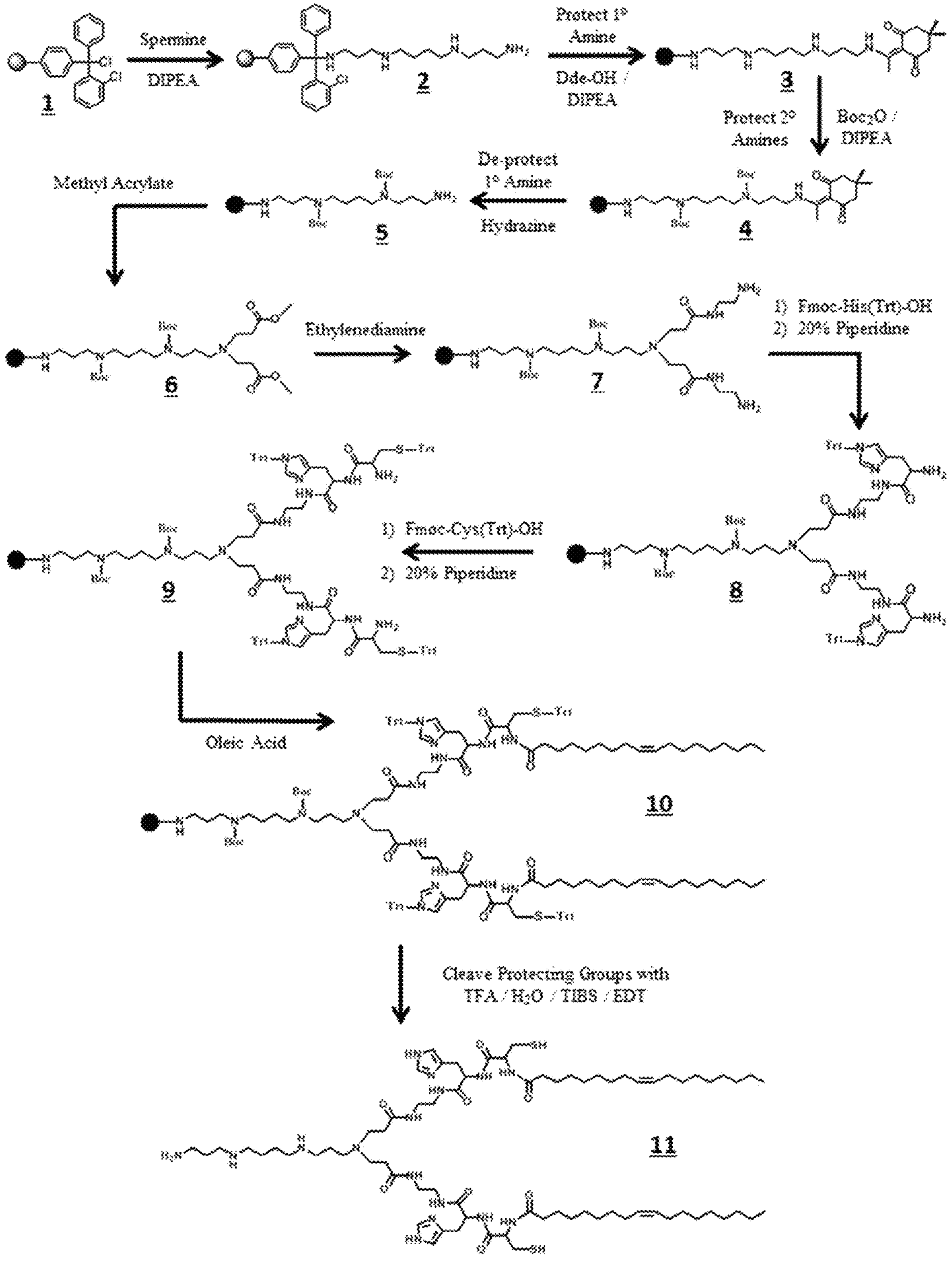
FIG. 2 is a reaction scheme for SHCO.
Figure 24:
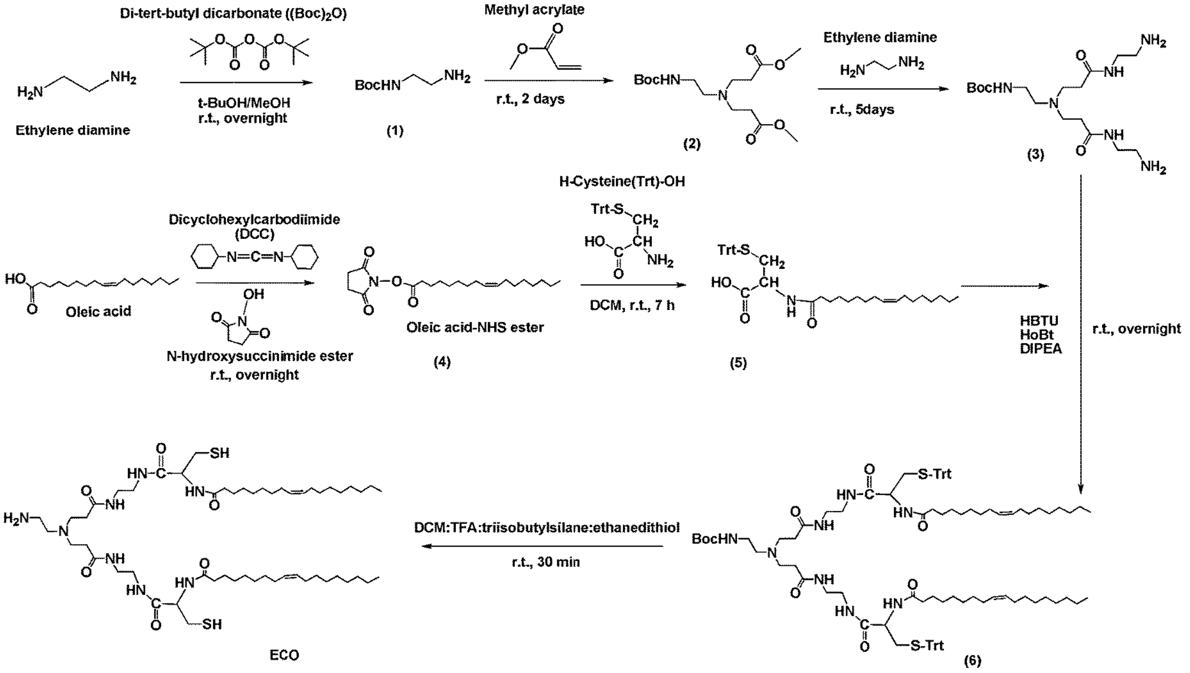
FIG. 24 illustrates synthetic Procedure of ECO.

The compounds having the general formula I can be synthesized using solid phase techniques known in the art. FIGS. 2 and 24 provide exemplary synthetic procedures for preparing the compounds. In general, the approaches in FIGS. 2 and 24 involves the systematic protection/elongation/deprotection to produce a dithiol compound. The hydrophobic group is produced by reacting oleic acid with the amino group present on the cysteine residue. Although FIGS. 2 and 24 depict one approach for producing the compounds of formula I, other synthetic techniques can be used.

Any of the compounds described herein can exist or be converted to the salt thereof. In one aspect, the salt is a pharmaceutically acceptable salt. The salts can be prepared by treating the free acid with an appropriate amount of a chemically or pharmaceutically acceptable base. Representative chemically or pharmaceutically acceptable bases are ammonium hydroxide, sodium hydroxide, potassium hydroxide, lithium hydroxide, calcium hydroxide, magnesium hydroxide, ferrous hydroxide, zinc hydroxide, copper hydroxide, aluminum hydroxide, ferric hydroxide, isopropylamine, trimethylamine, diethylamine, triethylamine, tripropylamine, ethanolamine, 2-dimethylaminoethanol, 2-diethylaminoethanol, lysine, arginine, histidine, and the like. In one aspect, the reaction is conducted in water, alone or in combination with an inert, water-miscible organic solvent, at a temperature of from about 0° C. to about 100° C., such as at room temperature. The molar ratio of the compound to base used is chosen to provide the ratio desired for any particular salts. For preparing, for example, the ammonium salts of the free acid starting material, the starting material can be treated with approximately one equivalent of base to yield a salt.

In another aspect, any of the compounds described herein can exist or be converted to the salt with a Lewis base thereof. The compounds can be treated with an appropriate amount of Lewis base. Representative Lewis bases are ammonium hydroxide, sodium hydroxide, potassium hydroxide, lithium hydroxide, calcium hydroxide, magnesium hydroxide, ferrous hydroxide, zinc hydroxide, copper hydroxide, aluminum hydroxide, ferric hydroxide, isopropylamine, trimethylamine, diethylamine, triethylamine, tripropylamine, ethanolamine, 2-dimethylaminoethanol, 2-diethylaminoethanol, lysine, arginine, histidine, THF, ether, thiol reagent, alcohols, thiol ethers, carboxylates, phenolates, alkoxides, water, and the like. In one aspect, the reaction is conducted in water, alone or in combination with an inert, water-miscible organic solvent, at a temperature of from about 0° C. to about 100° C. such as at room temperature. The molar ratio of the compound to base used is chosen to provide the ratio desired for any particular complexes. For example, the ammonium salts of the free acid starting material, the starting material can be treated with approximately one equivalent of chemically or pharmaceutically acceptable Lewis base to yield a complex.

If the compounds possess carboxylic acid groups, these groups can be converted to pharmaceutically acceptable esters or amides using techniques known in the art. Alternatively, if an ester is present on the dendrimer, the ester can be converted to a pharmaceutically acceptable ester using transesterification techniques.

The compounds described herein have numerous applications with respect to the delivery of nucleic acids to a subject. In some embodiments, the compounds described herein can be used in gene therapy to deliver nucleic acid or genetic materials to cells and tissues.

The nucleic acid can be an oligonucleotide, deoxyribonucleic acid (DNA), ribonucleic acid (RNA), or peptide nucleic acid (PNA). The nucleic acid of interest introduced by the present method can be nucleic acid from any source, such as a nucleic acid obtained from cells in which it occurs in nature, recombinantly produced nucleic acid, or chemically synthesized nucleic acid. For example, the nucleic acid can be cDNA or genomic DNA or DNA synthesized to have the nucleotide sequence corresponding to that of naturally-occurring DNA. The nucleic acid can also be a mutated or altered form of nucleic acid (e.g., DNA that differs from a naturally occurring DNA by an alteration, deletion, substitution or addition of at least one nucleic acid residue) or nucleic acid that does not occur in nature.

In one aspect, the nucleic acid can be a functional nucleic acid. Functional nucleic acids are nucleic acid molecules that have a specific function, such as binding a target molecule or catalyzing a specific reaction. Functional nucleic acid molecules can be divided into the following categories, which are not meant to be limiting. For example, functional nucleic acids include antisense molecules, aptamers, ribozymes, triplex forming molecules, siRNA, miRNA, shRNA and external guide sequences. The functional nucleic acid molecules can act as affectors, inhibitors, modulators, and stimulators of a specific activity possessed by a target molecule, or the functional nucleic acid molecules can possess a de novo activity independent of any other molecules.

Functional nucleic acids can be a small gene fragment that encodes dominant-acting synthetic genetic elements (SGEs), e.g., molecules that interfere with the function of genes from which they are derived (antagonists) or that are dominant constitutively active fragments (agonists) of such genes. SGEs can include, but are not limited to, polypeptides, inhibitory antisense RNA molecules, ribozymes, nucleic acid decoys, and small peptides. The small gene fragments and SGE libraries disclosed in U.S. Patent Publication No. 2003/0228601, which is incorporated by reference, can be used herein.

The functional nucleic acids of the present method can function to inhibit the function of an endogenous gene at the level of nucleic acids, e.g., by an antisense, RNAi or decoy mechanism. Alternatively, certain functional nucleic acids can function to potentiate (including mimicking) the function of an endogenous gene by encoding a polypeptide that retains at least a portion of the bioactivity of the corresponding endogenous gene, and may in particular instances be constitutively active.

Other therapeutically important nucleic acids include antisense polynucleotide sequences useful in eliminating or reducing the production of a gene product, as described by Tso, P. et al Annals New York Acad. Sci. 570:220-241 (1987). Also contemplated is the delivery of ribozymes. These antisense nucleic acids or ribozymes can be expressed (replicated) in the transfected cells. Therapeutic nucleic acids or polynucleotides useful herein can also code for immunity-conferring polypeptides, which can act as endogenous immunogens to provoke a humoral or cellular response, or both. The nucleic acids or polynucleotides employed can also code for an antibody. In this regard, the term "antibody" encompasses whole immunoglobulin of any class, chimeric antibodies and hybrid antibodies with dual or multiple antigen or epitope specificities, and fragments, such as $F(ab)_2$, $Fab^2$, Fab and the like, including hybrid fragments. Also included within the meaning of "antibody" are conjugates of such fragments, and so-called antigen binding proteins (single chain antibodies) as described, for example, in U.S. Pat. No. 4,704,692, the contents of which are hereby incorporated by reference.

In some embodiments the nucleic acid is siRNA. siRNAs are double stranded RNA molecules (dsRNAs) with approximately 20 to 25 nucleotides, which are generated by the cytoplasmic cleavage of long RNA with the RNase III enzyme Dicer. siRNAs specifically incorporate into the RNA-induced silencing complex (RISC) and then guide the RNAi machinery to destroy the target mRNA containing the complementary sequences. Since RNAi is based on nucleotide base-pairing interactions, it can be tailored to target any gene of interest, rendering siRNA an ideal tool for treating diseases with gene silencing. Gene silencing with siRNAs has a great potential for the treatment of human diseases as a new therapeutic modality. Numerous siRNAs have been designed and reported for various therapeutic purposes and some of the siRNAs have demonstrated specific and effective silencing of genes related to human diseases. Therapeutic applications of siRNAs include, but are not limited to, inhibition of viral gene expression and replication in antiviral therapy, anti-angiogenic therapy of ocular diseases, treatment of autoimmune diseases and neurological disorders, and anticancer therapy. Therapeutic gene silencing has been demonstrated in mammals, which bodes well for the clinical application of siRNA. It is believed that siRNA can target every gene in human genome and has unlimited potential to treat human disease with RNAi.

The nucleic acid can be complexed to the carrier compounds described herein by admixing the nucleic acid and the compound or corresponding disulfide oligomer or polymer. The pH of the reaction can be modified to convert the amino groups present on the compounds described herein to cationic groups. For example, the pH can be adjusted to protonate the amino group. With the presence of cationic groups on the compound, the nucleic acid can electrostatically bond (i.e., complex) to the compound. In one aspect, the pH is from 1 to 7.4. In another aspect, the N/P ratio is from 0.5 to 100, where N is the number of nitrogen atoms present on the compound that can be form a positive charge and P is the number of phosphate groups present on the nucleic acid. Thus, by modifying the compound with the appropriate number of amino groups in the head group, it is possible to tailor the bonding (e.g., type and strength of bond) between the nucleic acid and the compound. The N/P ratio can be adjusted depending on the cell type to which the nucleic acid is to be delivered. In some embodiments where the cell is cancer, the N/P ratio can be at least about 6, at least about 10, or at least about 15. In other embodiments, the N/P ration can be from about 6 to about 20.

In one aspect, the nucleic acid/carrier complex is a nanoparticle. In one aspect, the nanoparticle has a diameter of about 1000 nanometers or less.

In other aspects, the compounds described herein can be designed so that the resulting nucleic acid nanoparticle escapes endosomal and/or lysosomal compartments at the endosomal-lysosomal pH. For example, the compound forming nanoparticles with nucleic acids can be designed such that its structure and amphiphilicity changes at endosomal-lysosomal pH (5.0-6.0) and disrupts endosomal-lysosomal membranes, which allows entry of the nanoparticle into the cytoplasm. In one aspect, the ability of specific endosomal-lysosomal membrane disruption of the compounds described herein can be tuned by modifying their pH sensitive amphiphilicity by altering the number and structure of protonatable amines and lipophilic groups. For example, decreasing the number of protonatable amino groups can reduce the amphiphilicity of a nanoparticle produced by the compound at neutral pH. In one aspect, the compounds herein have 1 to 50, 1 to 40, 1 to 30, 1 to 20, 1 to 10, 1 to 8, 1 to 6, 1 to 4, or 2 protonatable amino or substituted amino groups. The pH-sensitive amphiphilicity of the compounds and nanoparticles produced by the compounds can be used to fine-tune the overall pKa of the nanoparticle. Low amphiphilicity of the nanoparticles at physiological pH can minimize non-specific cell membrane disruption and nonspecific tissue uptake of the nucleic acid/MFC system. In certain aspects, it is desirable that the carriers have low amphiphilicity at the physiological pH and high amphiphilicity at the endosomal-lysosomal pH, which will only cause selective endosomal-lysosomal membrane disruption with the nanoparticles.

The surface of the nanoparticle complexes can be modified by, for example, covalently incorporating polyethylene glycol by reacting unpolymerized free thiol of the nanoparticle to reduce non-specific tissue uptake in vivo. For example, PEG-maleimide reacts rapidly with free thiol groups. The molecular weight of the PEG can vary depending upon the desired amount of hydrophilicity to be imparted on the carrier. PEG-modification of the carrier can also protect nanoparticles composed of the nucleic acid from enzymatic degradation upon uptake by the cell (e.g., endonucleases). Targeting groups, including peptides, proteins, antibodies or antibody fragment, can also be incorporated into the nanoparticle complexes during the preparation of the complexes to enhance the delivery specificity and efficiency of the genetic materials to the target cells. Polyethylene glycol can be used as the spacer to conjugate targeting agents to the nanoparticle complexes.

The compounds described herein can be used to introduce a nucleic acid into a cell. The method generally involves contacting the cell with a complex, wherein the nucleic acid is taken up into the cell. In one aspect, the compounds described herein can facilitate the delivery of DNA or RNA as therapy for genetic disease by supplying deficient or absent gene products to treat any genetic disease or by silencing gene expression. Techniques known in the art can used to measure the efficiency of the compounds described herein to deliver nucleic acids to a cell.

The term "cell" as used herein is intended to refer to well-characterized homogenous, biologically pure populations of cells. These cells may be eukaryotic cells that are neoplastic or which have been "immortalized" in vitro by methods known in the art, as well as primary cells, or prokaryotic cells. The cell line or host cell is preferably of mammalian origin, but cell lines or host cells of non-mammalian origin may be employed, including plant, insect, yeast, fungal or bacterial sources.

In one aspect, the cell comprises stem cells, committed stem cells, differentiated cells, primary cells, and tumor cells. Examples of stem cells include, but are not limited to, embryonic stem cells, bone marrow stem cells and umbilical cord stem cells. Other examples of cells used in various embodiments include, but are not limited to, osteoblasts, myoblasts, neuroblasts, fibroblasts, glioblasts, germ cells, hepatocytes, chondrocytes, keratinocytes, smooth muscle cells, cardiac muscle cells, connective tissue cells, glial cells, epithelial cells, endothelial cells, hormone-secreting cells, cells of the immune system, and neurons.

Atypical or abnormal cells such as tumor cells can also be used herein. Tumor cells cultured on substrates described herein can provide more accurate representations of the native tumor environment in the body for the assessment of drug treatments. Growth of tumor cells on the substrates described herein can facilitate characterization of biochemical pathways and activities of the tumor, including gene expression, receptor expression, and polypeptide production, in an in vivo-like environment allowing for the development of drugs that specifically target the tumor.

The complexes (i.e., nanoparticles) described above can be administered to a subject using techniques known in the art. For example, pharmaceutical compositions can be prepared with the complexes. It will be appreciated that the actual preferred amounts of the complex in a specified case will vary according to the specific compound being utilized, the particular compositions formulated, the mode of application, and the particular situs and subject being treated. Dosages for a given host can be determined using conventional considerations, e.g., by customary comparison of the differential activities of the subject compounds and of a known agent, e.g., by means of an appropriate conventional pharmacological protocol. Physicians and formulators, skilled in the art of determining doses of pharmaceutical compounds, will have no problems determining dose according to standard recommendations (Physicians Desk Reference, Barnhart Publishing (1999).

Pharmaceutical compositions described herein can be formulated in any excipient the biological system or entity can tolerate. Examples of such excipients include, but are not limited to, water, saline, Ringer's solution, dextrose solution, Hank's solution, and other aqueous physiologically balanced salt solutions. Nonaqueous vehicles, such as fixed oils, vegetable oils such as olive oil and sesame oil, triglycerides, propylene glycol, polyethylene glycol, and injectable organic esters such as ethyl oleate can also be used. Other useful formulations include suspensions containing viscosity enhancing agents, such as sodium carboxymethylcellulose, sorbitol, or dextran. Excipients can also contain minor amounts of additives, such as substances that enhance isotonicity and chemical stability. Examples of buffers include phosphate buffer, bicarbonate buffer and Tris buffer, while examples of preservatives include thimerosal, cresols, formalin and benzyl alcohol.

Pharmaceutical carriers are known to those skilled in the art. These most typically would be standard carriers for administration to humans, including solutions such as sterile water, saline, and buffered solutions at physiological pH.

Molecules intended for pharmaceutical delivery can be formulated in a pharmaceutical composition. Pharmaceutical compositions can include carriers, thickeners, diluents, buffers, preservatives, surface active agents and the like in addition to the molecule of choice. Pharmaceutical compositions can also include one or more active ingredients such as antimicrobial agents, antiinflammatory agents, anesthetics, and the like.

The pharmaceutical composition can be administered in a number of ways depending on whether local or systemic treatment is desired, and on the area to be treated. Administration can be topically, including ophthalmically, vaginally, rectally, intranasally. Administration can also be intravenously or intraperitoneally. In the case of contacting cells with the nanoparticlar complexes of nucleic acid and MFC described herein, it is possible to contact the cells in vivo or ex vivo.

Preparations for administration include sterile aqueous or non-aqueous solutions, suspensions, and emulsions. Examples of non-aqueous carriers include water, alcoholic/aqueous solutions, emulsions or suspensions, including saline and buffered media. Parenteral vehicles, if needed for collateral use of the disclosed compositions and methods, include sodium chloride solution, Ringer's dextrose, dextrose and sodium chloride, lactated Ringer's, or fixed oils. Intravenous vehicles, if needed for collateral use of the disclosed compositions and methods, include fluid and nutrient replenishers, electrolyte replenishers (such as those based on Ringer's dextrose), and the like. Preservatives and other additives can also be present such as, for example, antimicrobials, anti-oxidants, chelating agents, and inert gases and the like.

Formulations for topical administration can include ointments, lotions, creams, gels, drops, suppositories, sprays, liquids and powders. Conventional pharmaceutical carriers, aqueous, powder or oily bases, thickeners and the like can be necessary or desirable.

Dosing is dependent on severity and responsiveness of the condition to be treated, but will normally be one or more doses per day, with course of treatment lasting from several days to several months or until one of ordinary skill in the art determines the delivery should cease. Persons of ordinary skill can easily determine optimum dosages, dosing methodologies and repetition rates. It is understood that any given particular aspect of the disclosed compositions and methods can be easily compared to the specific examples and embodiments disclosed herein, including the non-polysaccharide based reagents discussed in the Examples. By performing such a comparison, the relative efficacy of each particular embodiment can be easily determined. Particularly preferred compositions and methods are disclosed in the Examples herein, and it is understood that these compositions and methods, while not necessarily limiting, can be performed with any of the compositions and methods disclosed herein.

The following example is for the purpose of illustration only and is not intended to limit the scope of the claims, which are appended hereto.

Example 1

Recently, we have developed a series of novel polymerizable, pH-sensitive, amphiphilic lipid carriers for nucleic acid delivery. One of these carriers, EHCO, has undergone extensive testing in glioblastoma cell lines as a transfection agent for both plasmid DNA and siRNA. EHCO exhibited significant cell membrane disruption capabilities at the endosomal-lysosomal pH, while effectively preserving cell viability. In addition, intravenous administration of targeted EHCO nanoparticles encapsulating anti-HIF-1$\alpha$ siRNA has demonstrated significant inhibition of tumor growth of a flank U87 tumor model. In this Example, we introduced a variety of chemical modifications into the core structure of EHCO and then investigate how they will affect the physiochemical properties and performance of the lipid carrier as a siRNA transfection agent. To accomplish this, we have built a new library of pH-sensitive amphiphilic cationic lipid carriers and have evaluated their transfection capacity.

Figure 1:
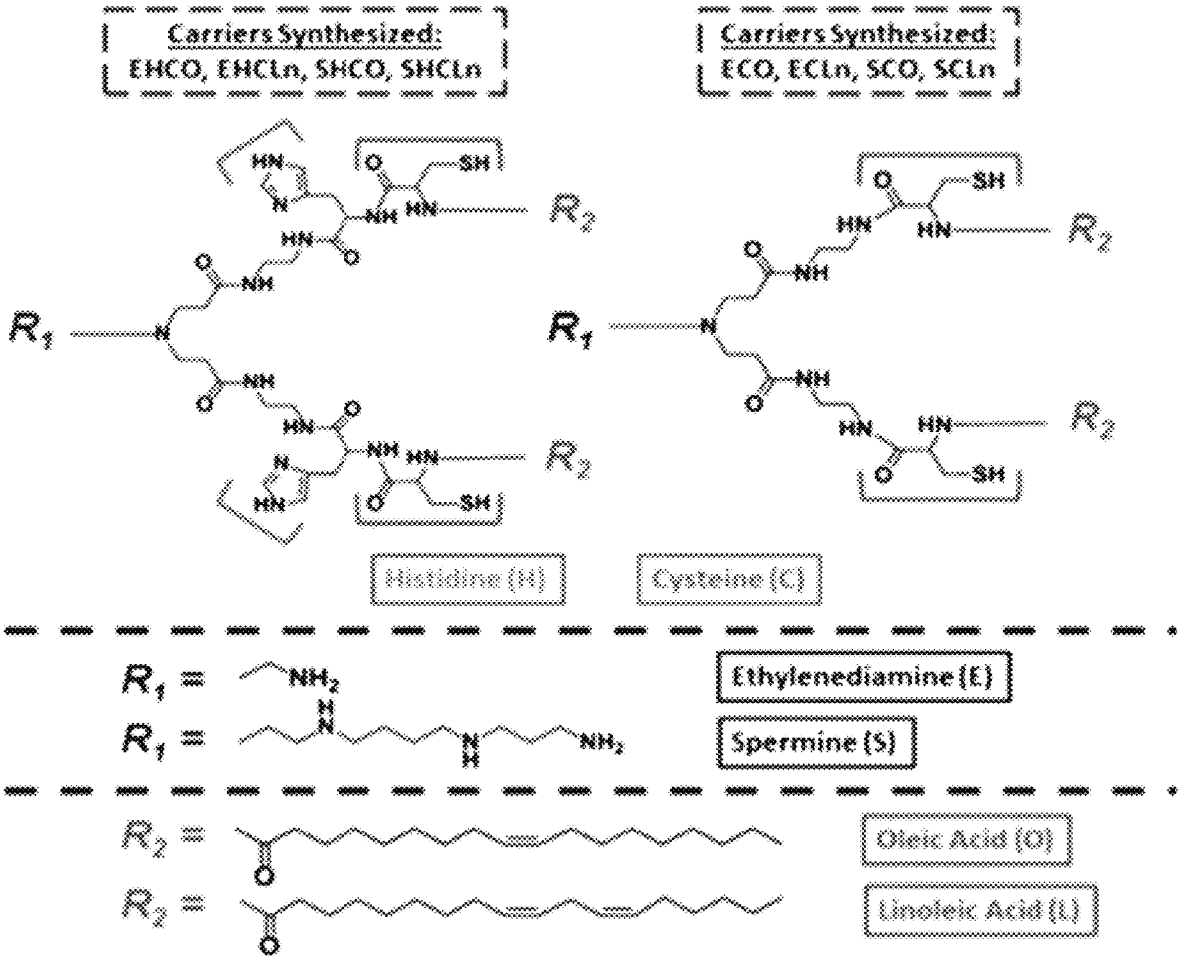
FIG. 1 illustrates chemical structures of synthesized carrier compounds.

EHCO is a cationic lipid that is comprised of three primary domains: a protonable amine-based ethylenediamine head group, a hydrophobic group containing two mono-unsaturated oleic acid tails, and a histidine-cysteine amino acid based linker (FIG. 1). Including EHCO, eight total carriers were synthesized to create the library of transfection agents. Two different chemical scaffolds were incorporated into each of the three domains of the delivery system to investigate (1) the effect of the number of amines of the head group, (2) the degree of unsaturation of the hydrophobic tail domain, and (3) the role of the protonatable histidine residue of the linker group on RNAi-mediated silencing efficacy (FIG. 1). Nanoparticles of various N/P formulations were characterized and screened by a series of in vitro assays evaluating pH-sensitive membrane disruption, cellular uptake, cytotoxicity, and transfection efficiency to determine the optimal carrier and formulation for both a cancerous HT29 colon carcinoma and noncancerous CHO (Chinese hamster ovary) cell line.

Materials and Methods

Materials

2-Chlorotrityl chloride resin, Fmoc-His(Trt)-OH, Fmoc-Cys(Trt)-OH, and benzotriazol-1-yl-oxytripyrrolidinophosphonium hexafluorophosphate (PyB OP) were purchased from EMD Biosciences (San Diego, CA). Ethylenediamine (EDA), spermine, piperidine, trifluoroacetic acid (TFA), 1,2-ethanedithiol (EDT), triisobutylsilane (TIBS), N,N'-diisopropylethylamine (DIPEA), oleic acid, linoleic acid, methyl acrylate, di-tert-butyl dicarbonate (Boc2O), hydrazine, and TCEP (tris(2-carboxyethyl)phosphine) were purchased from Sigma-Aldrich Corporation (St. Louis, MO). Hydroxybenzotriazole (HOBt) was purchased from Peptides International Inc. (Louisville, KY). 2-Acetyldimedone (Dde-OH) was purchased from Chem-Impex International, Inc. (Wood Dale, IN). ISOLUTE columns and accessories for all solid-phase synthesis reactions were purchased from Biotage (Charlotte, NC). All reactions were carried out under an atmosphere of dried nitrogen.

Anti-luciferase siRNA (sense sequence: 5'-CUUACGCUGAGUACUUC GAdTdT-3', anti-sense sequence 5'-UCGAAGUACUCAGCGUAAGdTdT-3') and anti-GFP siRNA (sense sequence: 5'-GCAAGCUGACC-CUGAAGUUCAU-3', antisense sequence: 5'-GAAC-UUCAGG-GUCAGCUUGCCG-3') were purchased from Dharmacon, Inc. (Lafayette, CO). Alexa Fluor 488-labeled anti-luciferase siRNA was purchased from Qiagen (Valencia, CA).

Chinese hamster ovary cells stably expressing a green fluorescent reporter protein (CHO-d1EGFP) were provided by Dr. Charles Roth of Rutgers University. These cells were cultured in F-12 K medium supplemented with 10% FBS (ATCC: Manassas, VA) under constant selective pressure by 500 μg/mL geneticin (Invitrogen: Carlsbad, CA). HT29 human colon carcinoma cells were purchased from ATCC and stably transfected with a luciferase reporter enzyme. These cells were cultured in McCoy's 5A growth medium (Invitrogen) supplemented with 10% FBS, 100 μg/mL streptomycin, and 100 units/mL penicillin.

Preparation of the Lipid Carriers

The multifunctional lipid carriers were synthesized by solid phase techniques in an ISOLUTE column reservoir. The preparation of all carriers followed a common synthetic procedure as outlined in FIG. 2. The carriers with a spermine head group, SCHO and SHCLn, required masking of the two secondary amines of the spermine moiety at the initial stages of the synthesis to prevent unwanted side reactions. Standard peptide synthesis protocols were applied, using the ninhydrin test for detection of free primary amines to monitor reaction completion.

Representative Preparation of SHCO

2-Chlorotrityl resin 1 (500 mg, 1.58 mmol/g) was extensively washed with anhydrous DCM and allowed to swell for 2 h. Then, the resin was washed 2× with DMF, mixed with spermine (1.6 g; 10× molar excess) in DMF (10 mL) and DIPEA (0.3 mL) under a dry nitrogen atmosphere and reacted for 2 h. The resin was washed 3× with DMF and 3× with DCM to produce amine 2. The chlorine residues on the resin that did not react with spermine were substituted by a methoxy group upon treatment with a mixture of MeOH/DIPEA/DCM (17/2/1 v/v/v) after a 30 min treatment. The resin was washed with DMF/DCM, mixed with Dde-OH 2.16 g) in DMF (10 mL) and DIPEA (0.3 mL) under an inert nitrogen atmosphere and reacted for 12 h. Then, the resin was washed with DMF/DCM to afford diketone 3. Boc2O (17.24 g) was dissolved in DMF (10 mL) and DIPEA (0.6 mL) and the mixture was added to the resin under a nitrogen atmosphere and reacted for 6 h. The resin was then washed with DMF/DCM to produce intermediate 4. Three consecutive treatments of 4 with a solution of hydrazine (10 mL of 2% (v/v) in DMF) in 15 min interval periods, followed by a DMF/DCM wash, afforded intermediate 5. Next, the resin was transferred into a round bottom flask with anhydrous DMF (10 mL). A large excess of methyl acrylate (50 mL) was added and allowed to react for 5 days at 50° C. under an inert nitrogen atmosphere. Upon completion of the reaction, the resin was transferred back into an ISOLUTE column and washed with DMF/DCM to produce diester 6. Next, the resin was transferred into another round bottom flask containing anhydrous DMF (10 mL) and ethylenediamine (50 mL) under an inert nitrogen atmosphere and reacted for 5 days at 50° C. Subsequently, the resin was transferred back into a column and washed with DMF/DCM to yield bis-amine 7. Fmoc-His(Trt)-OH amino acid (2 g) was added onto the resin with PyBop (1.6 g), HOBt (427 mg), and DIPEA (1.1 mL) in DMF (10 mL) under an inert nitrogen atmosphere and reacted for 4 h. The resin was then treated with piperidine (20% (v/v) in DMF) three consecutive times with 20 mM interval periods, followed by a DMF/DCM wash to afford intermediate 8. At this stage, we repeated the same coupling procedure, as described above, by substituting Fmoc-Cys(Trt)-OH in place of Fmoc-His (Trt)-OH to generate intermediate 9. The lipid tail was incorporated onto intermediate 9 by applying the same coupling procedure as above, but instead using oleic acid (1 mL) to produce intermediate 10. The desired lipid carrier SHCO (11) was released from the resin upon treatment with a mixture of TFA/H2O/EDT/TIBS (4 mL; 94/2.5/2.5/1 v/v/v) under an inert nitrogen atmosphere after 3 h. The lipid carrier 11 was then precipitated by adding TFA into cold diethyl ether at a TFA:diethyl ether 1:40 volume ratio. The precipitated product was filtered and dissolved in a 50/50 mixture of water and acetonitrile and then purified using a reverse phase preparative HPLC gradient method (0 mM: 10% ACN, 90% H2O/110 mM: 100% ACN). An 1100 series Agilent HPLC system was used, equipped with a ZORBAX PrepHT C-18 column. Prior to each run on the HPLC, the lipid carrier was mixed with a 5× molar excess of a 1 M TCEP solution to break any possible disulfide bonds that may have formed between the cysteine residues. The SHCO final product was characterized by using MALDI-TOF mass spectrometry (Bruker Corporation) and stored under nitrogen gas at −20° C. to prevent oxidation of free thiols.

The SHCLn lipid carrier was prepared and purified similarly to SHCO, with the exception that linoleic acid (1 mL) was used in place of oleic acid. The ethylenediamine-based carriers were also prepared according to the SHCO synthetic procedure, with the elimination of the initial primary amine protection (Dde-OH) and de-protection (hydrazine) steps, which were required in the spermine-based carriers in order to protect (Boc2O) the secondary amines of the spermine moiety.

Particle Formulation and Characterization

The cationic lipid carriers are dissolved in ethanol at a stock concentration of 2.5 mM, while all siRNA is reconstituted in nuclease-free water at a 0.25 μg/μL (18.8 μM) concentration. Nanoparticles are formulated by mixing the carriers with siRNA for a period of 30 min in RNase-free phosphate buffer saline (PBS) at pre-specified N/P ratios (N=number of protonable amines in lipid, P=number of phosphate groups in the siRNA). In preparing the lipoplexes, proper dilutions were made such that the volume ratio of ethanol:water was kept constant at 1:20. Minimizing the amount of ethanol is important because it is effective in dissolving lipids, thus inhibiting particle formation. The diameters (as determined by dynamic light scattering) and zeta potentials of all nanoparticles were analyzed using a Malvern Zetasizer instrument at pH=7.4. siRNA encapsulation efficiency was calculated using a RiboGreen fluorescence-based assay from Invitrogen, designed specifically for detection of free RNA at emission and excitation wavelengths of 480 and 520 nm, respectively. Nanoparticles were created with all carriers in the library so that final siRNA concentrations were 1.6 μg/mL. A linear standard curve was utilized to calculate the encapsulation efficiencies from signal intensities measured by a SpectraMax microplate reader (Molecular Devices).

Intracellular Gene Silencing Efficiency

The RNAi induced silencing capabilities of each carrier was investigated in both a CHO-GFP non-cancerous cell line and an HT29-Luc (luciferase) human colon cancer cell line. Approximately 50,000 CHO-GFP cells were seeded into 6 well plates. When 25% confluency was achieved, the growth media were replaced with fresh serum free transfection media containing siRNA nanoparticles, at a dose of 100 nM siRNA. Negative controls included cells that were either treated with naked anti-GFP siRNA or with plain serum-free media. N/P ratios of 4, 6, 8, 10, 12, and 14 were tested for each carrier to determine the optimal nanoparticle formulation. In order to compare the silencing capabilities of the agents designed in our library with commercially available alternatives, Lipofectamine RNAiMax particles were formulated and transfected according to the manufacturer's specifications, and did not undergo changes in N/P ratios. After 4 h, the media were removed and replaced with fresh complete growth media, and cells were allowed to grow for another 24, 48, or 72 h post-transfection. At each of these time points, the CHO-GFP cells were rinsed twice with PBS, trypsinized, and fixed with 2% paraformaldehyde. Flow cytometry using a BD Biosciences FACSCalibur machine enabled us to determine the GFP expression in every sample. Cell-Quest software was used to analyze the results and obtain mean fluorescence intensity (MFI) values. GFP expression for each replicate was calculated relative to the control samples that did not receive any siRNA treatment.

Gene silencing efficiency was investigated in the HT29-Luc cell line by analyzing the expression of a luciferase reporter after anti-Luc siRNA therapy. To perform this study, cancer cells were seeded in 12 well plates at a density of 20,000 cells per well. Transfections were conducted in fresh serum-free media with 100 nM of siRNA when the cells were 25% confluent. The cells continued to grow in normal growth media for an additional 48 and 72 h, at which point they were rinsed twice with PBS and lysed for protein collection. The lysis buffer was a component of a Promega Luciferase Assay kit designed for measuring luciferase expression in the cell lysate. Equally important, the lysis buffer was compatible with the BCA protein assay so that we were able to normalize the luciferase expression in our samples with total protein content. For this silencing study, all synthesized carriers were evaluated at N/P ratios of 8, 10, 12, 14, 16, 18, and 20 to determine the best transfection formulation. Relative luciferase expression was determined for each trial using a SpectraMax luminometer upon the addition of a light-inducing luciferin substrate to the collected protein.

Cytotoxicity

Cytotoxicity of the carriers was investigated using an MTT colorimetric assay measuring cellular metabolic activity (Invitrogen). The transfection procedure was identical to that presented for the reporter knockdown studies above, except for the fact that 96 well plates were utilized instead, and seeded with 10,000 cells per well. After transfection, the cells were allowed to grow for an additional 48 h. At that point, they were incubated with MTT for 4 h, followed by an additional 4 hour incubation with an SDS-HCl solution to dissolve any insoluble formazan crystals formed by the reduction of MTT by NAD(P)H-dependent enzymes in the cells. The absorbance of each sample was measured at 570 nm using a SpectraMax microplate reader. Cellular viability was calculated by averaging the signal intensities over three replicates and then normalizing the results relative to the negative control data.

Cellular Uptake Via Flow Cytometry

Flow cytometry was used to investigate the cellular uptake of our delivery system in HT29 colon carcinoma cells. All carriers in the library were formulated into nanoparticles by condensing Alexa Fluor 488-labeled siRNA at the optimal N/P ratio determined by the above luciferase knockdown studies. Approximately 50,000 cancer cells were seeded in 6-well plates and allowed to grow until 30-50% confluence was reached. The cancer cells were transfected with a 100 nM siRNA dose in serum-free media. After 4 h, the transfection media were aspirated and the cells were washed twice with PBS. The cells were then trypsinized, collected, and fixed with 2% paraformaldehyde in PBS, prior to flow cytometric analysis.

Evaluation of pH-Sensitive Membrane Disruption

Hemolytic activity of each carrier was determined to verify the pH-sensitive membrane disruption capabilities of each carrier in the delivery system. Red blood cells (RBCs) extracted from rats were purchased from Innovative Research Inc. (Novi, MI) and diluted 1:50 in PBS solutions of pHs=5.4, 6.5, or 7.4. A total of 100 μL of nanoparticles were created at N/P ratios of 5, 10, 15 and then incubated with 100 μL of diluted RBCs at 37° C. for 2 h. Nanoparticles were formulated so that the final amine concentration for all the samples, after mixing with the RBCs, was 150 μM. Multiple pHs were tested to predict if the nanoparticles could disrupt membranes of the endosomal-lysosomal compartments (pH=5-6), without affecting the integrity of the outer cell membrane prior to endocytosis (pH=7.4). The absorbance of each test sample was measured on a SpectraMax spectrophotometer at a wavelength of 540 nm in order to determine the amount of hemoglobin released from the RBCs, due to membrane destabilization, relative to that achieved by a positive control treatment of 1% (v/v) Triton-X100 surfactant during the 2 hour incubation period.

Intracellular Release of siRNA

Live-cell confocal imaging was utilized to image the intracellular release and dispersion of siRNA following transfection with the lipid carrier that performed best during the reporter knockdown studies. Approximately 50,000 HT29-Luc cells were seeded onto glass-bottom dishes (MatTek—Ashland, MA). Once 40% confluency was established, the cells were stained with 75 nM LysoTracker Red DND-99 (Invitrogen) for 30 min in normal growth medium. Afterwards, the cells were transfected with 100 nM Alexa Fluor 488-labeled anti-Luc siRNA in fresh serum-free media using the designed cationic lipid agent that performed the best in the above reporter knockdown experiments. Imaging commenced 5 min post-transfection using an Olympus FV1000 confocal microscope, and continued periodically over the first 2 h. Throughout the course of the study, all cells were kept alive on the microscope in a humidified weather station under normal gas conditions (5% $CO_2$). Another image was acquired after 24 h following re-administration of the LysoTracker stain.

Statistical Analysis

Statistical analyses were performed using ANOVA and two-tailed Student's t-tests with a 95% confidence interval. Probability values of p b 0.05 were considered significant.

Results

Synthesis of Cationic Lipid Library

The structures and names of all eight cationic lipids in the designed library are shown in FIG. 1. Each transfection agent represents a different combination of 2 protonable cationic head groups (ethylenediamine or spermine), 2 fatty acid tails (mono- or di-alkene unsaturated oleic and linoleic acids), and 2 linker domains (cysteine or histidine-cysteine). Peptide synthesis protocols were employed to create each carrier by solid phase chemistry, using the representative synthetic procedure for the preparation of the spermine-based carrier SHCO shown in FIG. 2.

Carriers with an ethylenediamine (EDA) head group required fewer synthetic steps than their spermine-based analogs. After attaching the EDA head group onto 2-chlorotrityl resin, the reaction directly proceeded to the Michael addition of methyl acrylate to the primary amine. In contrast, preparation of the spermine carriers required two additional synthetic steps to mask the secondary amines of the spermine moiety and avoid unwanted side reactions. All final carriers were purified by preparative HPLC and verified by mass spectrometry. The calculated (m/z) and measured ([M+H]+) molecular weights of each cationic lipid are summarized in Table 1. No evidence of byproducts was observed in any of the mass spectra.

TABLE 1 measured mass of cationic lipid carriers by MALDI-TOF mass spectrometry

| Transfection agent | Formula | Mx (calc m/z) | Mw (found) $[M + 1]^+$ |
|---|---|---|---|
| EHCO | $C_{66}H_{116}N_{14}O_8S_2$ | 1296.85 | 1297.72 |
| EHCLn | $C_{66}H_{112}N_{14}O_8S_2$ | 1292.82 | 1293.38 |
| ECO | $C_{54}H_{102}N_8O_6S_2$ | 1022.74 | 1023.16 |
| ECLn | $C_{54}H_{98}N_8O_6S_2$ | 1018.71 | 1019.11 |
| SHCO | $C_{74}H_{134}N_{16}O_8S_2$ | 1439.00 | 1439.86 |
| SHCLn | $C_{74}H_{130}N_{16}O_8S_2$ | 1434.97 | 1435.48 |
| SCO | $C_{62}H_{120}N_{10}O_6S_2$ | 1164.88 | 1165.42 |
| SCLn | $C_{62}H_{116}N_{10}O_6S_2$ | 1160.85 | 1161.19 |

Nanoparticle Characterization and siRNA Encapsulation

The complexation of cationic lipids with siRNAs investigated utilizing dynamic light scattering (DLS) and a RiboGreen fluorescence based assay that can detect free, non-encapsulated RNA. Nanoparticle formation was observed when both the lipids and siRNA were mixed together at N/P ratios above 1.0, as determined by the RiboGreen assay (data not shown). However, few particles were formulated at this N/P ratio as evidenced by the fact that more starting materials were required to obtain a DLS reading.

Figure 3:
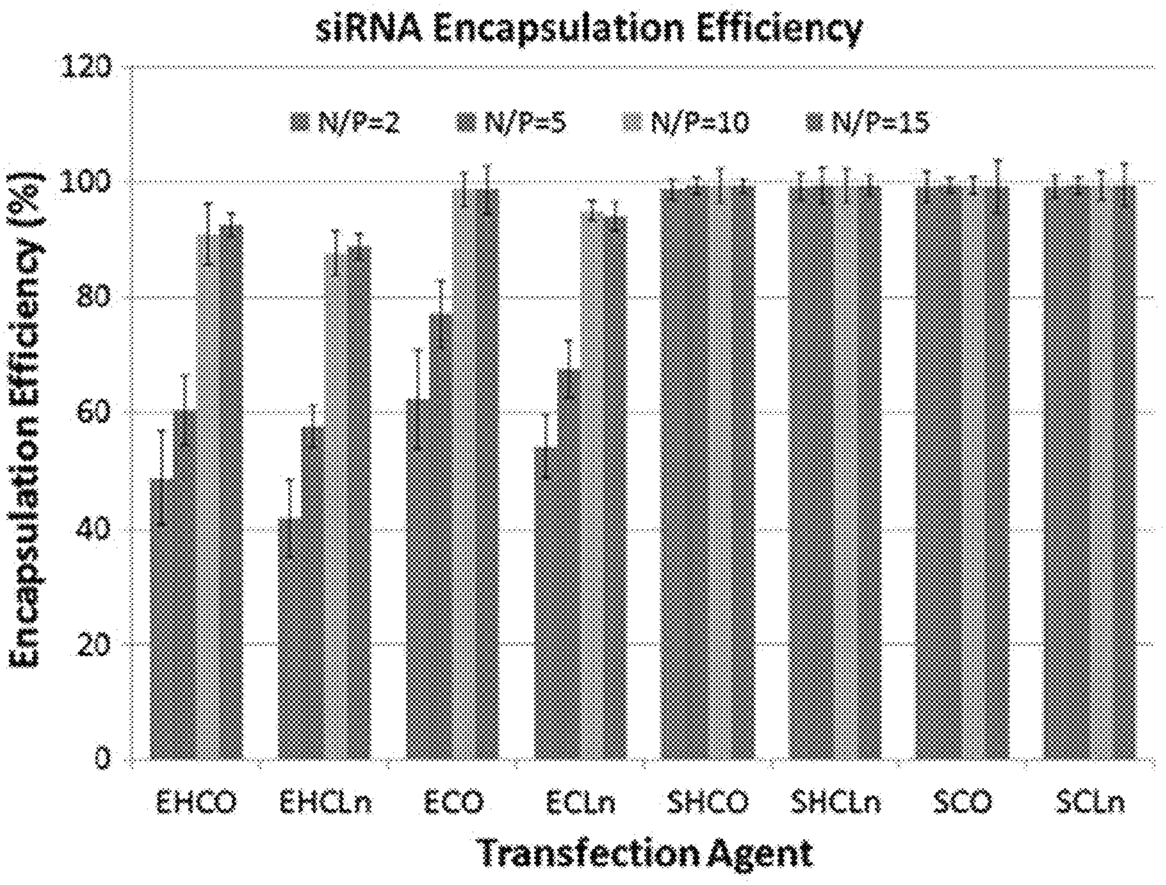
FIG. 3 illustrates siRNA encapsulation efficiencies for all carriers in the library over multiple N/P ratios.
Figure 4A:
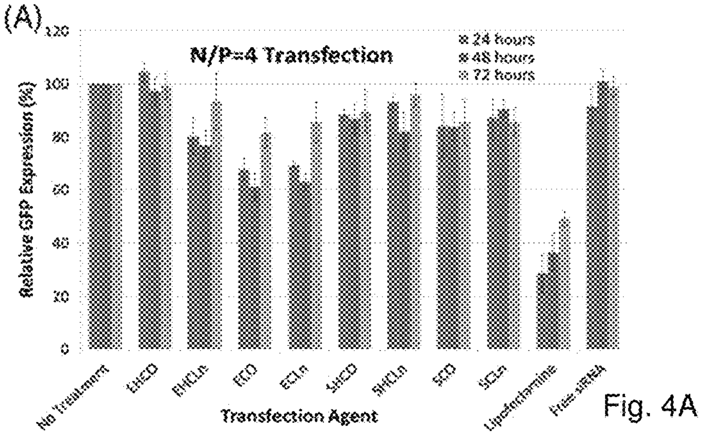
FIGS. 4(A-D) illustrate graphs showing silencing of a GFP reporter protein in Chinese hamster ovary (CHO) cells conducted at a siRNA concentration of 100 nM over 4 h, using formulations of N/P=4 (A), N/P=8 (B), and N/P=12 (C). The majority of the carriers were able to reduce GFP expression to at least 20% 72 h post-transfection. At N/P=12, all but one of the lipid carriers (EHCO) possessed superior long-term silencing capabilities over the commercial agent, Lipofectamine RNAiMax, as evidenced by the fact that GFP expression did not begin to recover at the 72 hour time point. Maximum knockdown of the reporter was achieved at N/P=12 for all the carriers, while maintaining over 80% cell viability (D).
Figure 4B:
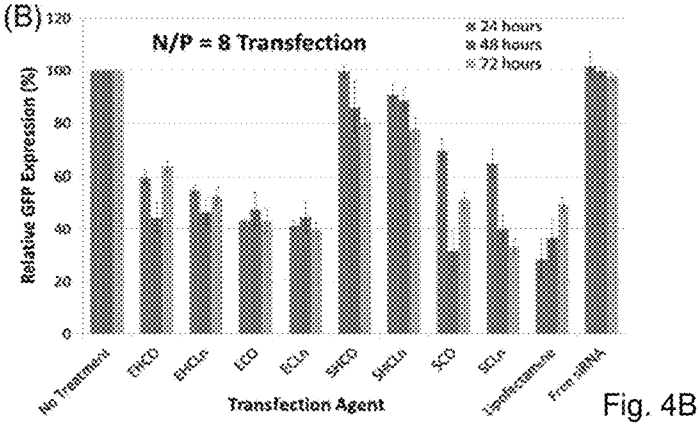
Figure 4C:
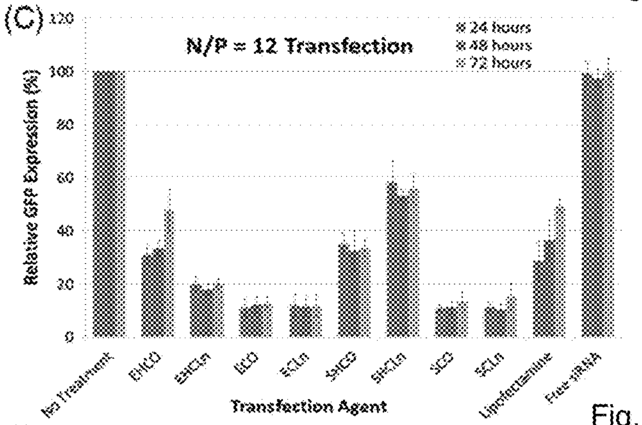
Figure 4D:
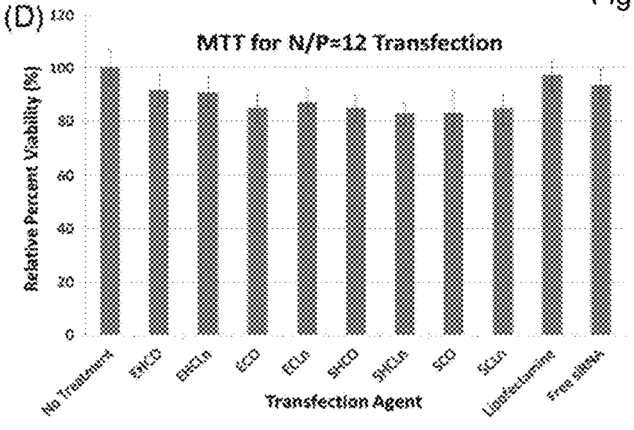
Figure 5A:
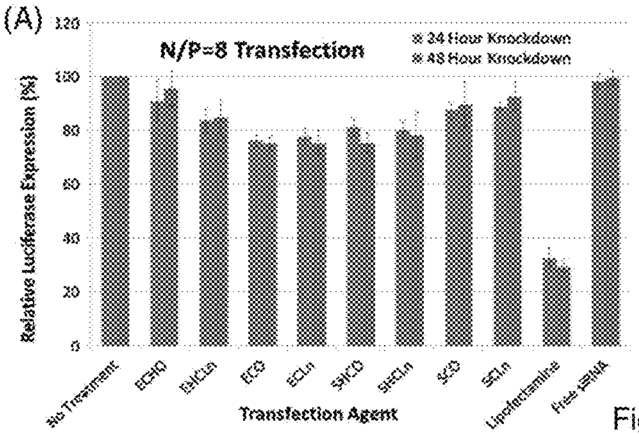
FIGS. 5(A-D) illustrate graphs showing silencing of a luciferase reporter protein in HT29 cancer cells conducted at a siRNA concentration of 100 nM over 4 h, using formulations of N/P=8 (A), N/P=12 (B), and N/P=18 (C). The results above show that ECO and ECL where the most robust of all the carriers 72 h post-transfection, even outperforming the Lipofectamine RNAiMax commercial agent (p b 0.05). Maximum knockdown of the reporter was achieved at N/P=18 for all the carriers, while maintaining over 80% cell viability (D).
Figure 5B:
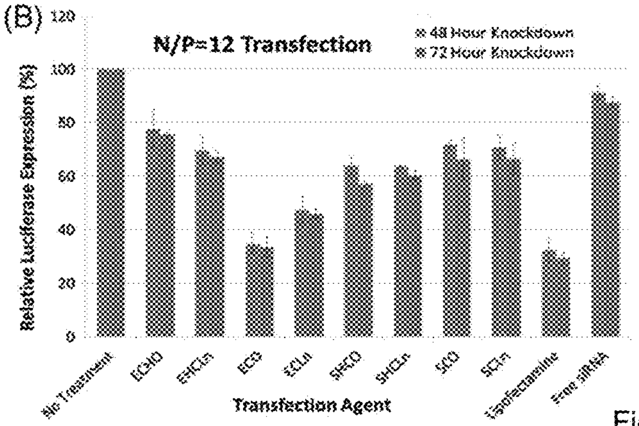
Figure 5C:
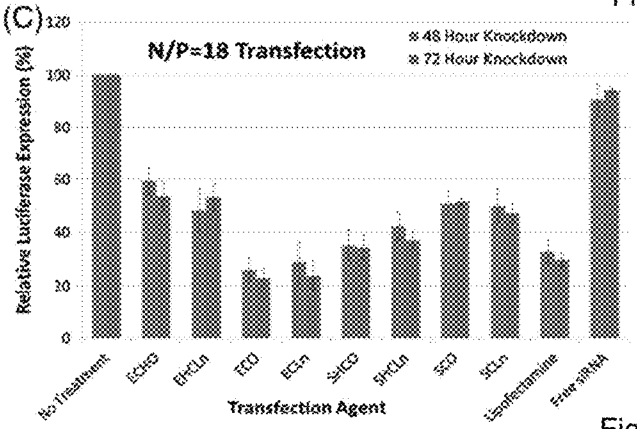
Figure 5D:
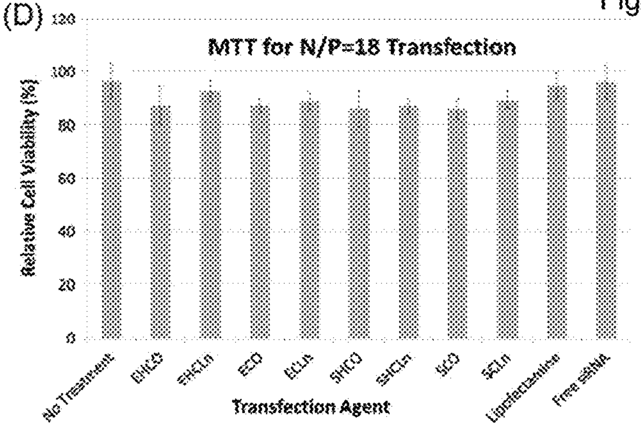

Size, polydispersity, and zeta-potential data for each carrier at five different N/P ratios are shown in Tables 2-4. It was observed that particle diameter and polydispersity decreased as the N/P ratio was increased for each of the transfection agents, and no noticeable trend was observed between carriers with different head and/or lipid tail groups. Lipoplexes were generally greater than 400 nm in diameter at N/P=2, and then ranged between 42 and 75 nm at N/P=15. In addition, the zeta-potentials all appeared to increase with the N/P ratio as well. However, nanoparticles with spermine-based head groups exhibited a significantly quicker change in zeta-potential. The charges of these particles remained nearly constant between 23 and 28 mV at N/P=5 and above. However, those with EDA head groups exhibited a more gradual change in zeta-potential, and were still negative in charge at N/P=5. ECO and ECLn nanoparticles essentially reached their maximum positive charge density at N/P=8, unlike those made from EHCO and EHCLn, which did not attain their greatest electrostatic charge density until N/P=15. In addition to their greater charge at N/P=8, ECO and ECLn lipoplexes were observed to be much smaller in size than their EHCO and EHCLn counterparts. siRNA encapsulation efficiency was nearly 100% for all spermine-base carriers at N/P formulations as low as 2; however 90% encapsulation for all EDA-based agents was not achieved until the N/P ratio was increased to 10 and above (FIG. 3). This suggests that the spermine head groups, with two additional amines compared to their EDA counterparts, are more efficient at condensing siRNA into nanoparticles.

TABLE 2

Nanoparticle diameter (nm) as measured by dynamic light scattering

| | EHCO | EHCLn | ECO | ECLn | SHCO | SHCLn | SCOn | SCLn |
|---|---|---|---|---|---|---|---|---|
| N/P = 2 | 480 ± 30 | 403 ± 35 | 468 ± 43 | 451 ± 34 | 441 ± 32 | 559 ± 38 | 407 ± 35 | 482 ± 40 |
| N/P = 5 | 427 ± 25 | 379 ± 28 | 448 ± 23 | 386 ± 20 | 238 ± 27 | 223 ± 23 | 138 ± 28 | 185 ± 22 |
| N/P = 8 | 380 ± 18 | 227 ± 20 | 59 ± 11 | 126 ± 14 | 139 ± 17 | 119 ± 13 | 63 ± 12 | 51 ± 14 |
| N/P = 10 | 141 ± 15 | 130 ± 14 | 78 ± 12 | 112 ± 11 | 151 ± 16 | 132 ± 15 | 65 ± 11 | 50 ± 12 |
| N/P = 15 | 51 ± 10 | 60 ± 11 | 42 ± 9 | 47 ± 12 | 46 ± 8 | 75 ± 10 | 53 ± 9 | 48 ± 12 |

TABLE 3

Polydispersity of siRNA-lipid complexes

| | EHCO | EHCLn | ECO | ECLn | SHCO | SHCLn | SCOn | SCLn |
|---|---|---|---|---|---|---|---|---|
| N/P = 2 | 0.276 | 0.299 | 0.245 | 0.246 | 0.238 | 0.246 | 0.339 | 0.298 |
| N/P = 5 | 0.195 | 0.197 | 0.200 | 0.276 | 0.192 | 0.183 | 0.236 | 0.233 |
| N/P = 8 | 0.165 | 0.167 | 0.157 | 0.177 | 0.189 | 0.174 | 0.19 | 0.140 |
| N/P = 10 | 0.122 | 0.112 | 0.136 | 0.136 | 0.154 | 0.114 | 0.158 | 0.184 |
| N/P = 15 | 0.161 | 0.127 | 0.005 | 0.055 | 0.124 | 0.163 | 0.176 | 0.180 |

TABLE 4

| Zeta-potential (mV) of siRNA-lipid complexes at pH = 7.4 | | | | | | | | |
|---|---|---|---|---|---|---|---|---|
| | EHCO | EHCLn | ECO | ECLn | SHCO | SHCLn | SCOn | SCLn |
| N/P = 2 | −23.14 ± 2.47 | −23.73 ± 2.26 | −32.20 ± 0.90 | −26.91 ± 1.37 | −32.09 ± 1.65 | −32.09 ± 1.65 | −29.49 ± 1.33 | −28.35 ± 3.61 |
| N/P = 5 | −14.09 ± 1.88 | −17.04 ± 1.32 | −16.84 ± 1.58 | −18.5 ± 2.43 | −18.5 ± 2.43 | 24.02 ± 1.07 | 26.60 ± 2.76 | 26.89 ± 1.85 |
| N/P = 8 | 5.54 ± 1.37 | 0.49 ± 1.17 | 28.82 ± 1.03 | 18.32 ± 1.45 | 18.32 ± 1.45 | 26.35 ± 1.40 | 23.16 ± 1.88 | 26.03 ± 2.25 |
| N/P = 10 | 18.80 ± 1.02 | 11.34 ± 1.67 | 25.68 ± 2.02 | 21.76 ± 2.31 | 21.76 ± 2.31 | 25.59 ± 2.22 | 23.29 ± 3.11 | 28.59 ± 2.25 |
| N/P = 15 | 22.68 ± 2.08 | 24.92 ± 2.89 | 25.19 ± 2.32 | 23.94 ± 1.70 | 23.94 ± 1.70 | 23.80 ± 2.95 | 25.16 ± 3.75 | 17.15 ± 2.99 |

RNAi-Mediated Silencing of Reporter Proteins in CHO-GFP and HT29-Luc Cells

Transfections were conducted in both a non-cancerous (CHO) and cancerous (HT29) cell lines in order to determine the silencing efficiency of each carrier upon delivery of siRNA against GFP and luciferase reporter proteins. It was found that RNAi-mediated knockdown was more effective as the N/P ratios were increased. Nanoparticle characterizations showed that increasing N/P made the lipoplexes more positively-charged and reduced their diameters, both of which are factors that can significantly improve cell uptake efficiency.

FIG. 4 shows that only ECO and ECLn achieved greater than 20% knockdown in CHO-GFP cells at 24 and 48 h post-transfection at N/P=4, reducing the relative reporter expression to 61.0±5.05% and 62.9±3.30%, respectively at the 48 hour time point. The zeta-potential data presented in Table 4 suggest that the lipoplexes they form at this N/P ratio are negative, potentially inducing electrostatic repulsion with the cell membrane during passive uptake. Transfection efficiencies were best at N/P=12 for all agents tested. Five out of the eight carriers were able to mediate at least 80% knockdown of the GFP reporter protein from 24 to 72 h post-transfection. In fact, 6 of the 8 carriers out-performed the commercial agent Lipofectamine-RNAiMax after 72 h by achieving longer-lasting silencing effects. Cytotoxicity at N/P=12 was minimal for all of the transfection agents, due to the fact that the lowest relative cell viability, as determined from an MTT assay, was 83.3±4.22% by the SHCLn lipid carrier. N/P ratios above 12 caused much greater levels of cytotoxicity, decreasing cell viability to approximately 40-50% for all carriers in the synthesized library.

The transfection efficiencies of the carriers were further determined in an HT29 human colon carcinoma cell line stably expressing a luciferase reporter. The silencing effects were apparent in the HT29 cells only after 48 h post-transfection, as opposed to after 24 h in the above CHO-GFP study (data not shown). However, like before, long-term silencing was still observed at the 72 hour time point. FIG. 5 shows that greater N/P ratios were required to achieve significant knockdown effects, compared to those used for the CHO-GFP transfections. Carriers that achieved between 35 and 50% knockdown of the GFP reporter in CHO cells at the N/P=8 formulation, could only induce between 10 and 25% knockdown of the luciferase reporter in the HT29 cell line. When the N/P ratio was increased to 12, ECO and ECLn were found to perform significantly better than the other transfection agents. Luciferase expression was reduced to 33.5±3.82% and 45.8±1.88% by ECO and ECLn, respectively, after 72 h. None of the other carriers reduced luciferase expression below 57.1±1.76%. These results were inferior to those obtained from the CHO-GFP transfections, and as a result, the N/P ratio was increased to 18 to further improve the silencing capability of each carrier. At this formulation, ECO and ECLn were able to reduce luciferase expression to 22.7±3.31% and 23.5±5.11% of their pretreatment levels after 72 h, which was superior to that achieved by Lipofectamine (29.4±2.29%). The rest of the carriers silenced reporter expression to between 34.0±4.76% and 53.7±5.75% relative to the negative control non-treated samples. Formulations at higher N/P ratios induced greater levels of cell death, with cell viabilities falling from 87.3±2.72% and 88.9±6.84% at N/P=18 to 51.5±5.87% and 53.7±6.92% at N/P=20 for the ECO and ECLn transfection agents, respectively.

Determination of Hemolytic Activity

Figure 6A:
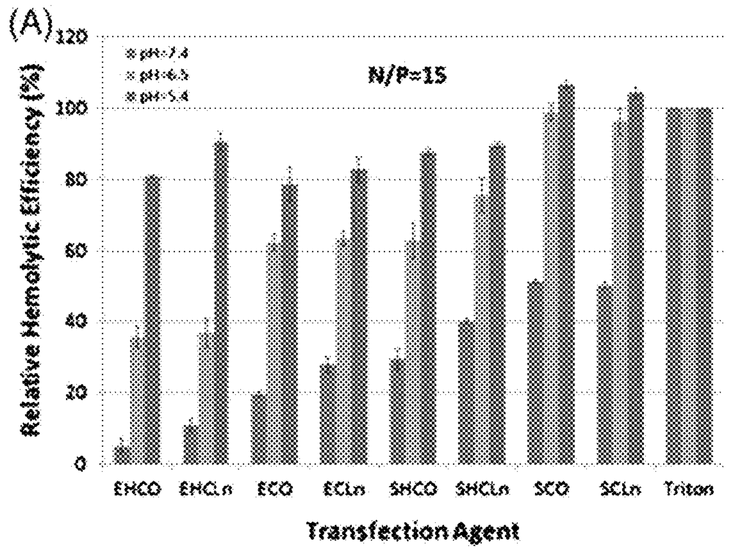
FIGS. 6(A-C) illustrate graphs showing pH-dependent hemolytic activities of all carriers at N/P lipoplex formulations of 15 (A), 10 (B), and 5 (C). Rat blood cells were diluted 1:50 in PBS and incubated with each formulation at pH=7.4, 6.5, and 5.4 for 2 h at 37° C. Triton X-100 (1% v/v) was implemented as a positive control. Each carrier exhibited pH-sensitive membrane destabilization properties as the hemolytic activities were found to significantly increase (p b 0.05) as the acidity of the environment was reduced.
Figure 6B:
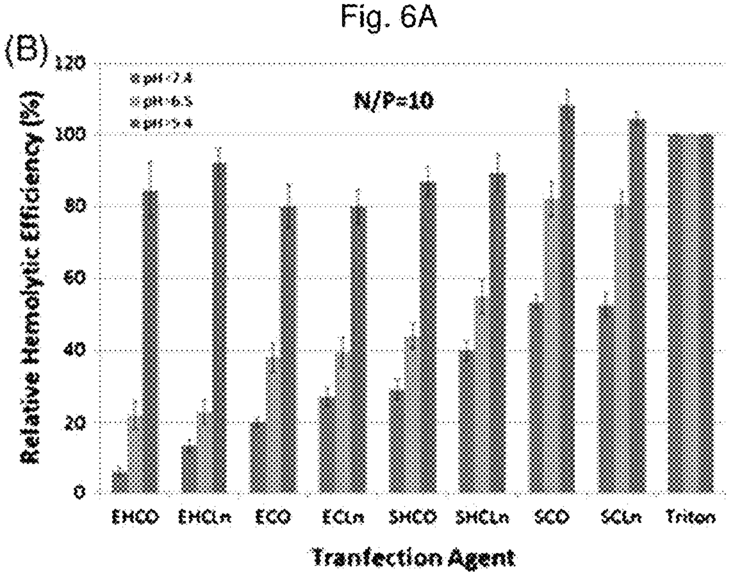
Figure 6C:
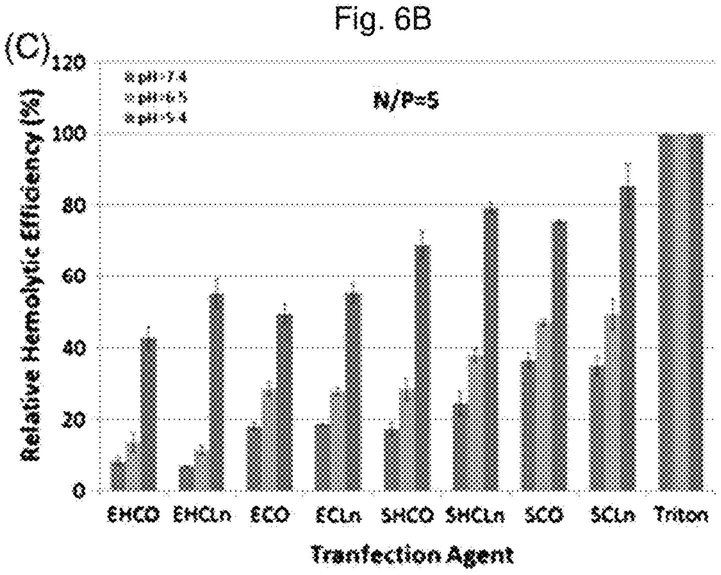

In an attempt to understand why ECO and ECLn were the best carriers from the library, meeting our target of at least 75% knockdown efficiency with 80% cell viability, we first analyzed the membrane disruptive capabilities of each agent using a hemolysis assay. FIG. 6 shows that all carriers exhibited significant pH-sensitive hemolytic activity, and that increasing the N/P ratios generally improved their membrane disruptive properties. It was also observed that increasing the N/P ratio from 10 to 15 did not affect the hemolytic activity at pH=5.4, but rather significantly improved RBC destabilization at pH=6.5, which is known to be the pH of the environment inside endosomal compartments. Therefore, it is possible that increasing the N/P ratio results in better RNAi-mediated reduction of HT29 luciferase expression by improving endosomal escape and allowing the delivery siRNA to evade the degradative lysosomal environment. Despite the fact that both ECO and ECLn possessed the greatest silencing efficiencies, they were not the most robust at inducing membrane destabilization events. Instead, the SCO and SCLn carriers exhibited the greatest hemolytic activity relative to Triton X-100 at all N/P ratios and pHs tested. Nonetheless, the degree of hemolytic activity ECO and ECLn expressed at pH=6.5 was also matched by SHCO and SHCLn, even though these cationic lipids were not as effective in transfecting the HT29 cancer cells.

Cellular Uptake

Figure 7:
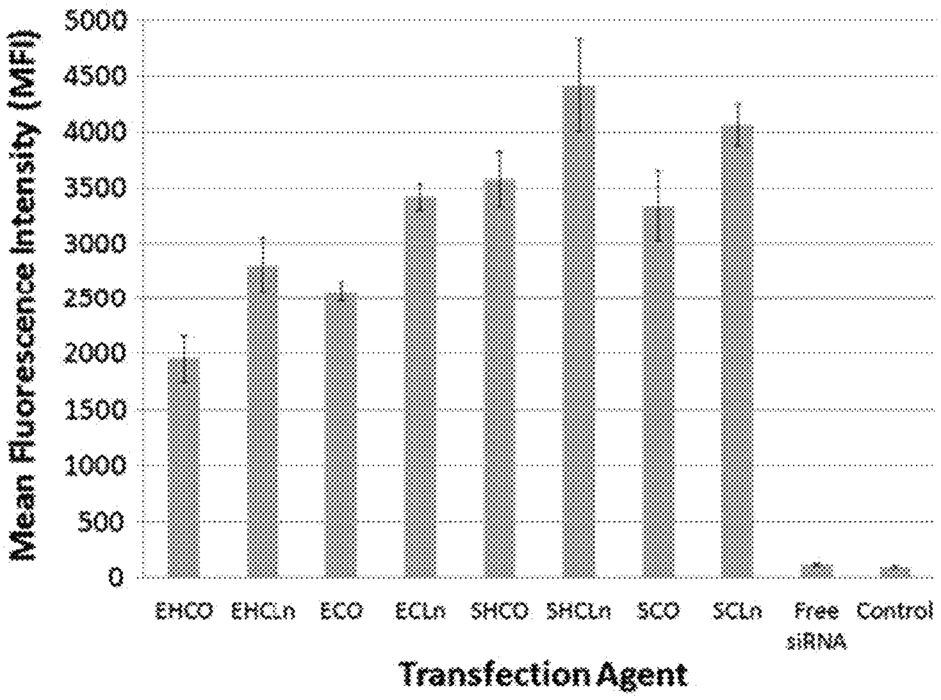
FIG. 7 illustrates a graph showing flow cytometric analysis of cellular uptake in HT29 cancer cells at N/P=18 formulations. Transfections were performed over a 4 hour period at a siRNA concentration of 100 nM. Mean fluorescence intensity (MFI) values are reported here.

Flow cytometry was utilized to determine the cellular uptake of each carrier complexed with Alexa Fluor 488-labeled siRNA at N/P=18. The mean fluorescence intensity (MFI) values presented in FIG. 7 were calculated from the acquired histograms and used to determine if the cellular uptake was correlated to transfection efficiency in HT29 cancer cells. Similar to hemolytic results, ECO and ECLn did not possess the best uptake efficiencies despite their superior performance in the transfection studies. Their mean fluorescence intensities were 2571±90 and 3423±115, respectively, while those of SHCLn and SCLn were 4414±413 and 4066±185. The results also show that better cellular uptake was achieved when di-unsaturated linoleic acids were incorporated into the hydrophobic domains in place of mono-unsaturated oleic acid tails (reference the above ECO/ECLn MFIs as an example). In addition, spermine-based agents showed a significantly higher uptake than their EDA counterparts (EHCOMFI=1957±208 as opposed to SHCO MFI=3580±244).

Intracellular siRNA Release

Figure 8:
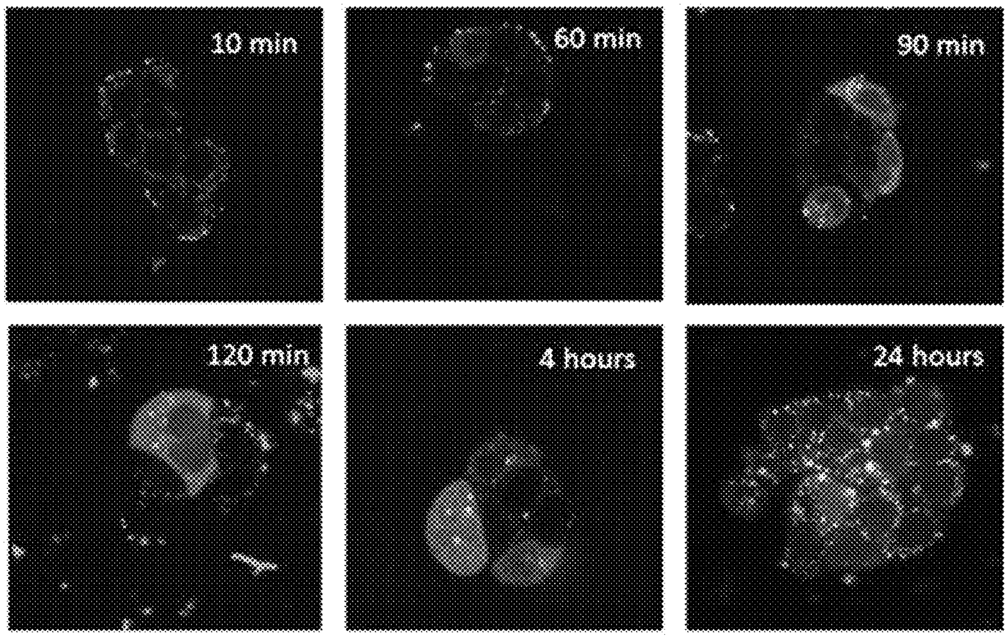
FIG. 8 illustrates confocal images showing that the ECO delivery system is able to promote intracellular dispersion of siRNA throughout the cytosol (labeled green with Alexa Fluor-488), preventing degradation within lysosomes (labeled red with Lysotracker Red-DND99). This is evident by the minimal co-localization seen, beginning at the 60 min time point.

Confocal microscopy was utilized to perform a time course study that analyzed the uptake and intracellular release kinetics of siRNA using the ECO delivery platform. Intracellular release and dispersion of siRNA is essential in RNA interference since the RNAi machinery Table 2 is found primarily in the cytosol. ECO-siRNA nanoparticles were prepared in the same manner that was implemented for the reporter knockdown studies, with the exception that the siRNA was now labeled with a fluorophore. FIG. 8 reveals that the ECO lipoplexes facilitated the escape of its siRNA payload from the endocytic pathway within the first 90 min after transfection, avoiding lysosomal entrapment degradation. This was evident by the lack of co-localization between the Alexa Fluor 488-labeled siRNA and the LysoTracker Red stain. siRNA dispersion was present in almost all cells 24 h post-transfection. Such results are in congruence with the hemolytic activity data demonstrating the membrane disruptive property of ECO in low pH environments, which is required for siRNA to escape from both endosomes and early lysosomes.

In the non-cancerous CHO cell line, each carrier was able to achieve significant knockdown of a GFP reporter protein as the N/P ratio was increased above 4. Little to no silencing by almost all of the transfection agents was observed at this formulation, likely stemming from the fact that their negative zeta potentials cause an electrostatic repulsion with the negatively charged cellular membranes. Five out of the eight agents induced at least 80% knockdown at N/P=12, while the remaining 3, including the original carrier EHCO, exhibited silencing efficiencies that paralleled those of Lipofectamine RNAi Max 72 h after transfection. The N/P=12 formulation was determined to be optimal for CHO cell transfection since it facilitated the greatest levels of GFP knockdown without significantly compromising cellular viability, as determined by MTT assay. In addition, the lipid carriers exhibited superior longterm effectiveness over Lipofectamine, as evidenced by the lack of increase in GFP expression of transfected CHO cells at both 48 and 72 h post-transfection.

Transfections with the HT29 colon cancer cells were not as robust compared to those conducted with the CHO line. The optimal N/P ratio was 18 when transfecting the HT29 cells, meaning that more carriers were required to facilitate the luciferase silencing. Nevertheless, none of the delivery agents were able to silence the reporter at the levels observed during the CHO-GFP study. The two best carriers were ECO and ECLn, which were able to achieve 77.5±3.3% and 76.5±5.1% knockdown 72 h post-transfection. Both agents performed significantly better than the parent compound EHCO, with a transfection efficiency of only 46.4±5.8%. Although the reporter genes in each cell line were different, Lipofectamine was able to silence both reporters equally well under the same transfection conditions and formulations. This suggests that the variable efficacy of our pH-sensitive delivery system is largely cell-type dependent. RNAi therapy is greatly impacted by the ability of siRNA to be taken up by the cells during endocytosis, and then to subsequently escape the endosomal compartments before lysosomal degradation. Each phenomenon was investigated separately to understand and correlate how modifications in the cationic lipid delivery system affected the performance of each carrier in the HT29 transfection studies.

Hemolysis studies are commonly implemented in siRNA therapeutic research to assess the potential endosomolytic capabilities of new delivery systems at pH values that mimic endosomal trafficking. By incubating the lipid-siRNA nanoparticles with rat erythrocytes at different pHs, and observing the release of hemoglobin into the surrounding medium, it can be determined whether the delivery system is able to promote endosomal membrane disruption required to release the nucleic acid into the cytoplasm, where it can then locate RISC complexes and mediate mRNA degradation. FIG. 6 shows that all synthesized carriers exhibited significant improvement in membrane disruptive activity at pHs 6.5 and 5.4 (characteristic of early and late endosomes), than at pH=7.4 (extracellular) for N/P formulations between 5 and 15. In general, the hemolytic activity was not affected by the choice of fatty acid tail for the hydrophobic domain of the delivery system. However, increasing the number of amines in the head group improved hemolytic activity, as all spermine-based carriers performed better than their EDA-based analogs at pH=6.5 (i.e., SHCO/SHCLn was more efficient than EHCO/EHCLn, and SCO/SCLn was more efficient than ECO/ECLn). Lipid carriers with spermine in their head groups possess a greater number of positive charges after protonation in acidic environments. This can potentially improve their ability to electrostatically interact with anionic phospholipids in the red blood cell membrane and better promote bilayer destabilization.

However, the presence of additional protonable amines does not necessarily translate to better hemolytic activity. Although histidine possesses a protonable amine, lipid carriers containing this chemical moiety in their linker domain actually exhibited weaker membrane disruptive capabilities than their counterparts. At pH=6.5, EHCO and EHCLn both had lower hemolytic activity than ECO and ECLn, and the same discovery was made for SHCO/SHCLn and their SCO/SCLn counterparts. The incorporation of histidine into the delivery system likely reduces the overall pKa of the cationic lipids. As a result, the pH-sensitivity of the carriers will increase, and thus potentially reduce the ability of each agent to protonate and electrostatically fuse with the RBC membrane bilayers at this level of acidity. This suggests that the ECO and ECLn based nanoparticles may better fuse with the membranes of early endosomes (pH=6.5) than the parent EHCO complexes, and therefore contribute to their superior silencing efficiencies observed in the reporter knockdown studies. Nevertheless, a steric effect may also play a significant role in the weaker membrane disruptive behavior observed upon introduction of the histidine residue. Geometrical shape of the transfection agent potentially plays a role in membrane fusion during RNAi mediated therapies. Cone-shaped cationic lipids have the ability to interact with anionic phospholipids in the endosomal membrane and form ion pairs that adopt non-bilayer structures with the ability to induce bilayer disruption in these compartments. Histidine is an amino acid that contains an imidazole ring in its side chain. Including this chemical group into the linker for each hydrophobic tail can potentially increase the cross-sectional area of the hydrophilic portion of the lipid, favoring a more cylindrical shape that supports a bilayer structure. As evidenced by the fact that ECO, ECLn, SHCO, and SHCLn have similar hemolytic capabilities, it appears that the geometrical shape, the overall pKa, and the number of protonable amines in the lipid construct all appear to represent competing factors that determine the ability of our delivery system to facilitate membrane disruption in various pH environments. Ideally, these properties should contribute to the endosomal escape and intracellular dispersion mechanisms of therapeutic siRNA.

Cellular uptake of Alexa Fluor 488-labeled siRNA (100 nM) by HT29 colon cancer cells was measured by flow cytometry after a 4 hour incubation period with lipid nanoparticles formulated at N/P=18. It was demonstrated that cellular uptake mediated by the EHCO/EHCLn carriers was not as robust compared to that of SHCO/SCHLn, matching the same trend observed when using the ECO/ECLn and SCO/SCLn compounds. This finding suggests that the greater amine-rich head group is more favorable for passive uptake and delivery into cells, even though all siRNA-lipid nanoparticles possessed similar sizes (45-75 nm in diameter) and zeta potentials (25-30 mV). Incorporating histidine into the linker domain, and thus two additional protonableamines, actually reduced nanoparticle uptake for EDA-based carriers, but did not have a significant impact when spermine was utilized. This can be attributed to why ECO and ECL each possessed better cellular uptake kinetics than the parent EHCO transfection agent. Nonetheless, unlike the hemolysis study, it was determined that the degree of unsaturation did in fact play a role in cellular uptake properties. The greater uptake of siRNA using transfection agents with the di-unsaturated linoleic acid fatty acid tails can possibly be attributed to increased lipid fluidity, as other studies have found that this anisotropic feature can enhance fusion, and not membrane destabilization, with bi-layered liposomal vesicles.

Despite the fact that ECO and ECLn were the optimal carriers for the luciferase knockdown study in the HT29 tumor cells, they exhibited neither the greatest membrane disruptive nor the highest cellular uptake capacity in the in vitro experiments. ECO, for example, did not perform as well as SCO/SCLn at any pH in the hemolytic study, nor did it match their levels of cellular uptake. A similar observation can be made with SHCLn. Since ECO was still able to achieve better RNAi silencing effects of the luciferase reporter, it is possible that the intracellular trafficking mechanisms and pathways within the cell might not be the same for each carrier designed in the library, and is thus responsible for the lack of correlation in the trends observed from the endosomolytic/uptake data and the RNAi knockdown study. Similarly, it is also possible that the superior condensation properties of spermine-based carriers like SCO/SCLn, as evidenced by the encapsulation data, severely inhibited the rapid intracellular release of their siRNA payloads during endosomal membrane fusion. Progressively increasing the number of positive charges, or multivalency, of the head group may result in too strong of an interaction with siRNA, such that it significantly hampers their ability to dissociate inside the cell.

The confocal images shown in FIG. 8 reveal that ECO is able to facilitate efficient uptake and intracellular release of administered siRNA, as seen by the disperse Alexa Fluor 488-signal throughout the cell. The lack of co-localized signal with Lysotracker Red suggests that the nanoparticles are able to evade lysosomal degradation within 1 h post-transfection.

Example 2

We developed a library of pH-sensitive amphiphilic lipid carriers through solid-phase chemistry synthesis. Each of the carrier designs was constructed to have three distinct regions of varying composition: 1) a cationic head group; 2) cysteine-based functionalizable linkers; and 3) a lipophilic region consisting of geminal lipid tails. We have shown that the number of amino groups within the head group, the degree of unsaturation of the lipid tail groups, and the structure and composition of the linker group have a significant effect on various aspects of the delivery process, including cellular uptake and gene silencing efficiency. Among these carriers, ECO ((1-aminoethyl)iminobis[N-(oleicylcysteinyl-1-amino-ethyl)propionamide]) emerged as a lead multifunctional carrier for further development because of its effectiveness for mediating potent gene silencing in both cancerous and non-cancerous cells.

Figure 9:
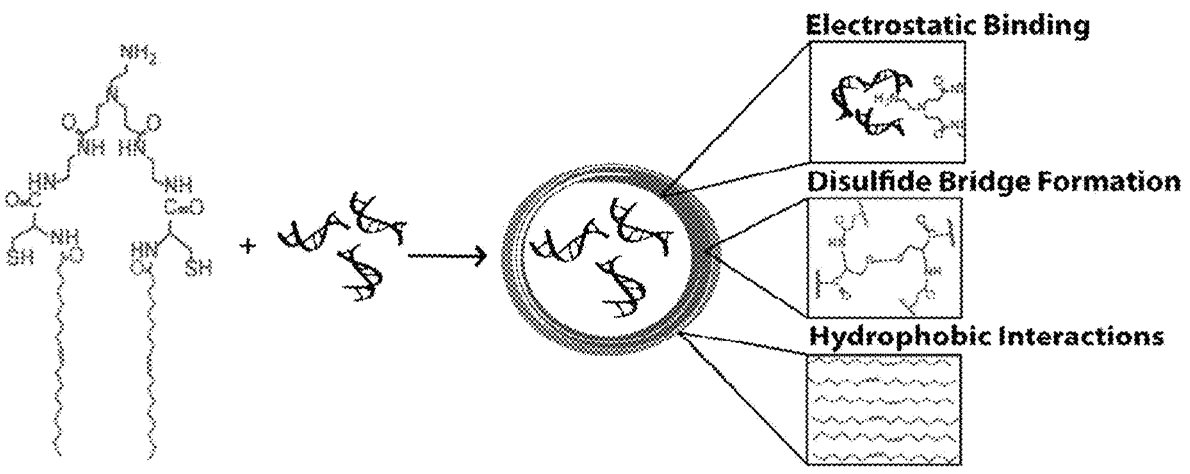
FIG. 9 illustrates a schematic drawing showing the formation of ECO/siRNA nanoparticles via electrostatic interactions between the cationic head group and anionic siRNA, auto-oxidation of free thiol groups within the cysteine residues to form disulfide crosslinks, and hydrophobic condensation of lipid tail groups.
Figure 10:
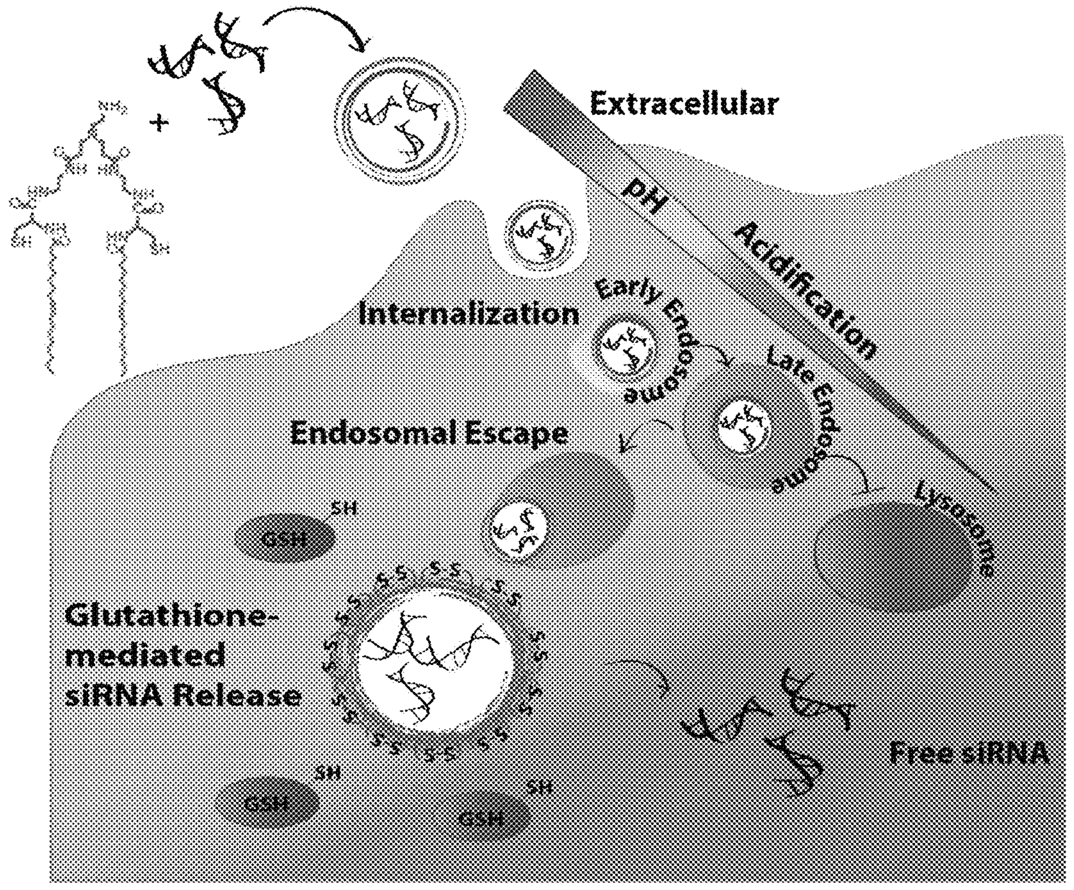
FIG. 10 illustrates a schematic drawing showing ECO/siRNA nanoparticles facilitate cellular internalization resulting in trafficking of the nanoparticles into the late endosomes. Within the late endosomes, the pH-sensitive nature of ECO promotes endosomal escape. Once release into the cytosol, endogenous glutathione (GSH) mediates reduction of disulfide bonds formed within ECO/siRNA nanoparticles to release the siRNA cargo. Upon release, free siRNA is able to initiate RNAi-induced gene silencing.

ECO is a cationic lipid containing three structural components hypothesized to play a significant role and function: a protonable ethylenediamine head group, two cysteine-based linker groups, and two oleic acid lipid tails (FIG. 9). The ethylenediamine head group allows for the electrostatic condensation of siRNA. The geminal oleic acid tails hydrophobically aggregate in an aqueous environment to further condense the nanoparticles. The free thiol groups of the cysteine residues can be autooxidized into reducible disulfide linkages to further stabilize the nanoparticles. Additionally, the cysteine residues can also provide a means to functionalize the carrier with targeting moieties and/or biocompatible polymers, e.g., polyethylene glycol (PEG), to improve biocompatibility and target-specific delivery. Finally, the structure possesses pH-sensitive amphiphilicity, an essential ability for disrupting the membrane of endosomal and lysosomal compartments to promote escape and avoid degradation of the siRNA cargo within the acidic environment. Upon successful escape, the disulfide bonds within the nanoparticle backbone are designed to facilitate the release of siRNA in the reductive environment of the cytosol (FIG. 10).

In this Example, we provide a comprehensive evaluation of the multifunctional properties of ECO as a carrier for effective intracellular siRNA delivery. ECO/siRNA nanoparticles were formed and characterized over a range of N/P ratios. The physicochemical properties of the ECO/siRNA nanoparticles, including serum stability, pH-sensitivity, and bio-reducibility, were determined in correlation with intracellular siRNA delivery and gene silencing efficiency. Further, the process of endosomal escape and mechanism of intracellular siRNA release following cellular uptake of ECO/siRNA nanoparticles was investigated in order to understand their gene silencing ability in U87 glioblastoma cancer cells. The response to environmental stimulus, coupled with the superior gene silencing and serum stability, is of particular interest and utility in overcoming the delivery barriers against nanoparticle-mediated gene therapy.

Methods

Preparation of ECO/siRNA Nanoparticles

The ECO lipid carrier was synthesized as previously reported. 19 ECO/siRNA nanoparticles were prepared at N/P ratios between 6 and 20. ECO and siRNA were diluted into equal volumes in nuclease-free water from stock solutions of 2.5 mM in ethanol and 18.8 μM in nuclease-free water, respectively. The equal volumes of ECO and siRNA were mixed followed by a 30-minute incubation period at room temperature under gentle agitation.

Nanoparticle Characterization

The size and zeta potential of the ECO/siRNA nanoparticles at different N/P ratios in PBS was determined by dynamic light scattering with a Brookhaven ZetaPALS Particle Size and Zeta Potential Analyzer (Brookhaven Instruments). Zeta potential measurements were repeated for nanoparticles incubated for 30 minutes in serum free, 10% and 50% serum media. To determine the pH-sensitivity of ECO, ECO/siRNA nanoparticles were formulated and incubated in PBS solutions at pH 7.4, 6.5, or 5.4 for 30 minutes prior to zeta potential measurement.

Entrapment Efficiency

A Ribogreen assay (Molecular Probes) was used to quantify the entrapment efficiency of siRNA within the ECO/siRNA nanoparticles. ECO/siRNA nanoparticles were prepared at various N/P ratios at a final siRNA concentration of 120 nM. Free siRNA following particle formation was detected using a SpectraMax microplate reader (Molecular Devices) with an excitation of 500 nm and emission of 525 nm. The entrapment efficiency of ECO/siRNA nanoparticles was calculated in reference to a linear standard curve by dividing the complexed siRNA concentration by the initial siRNA concentration and multiplying by 100%.

Heparin Displacement Assay

ECO/siRNA nanoparticles were prepared at an N/P ratio of 20 at a final siRNA concentration of 120 nM and incubated for 30 minutes at 37° C. with heparin solutions of varying concentrations based on heparin/siRNA (w/w) ratio, i.e., 0, 1, 2.5, 5. Following the incubation period, each sample, after the addition of loading dye, was run on a 1% agarose gel containing ethidium bromide at 100 V for 25 minutes.

Gel Electrophoresis for siRNA Loading, Serum Protection, and Glutathione-Mediated Nanoparticle Reduction The ability of ECO to complex and condense siRNA was assessed by gel electrophoresis. ECO/siRNA nanoparticles were prepared and 15 μL aliquots mixed with 3 μL of loading dye (Promega) were loaded onto a 1% agarose gel containing ethidium bromide. The gel was submerged in 0.5× Tris/Borate/EDTA (TBE) buffer and run at 100 V for 25 minutes. Free siRNA was run as the control. SiRNA bands were visualized using an AlphaImager ultraviolet imaging system (Biosciences). For siRNA loading, ECO/siRNA complexes were prepared at N/P ratios between 6 and 20 and run on the gel as described above. For the assessment of glutathione-mediated nanoparticle reduction, ECO/siRNA nanoparticles were incubated with 1 hour at 37° C. in the presence of 5 mM glutathione (GSH) (Sigma Aldrich). Following incubation, samples were loaded onto a 1% agarose gel containing ethidium bromide and run in the same manner as described. Serum protection of siRNA by the complexes was assessed by incubation ECO/siRNA complexes in 50% serum at 37° C. for 0.5, 1, 6, or 24 hours. At each intermittent time point, aliquots were taken and stored at −80° C. After the final aliquot was taken at 24 hours, samples were incubated for 30 minutes with heparin at a heparin/siRNA (w/w) ratio of 5 to release the complexed siRNA cargo and each sample was loaded on the 1% agarose gel and run as described above. Free siRNA was also incubated in 50% serum for 0.5, 1, 6, or 24 hours and stored and run on the gel in a similar manner Cell Culture Human glioblastoma U87 cells expressing a luciferase reporter enzyme (U87-Luc) were obtained from ATCC (American Type Culture Collection) and cultured in Dulbecco's modified Eagle's media (Invitrogen) and supplemented with 10% fetal bovine serum (Invitrogen), 100 μg/mL streptomycin, and 100 unites/mL penicillin (Invitrogen). The cells were maintained in a humidified incubator at 37° C. and 5% $CO_2$.

In Vitro Transfection Efficiency

U87-Luc cells were seeded in 24-well plates at a density of $2\times10^4$ cells and allowed to grow for 24 hours. Transfections were carried out in serum-containing (10% or 50% FBS) and serum free media with 40 nM anti-luciferase siRNA concentration (Dharmacon: sense sequence: 5'-CUUACGCUGAGUACUUCGAdTdT-3', anti-sense sequence: 5'-UCGAAGUACUCAGCGUAAGdTdT-3'). Following a 4 hour transfection period, the media was replaced with fresh serum-containing media and the cells continued to grow for an additional 72 hours. At 72 hours, the cells were rinsed twice with PBS and lysed using the reporter lysis buffered provided in the Promega Luciferase Assay kit. Following lysis, the cells were centrifuged at 10,000 g for 5 minutes and 20 μL cell lysate was transferred to a 96-well plate. To quantify luciferase expression, 100 μL Luciferase Assay Reagent was added to each well and the luminescence was read using a SpectraMax microplate reader (Molecular Devices). Luciferase activity was normalized to the total protein content measured from the cell lysate of each well using the BCA assay (Thermo Scientific). Data was presented relative to the control, which received no siRNA treatment. Lipofectamine RNAiMAX was used as a positive control and was prepared per the manufacturer's protocol (Life Technologies).

Cytotoxicity

U87 were transfected in 10% serum media with ECO/siRNA nanoparticles at a siRNA concentration of 40 nM in a 96-well plate with a seeding density of $1\times10^4$ cells. After 48 hours, the MTT reagent (Invitrogen) was added to the cells for 4 hours followed by the addition of SDS-HCl and further incubation for 4 hours. The absorbance of each well was measured at 570 nm using a SpectraMax spectrophotometer (Molecular Devices). Cellular viability was calculated as the average of the set of triplicates for each N/P ratio and was normalized relative to the no treatment control.

Flow Cytometry for Nanoparticle Cellular Uptake and Uptake Kinetics Measurements Cellular uptake and intracellular delivery of ECO/siRNA nanoparticles was evaluated quantitatively with flow cytometry. ECO/siRNA nanoparticles were prepared with 40 nM AlexaFluor488-labelled siRNA (Qiagen). Approximately $2.5\times10^4$ U87 cells were seeded onto 12-well plates and grown for an additional 24 hours. The cells were transfected with ECO/siRNA nanoparticles in serum free, 10% or 50% serum media. After 4 hours, the transfection media was removed and each well was washed twice with PBS. The cells were harvested by treatment with 0.25% trypsin containing 0.26 mM EDTA, (Invitrogen) collected by centrifugation at 1000 rpm for 5 min, resuspended in 500 μL of PBS containing 5% paraformaldehyde, and finally passed through a 35 μm cell strainer (BD Biosciences). Cellular internalization of ECO/siRNA nanoparticles was quantified by the fluorescence intensity measurement of Alexa Fluor 488 fluorescence for a total of 10,000 cells per each sample using a BD FACSCalibur flow cytometer. Each N/P ratio was conducted in triplicate and the data presented represents the mean fluorescence intensity and standard deviation.

Nanoparticle uptake kinetics was measured in a similar setup as described above. ECO/siRNA nanoparticles were formulated with 40 nM Alexa Fluor 488-labelled siRNA at an N/P ratio of 10. U87 cells were seeded in 24-well plates at a density of $2\times10^4$ cells and allowed to grow for 24 hours. Nanoparticles were administered in serum free, 10% or 50% serum media. Nanoparticle uptake was measured at various time points up to 4 hours post-transfection. At each time point, the cells were washed twice with PBS, trypsinized, collected and fixed with 5% paraformaldehyde in PBS before quantification of Alexa Fluor 488 fluorescence using a BD FACSCalibur flow cytometer. The mean fluorescence of 10,000 cells was quantified for each replica. Data presented represents the mean and standard deviation of three replicas for each time point.

Protein Adsorption

ECO/siRNA nanoparticles were formulated at an N/P ratio of 10. To quantify BSA protein adsorption, 500 μL of nanoparticle solution and 500 μL of BSA solution at varying concentrations were added together, stirred and incubated for 1 hour at 37° C. Nanoparticles were prepared such that the final amine concentration for each condition was 150 μM. Serial dilutions of a stock BSA solution (4 mg/mL) were carried out to achieve the various protein concentrations: 2 mg/mL, 1 mg/mL, 0.5 mg/mL, 0.25 mg/mL, 0.125 mg/mL. Following incubation, the ECO/siRNA nanoparticles were centrifuged at 10,000 g for 20 minutes. The concentration of BSA was determined from the supernatant using UV-Vis spectroscopy on a SpectraMax spectrophotometer (Molecular Devices) at 280 nm. A linear calibration curve from predetermined BSA concentrations was used. Relative BSA adsorption was calculated by dividing the amount of protein adsorbed for each BSA incubation concentration by the amount of protein adsorbed for 0.125 mg/mL BSA.

pH-Dependent Membrane Disruption Hemolysis Measurement

The hemolytic activity was measured to determine the membrane-disruptive ability of ECO/siRNA nanoparticles at pH levels corresponding to various stages of intracellular trafficking. Red blood cells (RBCs) isolated from rats (Innovative Research Inc.) were diluted 1:50 in PBS solutions at pH 7.4, 6.5, and 5.4. ECO/siRNA nanoparticles were prepared at a volume of 100 μL and incubated with an equal volume of the various RBC solutions in a 96-well plate at 37° C. for 2 hours. Nanoparticles were prepared such that the final amine concentration for each pH condition was 150 μM. Following incubation, samples were centrifuged and the absorbance of the supernatants was determined at 540 nm. Hemolytic activity was calculated relative to the hemolytic activity of 1% Triton X-100 (Sigma Aldrich), a non-ionic surfactant. Each pH was conducted in triplicate and the data presented represents the mean and standard deviation.

Inhibition of Glutathione-Dependent Reduction with BSO

Intracellular glutathione (GSH) was depleted in order to establish the role of cytosolic reduction of ECO/siRNA nanoparticles on gene silencing. U87 cells were plated and prepared in the same manner as during transfection studies. The cells were incubated overnight with 200 μM buthionine-sulfoximine (BSO) obtained from Sigma Aldrich prior to transfection, which was carried out as describe earlier with an N/P ratio of 10 and an anti-luciferase siRNA concentration of 40 nM. Luciferase expression was quantified with a luciferase assay and normalized with a BCA assay 48 hours post-transfection as described above.

Confocal Microscopy of Cellular Uptake of ECO/siRNA Nanoparticles and Intracellular Release of siRNA Live cell confocal microscopy was used to assess the cellular uptake and intracellular release of siRNA. Approximately 1×105 U87 cells were seeded onto glass-bottom micro-well dishes. After 24 hours, the cells were stained with 5 Pg/mL Hoechst 33342 (Invitrogen) and treated with ECO/siRNA nanoparticles in 10% serum media. Nanoparticles were formed at an N/P ratio of 10 and a 20 nM siRNA concentration with an Alexa Fluor 488-labelled siRNA. Images were taken using an Olympus FV1000 confocal microscope for up to 72 hours while the cells were housed in a humidified weather station under 5% $CO_2$.

Immunofluorescence of Intracellular Trafficking of ECO/siRNA Nanoparticles

Following transfection with ECO/siRNA particles containing Alexa Fluor 647-labelled siRNA (Qiagen), U87 cells were fixed at various time points with 4% formaldehyde for 30 min at room temperature and permeabilized with 0.1% Triton-X 100 (in PBS) for 5 minutes at room temperature. Cells were then incubated in blocking buffer (2% BSA in PBS) for 1 hour. The primary antibody, rabbit anti-lysosomal-associated membrane protein 1 (LAMP1) (Abcam), was added at 1 μg/mL in blocking buffer and incubated at room temperature for 1 hour. The secondary antibody, Alexa Fluor 488 goat anti-rabbit IgG (Life Technologies), was used at a 1:1000 dilution for 1 hour. Samples were thoroughly washed with PBS and imaged using an Olympus FV1000 confocal microscope.

Statistical Analysis

Experiments were performed in triplicate and presented as the mean and standard deviation. Statistical analysis was conducted with ANOVA and two-tailed Student's t-tests using a 95% confidence interval. Statistical significance was established only when $p<0.05$.

Effect of N/P Ratio on the Physicochemical Properties of ECO/siRNA Nanoparticles The physicochemical properties of siRNA nanoparticles can have a direct impact on the efficacy of intracellular siRNA delivery and gene silencing of the delivery system. The understanding of these physicochemical properties, including particle size, surface zeta potential, siRNA entrapment and particle stability, in correlation with the intracellular siRNA delivery and gene silencing efficiency is crucial for formulating a safe and effective siRNA delivery system suitable for clinical development. The physicochemical properties can be tailored based on the ratio of cationic and anionic charge (N/P ratio) within the ECO/siRNA nanoparticles. The impact of N/P ratio on these parameters was investigated for ECO/siRNA nanoparticles between an N/P ratio of 6 and an N/P ratio of 20.

Figure 11A:
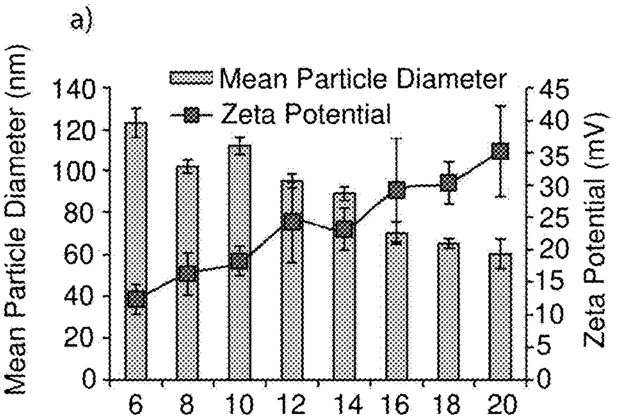
FIGS. 11(A-D) illustrate graph and immunoblots showing physicochemical evaluation of ECO/siRNA nanoparticles. A) Effect of N/P ratio on mean particle diameter and surface charge. B) siRNA entrapment within nanoparticles determined by RiboGreen RNA quantitation assay over a range of N/P ratios. C) Agarose gel retardation of ECO/siRNA nanoparticles compared to free siRNA over a range of N/P ratios. D) Heparin displacement assay. ECO/siRNA nanoparticles were prepared at N/P ratio of 20 and incubated for 30 minutes at 37° C. with varying amounts of heparin, based on heparin/siRNA (w/w) ratio.
Figure 11B:
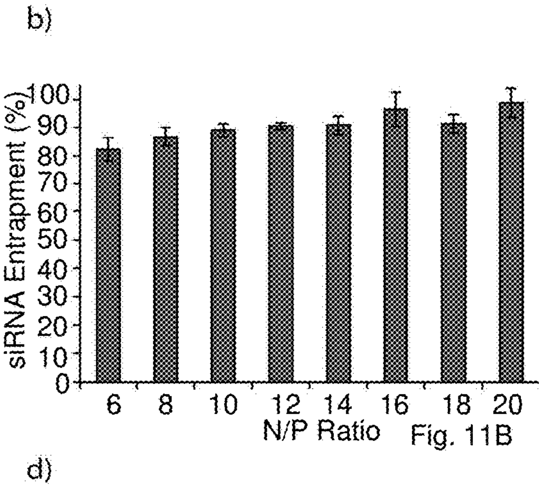
Figure 11C:
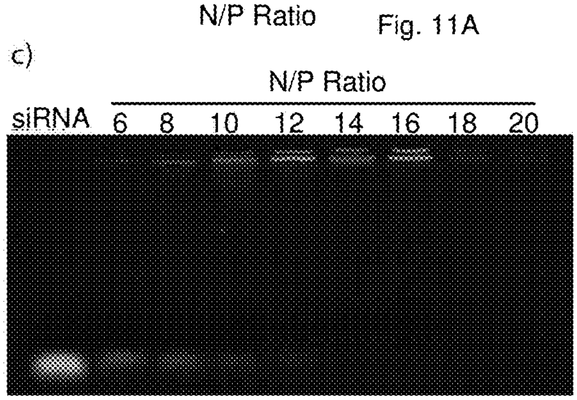
Figure 11D:
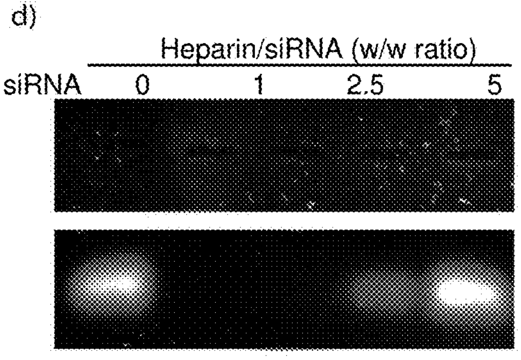

The particle size of ECO/siRNA nanoparticles decreased while their zeta potential increased as the N/P ratio increased (FIG. 11A). The ability of ECO to complex and entrap siRNA increased as a function of N/P ratio, from 82.1±4.3% at N/P=6 to 98.7±5.0% at N/P=20, as demonstrated by a RiboGreen fluorescence-based assay (FIG. 11B). The complexation of ECO with siRNA was further validated through an agarose gel retardation assay (FIG. 11C). Compared to naked siRNA, a decrease in particle-bound siRNA migration as the N/P ratio increased was observed. At an N/P ratio≥14, the complexed siRNA was completely prevented from migrating through the gel indicating that the interactions between ECO and siRNA were strong enough to resist dissociation during electrophoresis. Interestingly, at an N/P ratio≥18, no siRNA signal was observed in the loading well, suggesting that the negatively charged siRNA was completely neutralized as ethidium bromide was not able to intercalate. Some cationic polymers with high charge density, such as PEI, can form inseparable complexes with siRNA such that the siRNA cargo cannot be released once internalized into the cytosol. Therefore, it is important that the interactions between the siRNA and carrier be stable during cellular uptake but do not impede the cytosolic release of the siRNA. To study the electrostatic interaction of the siRNA with ECO, ECO/siRNA nanoparticles were subject to heparin displacement. Heparin is an anionic polysaccharide and a major component of extracellular matrix that can compete with siRNA for binding to disrupt ECO/siRNA complex stability. No decomplexation of siRNA from the nanoparticles occurred at heparin/siRNA (w/w) ratio of 1. Partial decomplexation of siRNA from the ECO/siRNA nanoparticles, as determined by siRNA release on an agarose gel, occurred at heparin/siRNA (w/w) ratio of 2.5 while full decomplexation was observed at a ratio of 5 (FIG. 11D).

These results suggest that the N/P ratio plays an essential role in regulating size, charge, and ability of the ECO lipid carrier to complex siRNA into stable nanoparticles. While particle size decreases, increasing the N/P ratio will increase the zeta potential. Increased concentrations of amino groups enhance the ability of ECO to condense the siRNA cargo by facilitating stronger ionic interactions and compact particle formation.

Effect of N/P Ratio on the Biological Properties of ECO/siRNA Nanoparticles

Figure 12A:
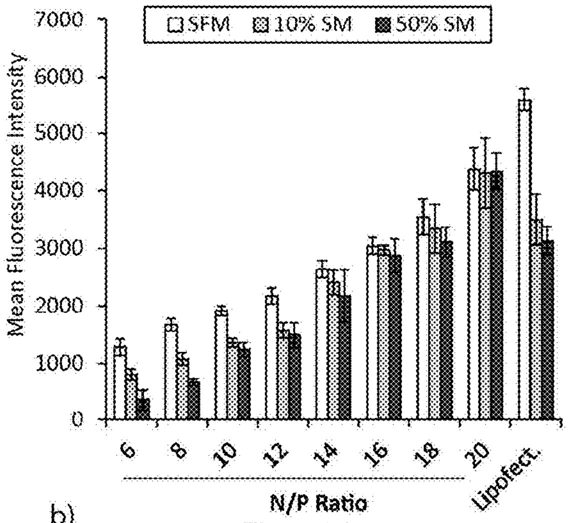
FIGS. 12(A-C) illustrate graphs showing biological activity of ECO/siRNA nanoparticles in U87 Glioblastoma cells. A) Cellular uptake quantified by flow cytometry for ECO/siRNA nanoparticles containing an Alexa Fluor 488-labelled siRNA in serum free (SFM), 10% serum media (10% SM), and 50% serum media (50% SM). Cellular uptake was found to be significantly higher in SFM for N/P ratios≤12 ($p<0.05$). B) Luciferase silencing efficiency of ECO/siRNA nanoparticles after 72 hours in serum free media, 10% and 50% serum media at 40 nM siRNA compared to Lipofectamine RNAiMAX (Lipofect). Quantified using a luciferase assay and normalized with a BCA assay. C) Cell viability assessed with an MTT assay in 10% serum media for ECO/siRNA nanoparticles.

The N/P ratio significantly influences the physicochemical parameters of ECO/siRNA nanoparticles, which can in turn influence the biological properties and activity of the nanoparticles. The effect of the N/P ratio on the cellular uptake, gene silencing and cytotoxicity of the siRNA nanoparticles was investigated in vitro with U87 glioblastoma cells expressing a luciferase reporter gene (U87-Luc). Cellular uptake of ECO/siRNA nanoparticles was determined using an Alexa Fluor 488-labeled siRNA with flow cytometry in serum-free, 10% serum, and 50% serum media (FIG. 12A). Cellular uptake was found to increase in an N/P ratio dependent manner for all transfection conditions. Under serum free conditions, Lipofectamine RNAiMAX (Lipofect) mediated higher cellular uptake than ECO for all N/P ratios. However, for 10% and 50% serum conditions, ECO/siRNA nanoparticles at an N/P of 20 had enhanced cellular uptake compared to Lipofectamine A significant reduction in cellular uptake was observed in 10% and 50% serum media for N/P ratios≤12 when compared to serum free media ($p<0.05$). At N/P≥14, cellular uptake in all three transfection conditions was not significantly different. As shown in the above study, high N/P ratios resulted in an increase in both surface zeta potential and stability of the nanoparticles (FIG. 12).

Figure 12B:
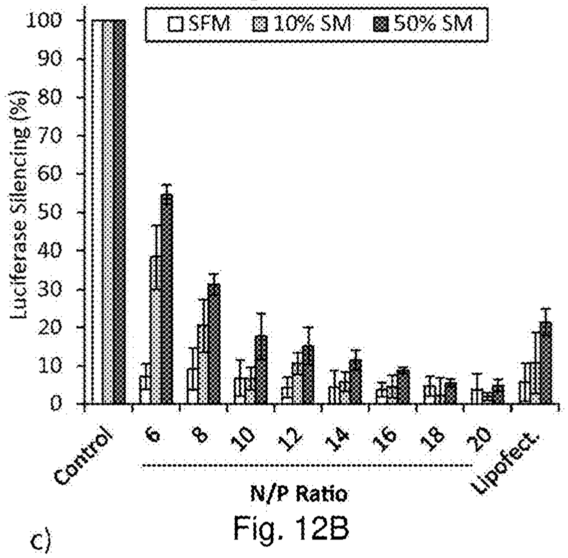

The gene silencing efficiency of ECO/siRNA nanoparticles was determined in U87-Luc cells using an anti-luciferase siRNA at 72 hours post-transfection in serum free, 10% and 50% serum transfection conditions. At a 40 nM siRNA concentration, gene silencing was dependent upon the N/P ratio, although this trend was more evident in the presence of serum (FIG. 12B). High gene silencing efficiency was observed for the nanoparticles throughout the N/P ratio range in serum free media:luciferase expression was inhibited to 7.2±3.4% for N/P=6 and 3.7±3.3% for N/P=20 at 72 hours post-transfection. In the presence of 10% serum, luciferase silencing increased in an N/P dependent manner from 38.41±8.19% luciferase expression for N/P=6 to 1.91±0.97% luciferase expression for N/P=20 at 72 hours. Similarly for 50% serum, luciferase silencing was less efficient for N/P ratios between 6 and 12 but was comparable to serum free and 10% serum for N/P≥12. At N/P≥10, ECO/siRNA nanoparticles matched or exceeded the performance of Lipofectamine RNAiMAX in their respective transfection conditions. It is interesting to note that in serum free media, ECO/siRNA nanoparticles were equally as efficient at silencing luciferase for N/P=6 as they were for N/P=20 despite a 4-fold difference in cellular uptake. One possible explanation may be that the RNAi machinery becomes saturated beyond a certain intracellular siRNA concentration. Alternatively, it has been suggested that the efficiency of siRNA delivery via lipid nanoparticles is limited by endocytic recycling, in which the siRNA nanoparticles within the endocytic vesicles are expelled from the cytosol back into the extracellular environment. For transfection conditions containing serum, gene silencing efficiency correlated with cellular uptake due to significantly lower cellular uptake at low N/P ratios compared to the serum free transfection condition.

Figure 12C:
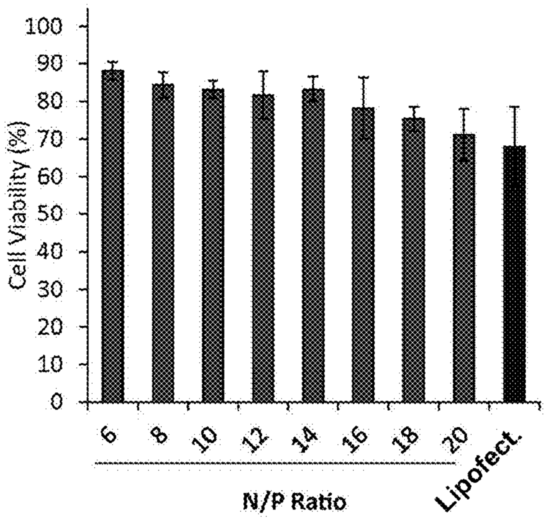

While a higher N/P ratio led to improved cellular uptake and gene silencing, unwanted cytotoxic effects may arise as a result and should therefore be monitored closely to ensure complete safety of a delivery system. The cytotoxicity of the ECO carrier was evaluated using an MTT assay (FIG. 12C). Cell viability was evaluated 48 hours post-transfection and was found to gradually decrease as the N/P ratio increased. Cell viability was especially compromised at N/P>14, which may be a result of increased positive charge densities at high N/P ratios. Importantly, the overall viability of those cells treated with ECO/siRNA nanoparticles at all N/P ratios remained higher than those treated with Lipofectamine RNAiMAX.

Increased cellular uptake may be a direct consequence of the zeta potential promoting interactions with the negatively charged cell membrane at high N/P ratios. However, increased zeta potential will negatively influence the biocompatibility of the delivery system. Additionally, low N/P ratios are not as efficient at inducing gene silencing in the presence of serum which may be in part contributed to reduced cellular uptake when compared to higher N/P ratios, but also due to their lower siRNA entrapment efficiency and lower stabilities. In an effort to optimize transfection conditions to maximize gene silencing while minimizing cytotoxic effects in U87 glioblastoma cells, an N/P ratio of 10 appeared to be the best formulation of the ECO/siRNA nanoparticles and was chosen for further studies. At an N/P of 10, ECO/siRNA nanoparticles averaged 112 nm in diameter, had a zeta potential of +18.2 mV, and silenced luciferase to 6.6% at 72 hours in 10% serum media while maintaining good cell viability.

Figure 13A:
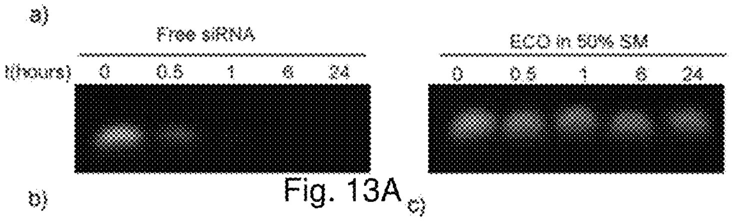
FIGS. 13(A-E) illustrate immunoblots, plots, and images showing: A) Susceptibility to serum-degradation of free or complexed siRNA within ECO nanoparticles. Samples were incubated in 50% serum for 0.5, 1, 6 and 24 hours. Glutathione (5 mM) was used to release complexed siRNA from ECO and the integrity of siRNA cargo was evaluated with an agarose gel electrophoresis assay. B) Kinetics of nanoparticle uptake with Alexa Fluor 488-labelled ECO/siRNA nanoparticles in U87 cells in serum free (SFM), 10% and 50% serum media (10% SM and 50% SM). Levels of cellular uptake of nanoparticles in SFM were found to be significantly higher than in 10% and 50% SM for all time points ($p<0.05$). C) ECO/siRNA nanoparticles were formulated at an N/P of 10 and the zeta potential was evaluated following incubation in either serum free, 10%, or 50% serum media. Zeta potential of nanoparticles was found to be significantly diminished by the presence of serum ($p<0.05$). D) Relative adsorption of bovine serum albumin (BSA) to the ECO/siRNA nanoparticles after 1 hour incubation at 37° C. as a function of BSA incubation concentration. E) Live-cell confocal imaging of cellular uptake of ECO/siRNA nanoparticles in U87 cells and cytosolic distribution of Alexa Fluor 488-labelled siRNA in 10% serum media. A dispersed siRNA-based fluorescent signal is present 4 hours post-transfection and remains upwards of 72 hours.

ECO/siRNA Nanoparticles Protect siRNA and Promote Cellular Uptake in the Presence of Serum Proteins Serum proteins may lead to dissociation of the siRNA nanoparticles, and premature release and degradation of siRNA. To address the question of nanoparticle stability and siRNA protection from nuclease degradation, free siRNA and ECO/siRNA nanoparticles (N/P=10) were incubated in PBS containing 50% fetal bovine serum at 37° C. for up to 24 hours. The agarose gel chromatogram of the siRNA in both formulations at various time points of the incubation revealed that free siRNA was prone to degradation within the first 30 minutes, and completely degraded by 6 hours, while siRNA within the ECO/siRNA nanoparticles was preserved for at least 24 hours (FIG. 13A). The result suggests that ECO is able to sufficiently complex and pack siRNA into stable nanoparticles such to protect the siRNA from enzymatic degradation in serum.

Figure 13B:
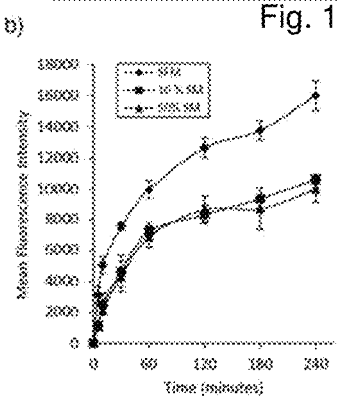
Figure 13C:
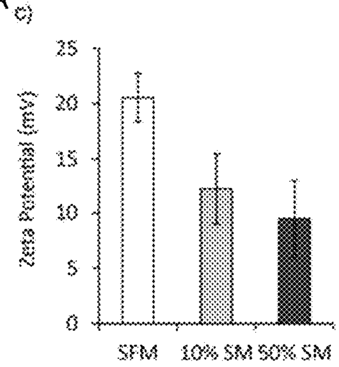
Figure 13D:
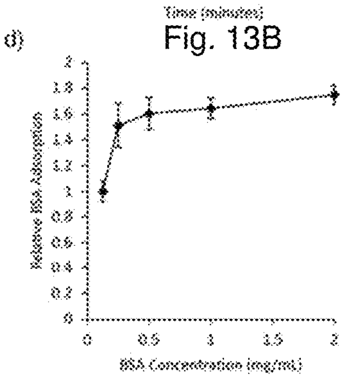

Non-specific interaction of serum proteins with the ECO/siRNA nanoparticles may also hinder membrane adsorption, block cellular entry, and diminish the transfection efficiency, as has been demonstrated previously with lipid-based nanoparticles. The kinetics of cellular uptake of nanoparticles complexed with an Alexa Fluor 488-labelled siRNA was monitored over the course of 4 hours in serum free, 10% and 50% serum media. While the nanoparticle uptake is clearly higher in serum free media than in 10% and 50% serum media ($p<0.05$), the cellular uptake under all transfection conditions exhibits a similar biphasic trend (FIG. 13B). This biphasic behavior has been speculated to originate from an initial period where nanoparticles adhere to the outer cell membrane before undergoing cellular entry and internalization.36 Initial membrane adhesion is associated with slow nanoparticle internalization until a steady state is achieved with a balanced rate of nanoparticle membrane adhesion and internalization. The lower siRNA-associated fluorescence signal observed in serum media was not due to siRNA degradation as the ECO nanoparticles were effective in protecting the cargo siRNA (FIG. 13A). The difference in cellular uptake may then be in part due to the non-specific interaction of serum proteins with nanoparticles and the consequent reduction of zeta potential, diminishing the ability of the nanoparticles to adhere to the outer cellular membrane and to undergo cellular internalization. This was confirmed (FIG. 13C) by the observation that ECO/siRNA nanoparticles had a reduced zeta potential in 10% and 50% serum media compared to serum free media ($p<0.05$). Cellular uptake and zeta potential was not found to be significantly different between 10% and 50% serum transfection conditions suggesting that serum protein binding to the ECO nanoparticles may reach a point of saturation. To determine this, the binding of bovine serum albumin (BSA), the major protein constituent of fetal bovine serum, to ECO/siRNA nanoparticles was quantified following incubation over a range of BSA concentrations (FIG. 13D). Indeed a saturation point of BSA adsorption was observed for BSA concentrations ≥0.25 mg/ml.

Figure 13E:
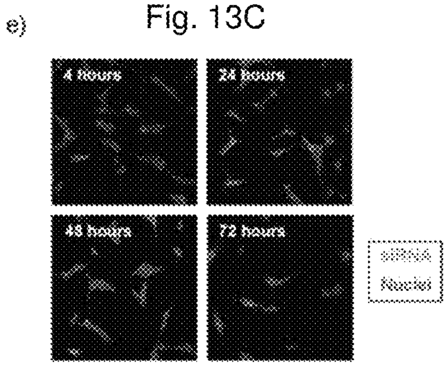

The cellular uptake of ECO/siRNA nanoparticles in the presence of serum was further investigated with confocal microscopy using an Alexa Fluor 488-labeled siRNA (FIG. 13*e*). Intracellular internalization and dispersed cytosolic siRNA distribution was observed as early as 4 hours post-transfection. In accordance with the observed sustained luciferase silencing (FIG. 12B), the dispersed signal intensity increased over time and persisted at least 72 hours post transfection. From these images, it is clear that even with a reduced zeta potential, ECO/siRNA nanoparticles were effectively taken up by the cells in serum and siRNA was released into the cytosol.

ECO/siRNA Nanoparticles are pH-Sensitive and Promote Endosomal Escape

Figure 14A:
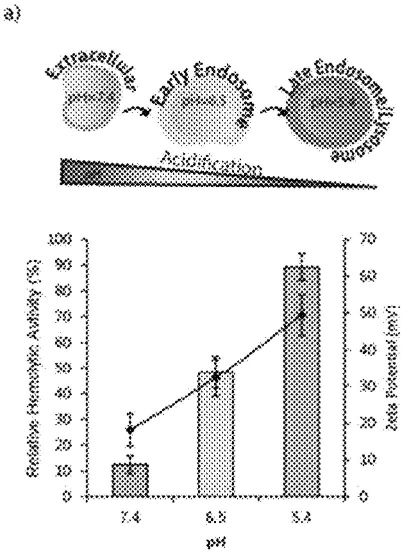
FIGS. 14(A-B) illustrate graphs and images showing: A) Zeta potential measurements following incubation in PBS at various pH levels demonstrate the pH-sensitivity of the ECO/siRNA nanoparticle. The zeta potential was found to increase with increasing acidity. Hemolytic assay determined the pH-dependent membrane disruptive ability of ECO/siRNA nanoparticles increased significantly ($p<0.05$) with increasing acidity (pH=7.4, 6.5, 5.4). Relative hemolytic activity calculated with respect to the hemolytic activity of 1% Triton-X-100. B) Immunofluorescence using an LAMP1-antibody (Alexa Fluor 488-labelled secondary antibody) to stain for late endosomes reveals co-localization of ECO/siRNA (Alexa Fluor 647-labelled siRNA) nanoparticles occurs 2 hours post-transfection. At 4 hours, a dispersed siRNA signal is present within the cytosol indicating that ECO/siRNA nanoparticles are able to escape from late endosomes and release the siRNA cargo.

Following successful internalization, one of the most crucial events for effective intracellular siRNA delivery is the escape from the endosomal-lysosomal pathway. It is imperative for the carrier to promote the escape from such pathways for the purpose that siRNA must be available within the cytosol to initiate RNAi. If the siRNA nanoparticles remain in these transport vesicles, they will be at risk to lysosomal degradation.39 It has been proposed that the multifunctional nanoparticles are able to escape endosomal-lysosomal pathways with their ability to disrupt the membrane of the acidic endosomes and lysosomes in a pH-sensitive manner. To validate this hypothesis, the zeta potential and membrane disruption ability of ECO/siRNA nanoparticles at pH levels of the extracellular (7.4) and endosomal and lysosomal environments (6.5 and 5.4) was studied. As the pH level decreased and became more acidic, amine groups within the cationic head group of ECO become protonated and consequently the zeta potential increased from 18.1 mV at pH=7.4, to 32.4 mV at pH=6.5, to 49.5 mV at pH=5.4 (FIG. 14A). The relative hemolytic activity of ECO/siRNA nanoparticles in rat blood cells (RBCs), normalized to the hemolytic activity of 1% Triton-X-100, was found to increase with acidity in a similar manner through which maturing endocytic vesicles are acidified (FIG. 14A). Hemolysis of 48.5±6.2% at pH of 6.5 and 89.2±5.4% at pH of 5.4 demonstrated the ability of these nanoparticles to interact with the membrane of late endosomes and/or lysosomes in response to the pH changes. The low hemolytic activity of ECO/siRNA nanoparticles at pH of 7.4 (12.5±3.5%) is consistent with the observation that ECO/siRNA nanoparticles elicit a low cytotoxic effect on cells, as minimal membrane disruption was observed.

Figure 14B:
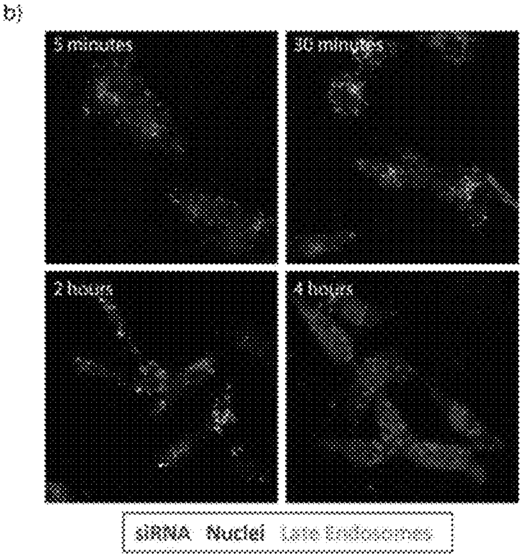

Intracellular trafficking of ECO/siRNA nanoparticles was further determined using fluorescence confocal microscopy based on the localization of an Alexa Fluor 647-labeled siRNA in respect to a specific marker for late endosomes and lysosomes (anti-LAMP1). As shown, the ECO/siRNA nanoparticles began interacting with the cell membrane with no visible co-localization with LAMP1-stained vesicles within the first 5 minutes of transfection (FIG. 14B). At 30 minutes, areas of co-localization of nanoparticles and late endosomes arose and colocalization increased at 2 hours, where the majority of the siRNA-based fluorescent signal is coalescent with the vesicles that are characteristic for late endosomes. By 4 hours, a dispersed siRNA signal distribution appeared and the co-localization of the siRNA with LAMP1 was diminished. This data suggests that the ECO/siRNA nanoparticles were trafficked through the endosomal-lysosomal pathway to the late endosomes, whereupon they were able to escape from the vesicles to release their cargo in the cytosol. Although the exact pathways responsible for internalization and trafficking of the nanoparticles have yet to be explored and defined, it has recently been suggested that most nano-sized particles are trafficked to the lysosomes regardless of their method of endocytosis. The result here suggests that, irrespective of the endocytic pathway, the multifunctional carrier ECO can promote effective early escape in the endosomal lysosomal pathway, a key feature responsible for its success in inducing gene silencing.

Figure 15A:
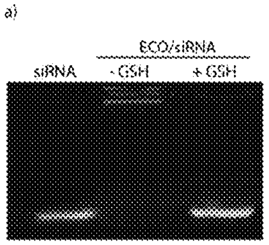
FIGS. 15(A-C) illustrate an immunoblot, graph, and images showing: A) Sensitivity of ECO/siRNA nanoparticles to reduction by endogenous levels of glutathione (GSH). Nanoparticles were incubated in the presence of 5 mM GSH for 1 hour at 37° C. Release of complexed siRNA was evaluated with an agarose gel electrophoresis assay. B) The ability of ECO/siRNA nanoparticles to induce luciferase silencing is inhibited by the pretreatment of U87 cells with BSO for 24 hours prior to transfection ($p<0.05$). C) Confocal imaging of cytosolic distribution of Alexa Fluor 488-labelled siRNA in U87 cells 4 hours post transfection. Compared to no treatment (left), pre-treatment with BSO for 24 hours (right) reduced cytosolic distribution of siRNA through inhibition of glutathione-mediated nanoparticle reduction.
Figure 15B:
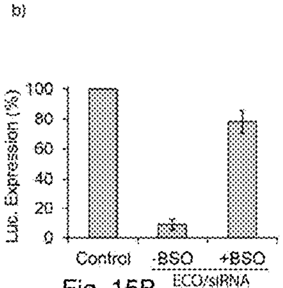
Figure 15C:
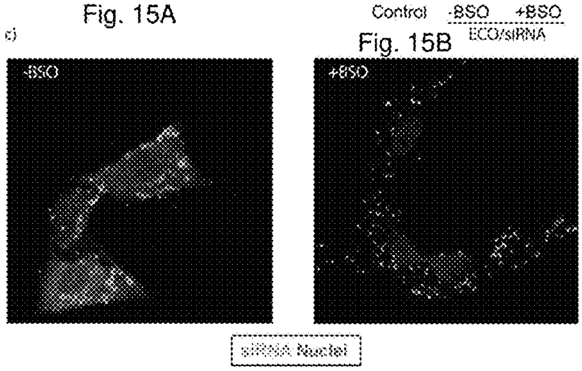
Figure 16A:
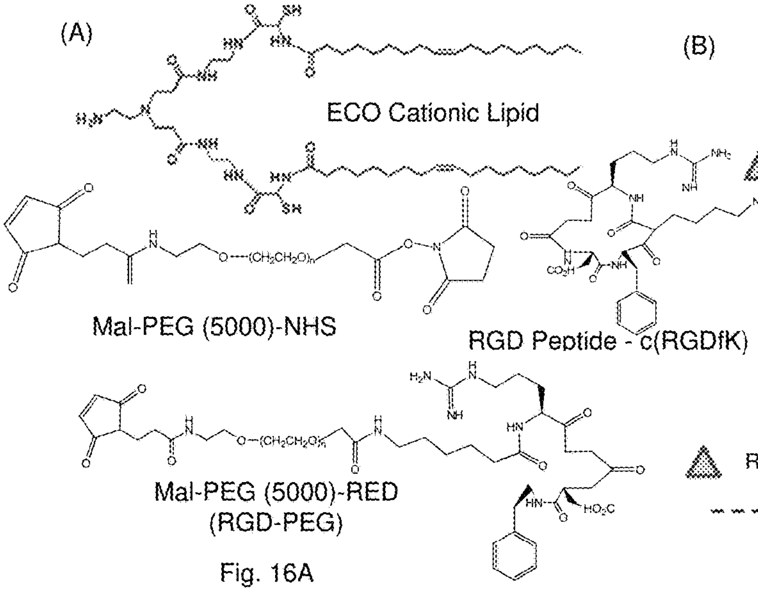
FIGS. 16(A-B) illustrate (A) chemical structures of the ECO cationic lipid carrier, the cyclic RGD peptide, and the hetereobifunctional Mal-PEG-NHS polymer used to construct the siRNA delivery platform; and (B) schematic of the final nanoparticle where the ECO/siRNA complexes are functionalized with targeting RGD-PEG conjugates.
Figure 16B:
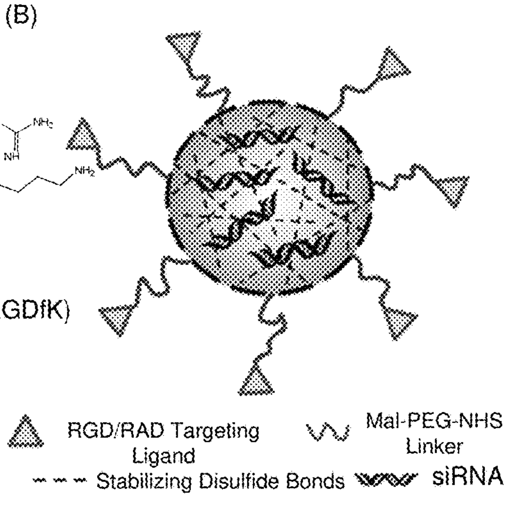

Cytosolic Reduction of ECO/siRNA Nanoparticles is Crucial for siRNA Release and RNAi Activity Once escaped from the endosomal-lysosomal pathway, the final step of the multi-stage process of intracellular siRNA delivery is to ensure the cytosolic release of the siRNA cargo whereupon it will be available to bind to the RNA induced silencing complex (RISC) and initiate RNAi. During nanoparticle formation, the ECO/siRNA nanoparticles are stabilized by disulfide bonds. The cleavage of these linkages within the reductive cytosolic environment, via disulfidethiol exchange initiated by endogenous glutathione, can facilitate the release of the complexed siRNA. This bio-reducible functionality of ECO was demonstrated by incubating nanoparticles at the physiological concentration of glutathione (5 mM) for 1 hour at 37° C. Agarose gel electrophoresis was used to evaluate whether the siRNA cargo could be released in the presence of the reducing agent. In the absence of glutathione, ECO successfully condensed siRNA into nanoparticles while in the presence of glutathione, the siRNA cargo disassociated from the nanoparticles, indicating that disulfide reduction by glutathione was sufficient to unpack the ECO/siRNA nanoparticles (FIG. 15A). To further demonstrate the significance of glutathione-dependent reduction of the nanoparticles for cytosolic release of siRNA and RNAi activity, U87-Luc cells were treated with buthionine sulfoximine (BSO) prior to transfection with ECO/siRNA nanoparticles. BSO was implemented to deplete intracellular glutathione by inhibiting γ-glutamylcysteine synthetase, the enzyme required to initiate glutathione synthesis. The ability of ECO/siRNA nanoparticles to silence luciferase expression was significantly inhibited by the BSO treatment (FIG. 15B). Confocal microscopy further revealed that pre-treatment of U87-Luc cells with BSO prevented the dispersed cytosolic distribution of siRNA 4 hours post-transfection (FIG. 15C). Unlike the dispersed siRNA-associated fluorescence observed in the cytosol of untreated cells (left), the fluorescence signal of the labeled siRNA in BSO-treated cells remained punctate, indicative of intact nanoparticles (right). The result demonstrate that the intracellular reduction of the nanoparticle, the final step in the arduous intracellular delivery process of siRNA, plays a vital role and is a requisite for achieving effective intracellular siRNA delivery and high gene silencing efficiency of ECO/siRNA nanoparticles. The inclusion of the cysteine residues within the structure of ECO is a key feature to stabilize the siRNA nanoparticles and for cytosol specific controlled siRNA release.

Example 3

Figure 17A:
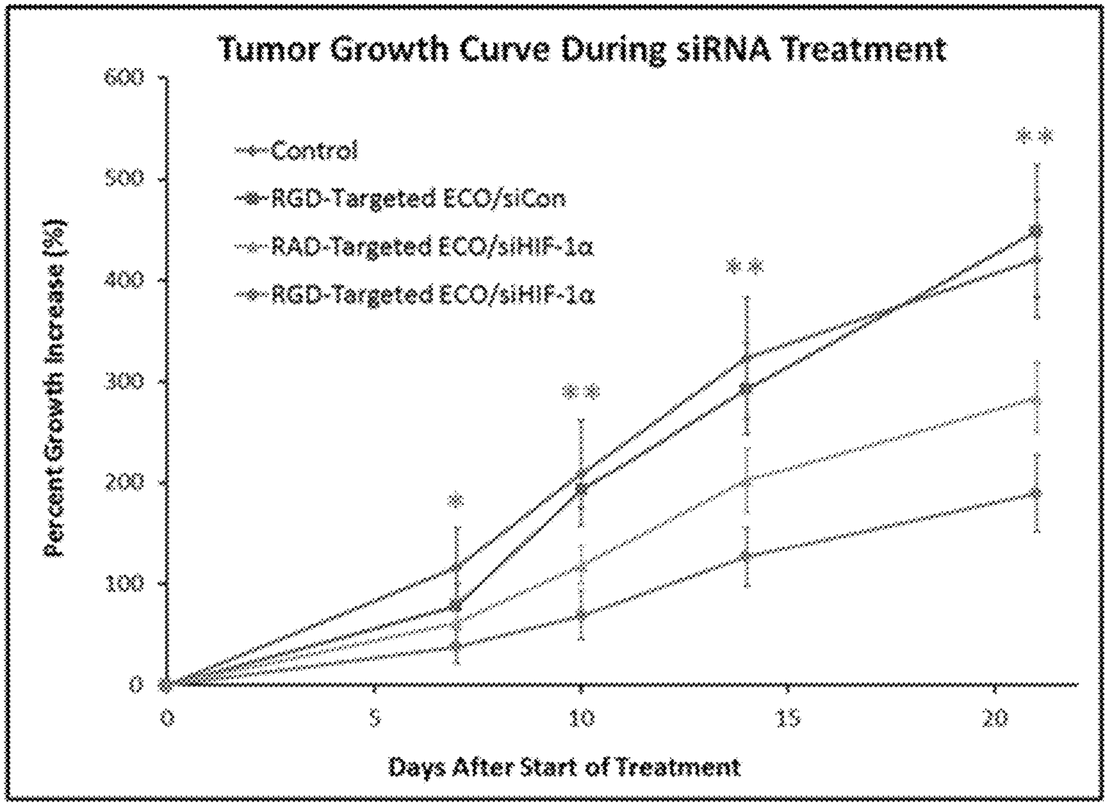
FIGS. 17(A-B) illustrates a plot and images showing ECO/siHIF-1α nanoparticles were targeted with either RGD or non-specific RAD peptides. The RGD-modified agents, which bind to $\alpha_v\beta_3$ integrins in the tumor vasculature, exhibited superior uptake and retention of AlexaFluor-647 labeled siHIF-1α in the tumor lesion 24 hours after intravenous injection (A). Both formulations showed the ability to significantly reduce tumor size over the 3 week treatment period in relation to the saline control group. However, starting at day 10 of the siHIF-1α treatment regimen, the RGD-functionalized agents outperformed their RAD analogs ($p=0.01$). By the end of the 3 week therapy, RGD-targeting was able to facilitate a 54.9% decrease in tumor size, as opposed to a 32.4% reduction by non-specific RAD-targeting ($p=0.006$). (* denotes $p<0.05$).

RGD-Targeting of RNAi Therapy Enhances Tumor Uptake and Reduction of Tumor Growth The therapeutic effectiveness of the ECO/siHIF-1α was tested by using four different groups of athymic nude mice, each bearing a subcutaneous flank HT29 colon tumor. Two groups were treated with siRNA nanoparticles carrying a siRNA transcript specific to HIF-1(siHIF-1α). However one set of complexes was actively targeted to $\alpha_v\beta_3$ integrins in the tumor endothelium using an RGD peptide sequence, while the other was non-specifically targeted to these integrins with a control RAD peptide (FIG. 10). The two remaining groups served as our controls. One group of mice was only treated with saline, and the last group was treated with RGD-targeted nanoparticles bearing a negative control siRNA (siCon) in order to test the specificity our siHIF-1α sequence. Treatments were intravenously administered to mice once every 3 days, until day 21 after the beginning of the siRNA treatment regimen. The tumor growth curves in FIG. 17*a* show that RGD targeting of siHIF-1α was able to significantly reduce the size of the primary lesion by 54.9% when compared to the saline control tumors at the end of the 3 week administration period. Although not as effective, RAD-targeting of ECO/siHIF-1α particles was also able to tumor growth, causing a 32.5% in size. As expected, the non-specific siCon sequence was not able to induce any significant changes in tumor growth.

Figure 17B:
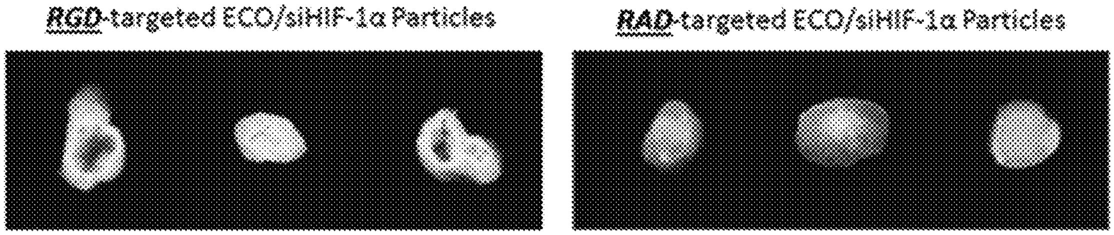

The targeting moieties that we utilized in this study were conjugated onto the ECO/siRNA constructs through the use of a heterobifunctional PEG linker, which is able to shield positive charges carried by the cationic lipid carrier. The use of PEG is known to increase circulation times in the body, and therefore effectively facilitate passive uptake into the tumor tissue even when non-specific RAD moieties are attached to the particles. However, the ability to deliver siRNA into tumors by passive techniques was significantly less than that achieved by active targeting with the RGD peptide. This is evident in the fluorescence images presented in FIG. 17*b*, showing significantly greater levels of AlexaFluor-labeled siRNA in resected tumors 24 hours after injection using RGD-targeted, as opposed to RAD-targeted, ECO nanoparticles. The significantly higher accumulation and retention of siRNA with RGD-targeted nanoparticles is most likely the reason for the difference observed in the tumor growth curve between these two formulations.

RNAi Therapy Successfully Silences HIF-1α and Reduces Ki67 Proliferation Index

Figure 18A:
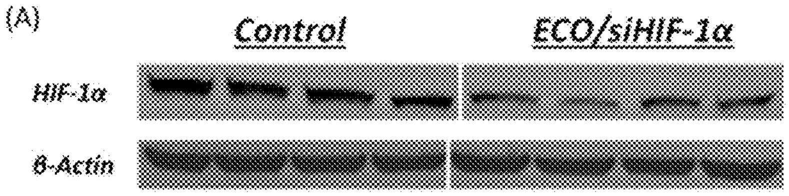
FIGS. 18(A-C) illustrate western blots and a graph showing that the ECO/siHIF-1α therapy causes a 52.7% decrease in HIF-1α expression when compared to the saline control therapy (A and B). These results were verified by IHC staining (C).
Figure 18C:
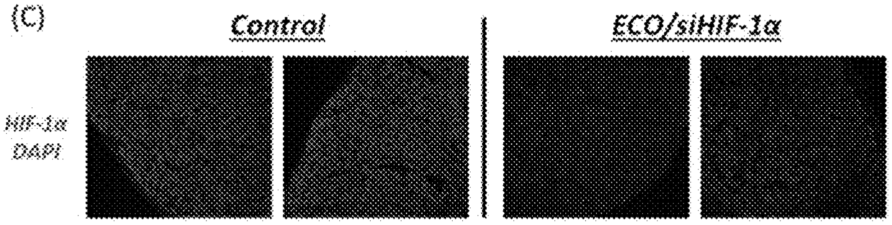
Figure 18B:
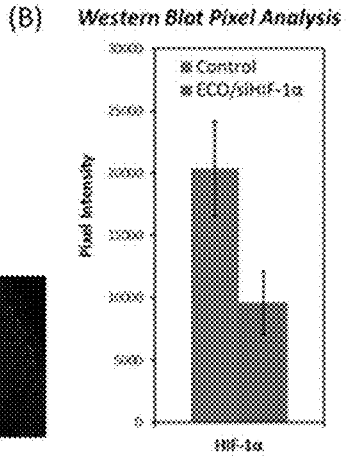

After completion of the RNAi therapy, all tumors from the control and the RGD-targeted ECO/siHIF-1α groups were removed for western blot and immunohistochemistry (IHC) analysis of HIF-1α protein expression. As expected, pixel analysis of western blots revealed that the RNAi therapy was able to significantly reduce expression of HIF-1α by 52.7%, suggesting that inhibition of this transcription factor played a major role in slowing the rate of HT29 tumor growth and proliferation (FIGS. 18A-B). These results were corroborated by a decrease in the signal intensity of IHC stains of this protein (FIG. 18C). Further investigation demonstrated that the anti-proliferative effects of HIF-1α inhibition were mediated by concurrent silencing of several downstream targets involved in glycolytic metabolism, pH regulation, and angiogenesis, all of which play a major role in supporting robust tumor proliferation and invasion.

Figure 19A:
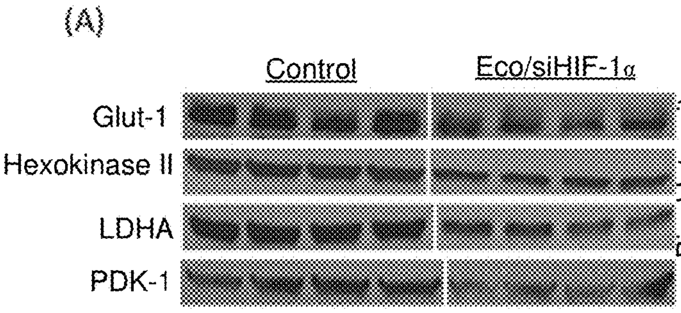
FIGS. 19(A-C) illustrate an immunoblots, a graph, and images showing the ECO/siHIF-1α therapy had significant effects on various players in the glycolytic pathway, causing significant reductions in Glut-1 (28.6%), HKII (36.4%), PDK1 (59.3%), and LDHA (41.5%). Such changes were supported by both western blot (A and B) and IHC staining (C), and may also play a role in the decline in tumor growth rate.
Figure 19B:
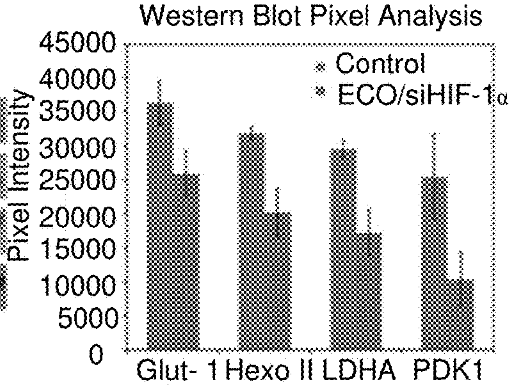
Figure 19C:
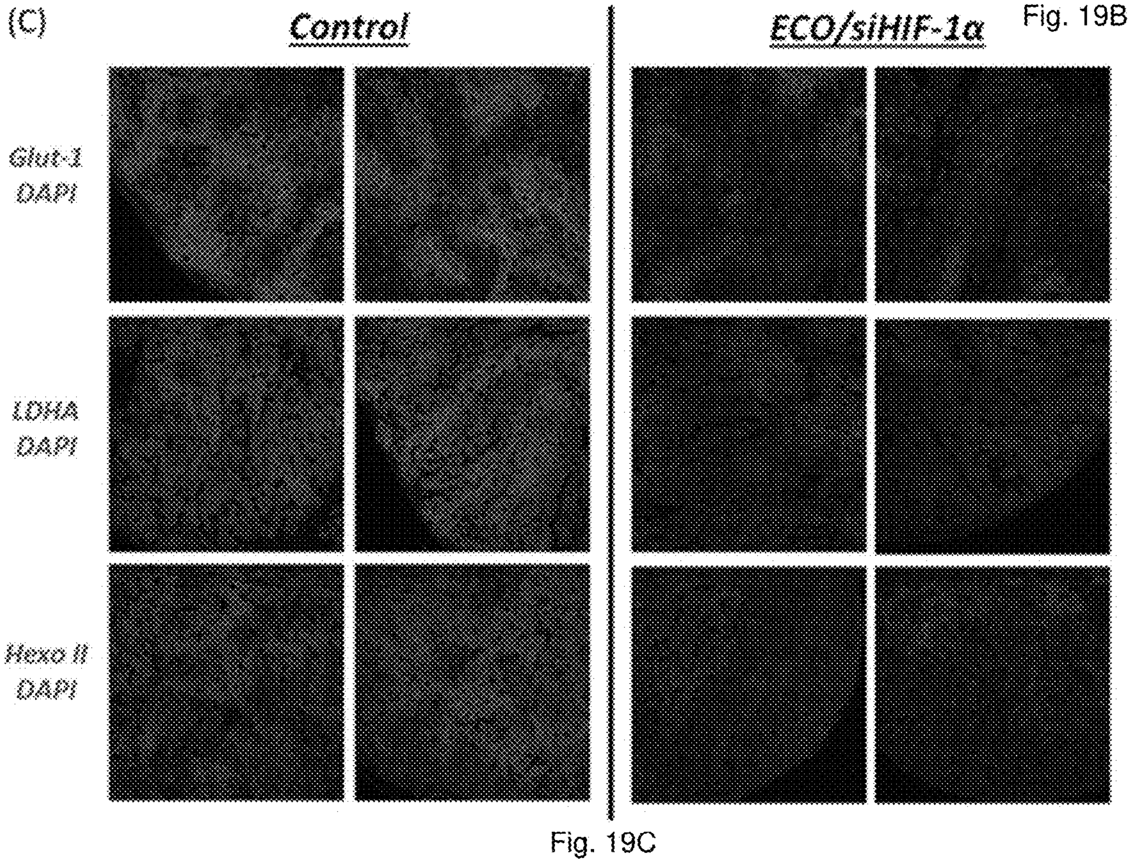
Figure 20A:
FIGS. 20(A-C) illustrate an immunoblot, graph, and images showing the expression of CAIX and MCT4 were significantly reduced by 53.9% and 50.2%, respectively, from the ECO/siHIF-1α therapy. Both are pH regulators, found in the cell membrane, that facilitate the extrusion of intracellular acid buildup from the metabolic pathway.
Figure 20B:
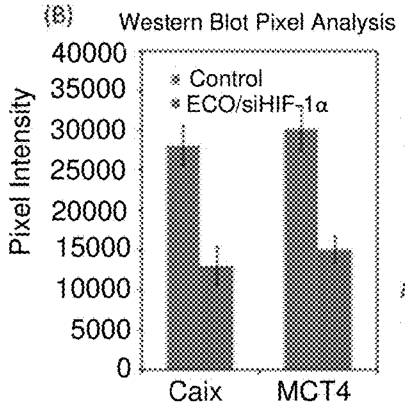
Figure 20C:
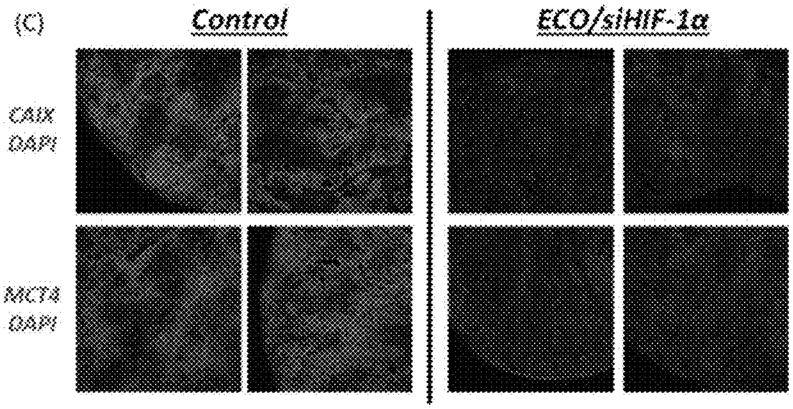

Inhibiting HIF-1α Expression Decreases Expression of Various Glycolytic and pH Regulators Glycolysis is an energy producing process by which cells oxidize glucose to rapidly generate ATP and meet the demanding metabolic needs of actively growing tumors. Since this form of metabolism generates ATP independently of oxidative phosphorylation, it ultimately results in the production and extrusion of lactic acid at the end of this pathway. Glycolytic metabolism is observed in a wide variety of tumors, serving as the primary source of energy in both aerobic and anaerobic environments to provide a selective growth advantage over normal cells that experience hypoxic changes in the tumor microenvironment. The change in expression of glucose transporter-1 (GLUT-1) and hexokinase II (HKII) in the glycolytic pathway were analyzed here, as both are known to be regulated by HIF-1α. Overexpression of GLUT-1 within the cell membranes enhances the rate of glucose uptake, which is subsequently metabolized by HKII-mediated phosphorylation to entrap it inside the cell. In response to the siHIF-1α therapy, GLUT-1 and HKII levels were reduce by 28.6% and 36.4%, respectively (FIG. 19). Pyruvate dehydrogenase kinase-1 (PDK-1) is another enzyme that is induced by HIF-1α expression, whose primary function is to divert metabolically-derived pyruvate away from entering the TCA cycle, allowing it to continue through the glycolytic pathway. At this point, the pyruvate is reduced into the lactic acid by lactate dehydrogenase-A (LDHA), generating NAD oxidizing agents that are then recycled further up the glycolytic pathway to preserve the normal flux of glucose metabolism. Lactic acid is then shuttled out of the cell by monocarboxylate transporter-4 (MCT4). Numerous studies have shown that these last two glycolytic mediators are also regulated by HIF-1α. Western blot analysis revealed that HIF-1α inhibition during the 3 week siHIF-1α therapy was accompanied by reductions in PDK-1 (59.3%) and LDHA (41.5%), as shown in FIG. 19. In addition, MCT4 also experienced a decline of 50.24% from the therapy, which can be seen in FIG. 20. IHC staining once again verified the western blot data. The reduction in all of the above glycolytic mediators can potential lead to the decrease in metabolic flux in the HT29 tumor cells, and thus contribute to the observed decrease in tumor proliferation.

HIF-1α is also known to promote transcription and expression of several pH regulators in order to prevent the intracellular buildup of acid in light of stimulating the glycolytic pathway. The ability to extrude acid also confers a selective growth advantage to tumor cells since the extracellular acid is toxic to normal cells. MCT4 is one way HIF-1α mediates pH regulation. Another method is through the up-regulation of carbonic anhydrase IX (CAIX), which maintains the flux of intracellular acid out of the cell in the form of $CO_2$. Analysis of protein expression uncovered a 53.9% reduction of this enzyme in response to the siHIF-1α therapy (FIG. 20), potentially hampering regular pH homeostasis in tumor cells en route to inhibiting tumor growth.

Silencing HIF-1α Reduces VEGF and CD31 Expression

Figure 21A:
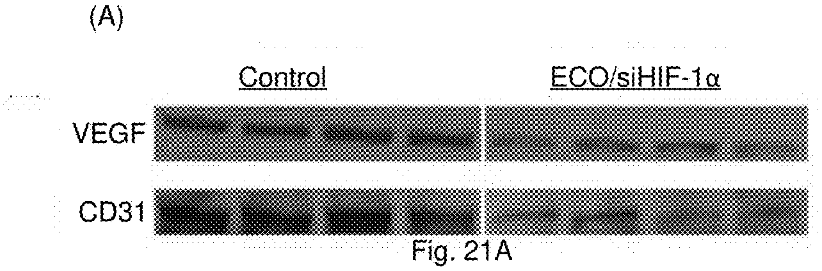
FIGS. 21(A-E) illustrates western blot analysis in (A) and (B) revealed that the VEGF pro-angiogenic factor and the CD31 blood vessel marker were significantly reduced following the ECO/siHIF-1α therapy (49.8% and 67.1% respectively). The decline in VEGF expression is shown in the IHC images of (C). The representative CD31 IHC stains presented in (D) are taken from both the tumor periphery and core in the siHIF-1α and saline treated mice. These images show that the control tumors have a more extensive vascular network than their siHIF-1α counterparts throughout the periphery and core parts of the tumor lesions. It is also evident that the cores of the siHIF-1α treated tumors are largely devoid of blood vessels, contributing to an increase in hypoxia, as exhibited by the pimonidazole stainings in (E).
Figure 21B:
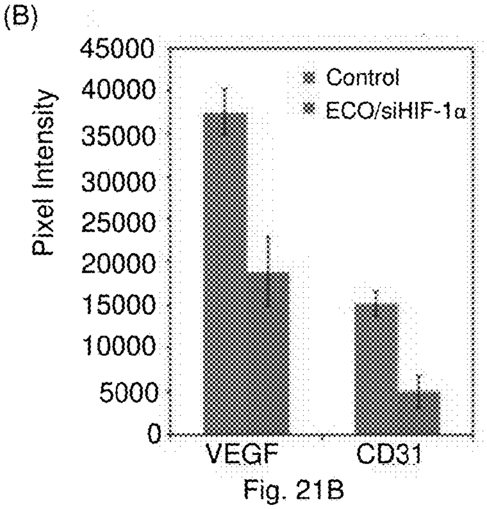
Figure 21C:
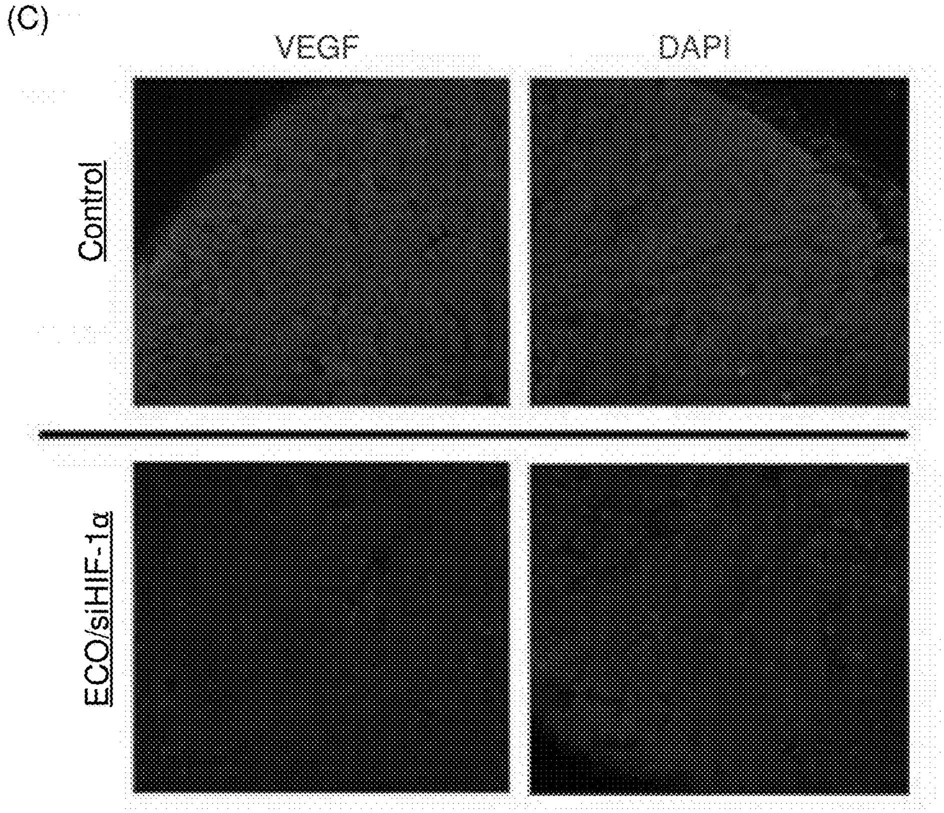

Tumor angiogenesis in initiated by the ability of HIF-1α to initiate the production and secretion of pro-angiogenic growth factors into the tumor microenvironment. Expansion of the vascular network is essential in order to efficiently delivery nutrients and oxygen to the tumor in support of its rapid proliferation. The anti-angiogenic effects of the ECO/siHIF-1α therapy were evaluated in several different ways. We first analyzed the expression of vascular endothelial growth factor (VEGF), one of the most prominent pro-angiogenic factors secreted by tumor cells under HIF-1α control. Western blot measurements revealed a 49.8% reduction in this factor, suggesting that the vascular network may be somewhat compromised in the siHIF-1α treated tumors (FIGS. 21A-B). This discovery was supported by the analysis of CD31, a glycoprotein expressed on blood vessels that is commonly used as a biomarker to monitor changes in the vascular network. CD31 protein expression was found to be significantly reduced by 67.1% after the siHIF-1α treatment (FIG. 21A-B). This difference was verified by IHC analysis, showing that the control tumors possessed greater vascular densities than their siHIF-1α counterparts, thus demonstrating that the RNAi therapy effectively triggered vascular regression (FIG. 21D).

Figure 21E:
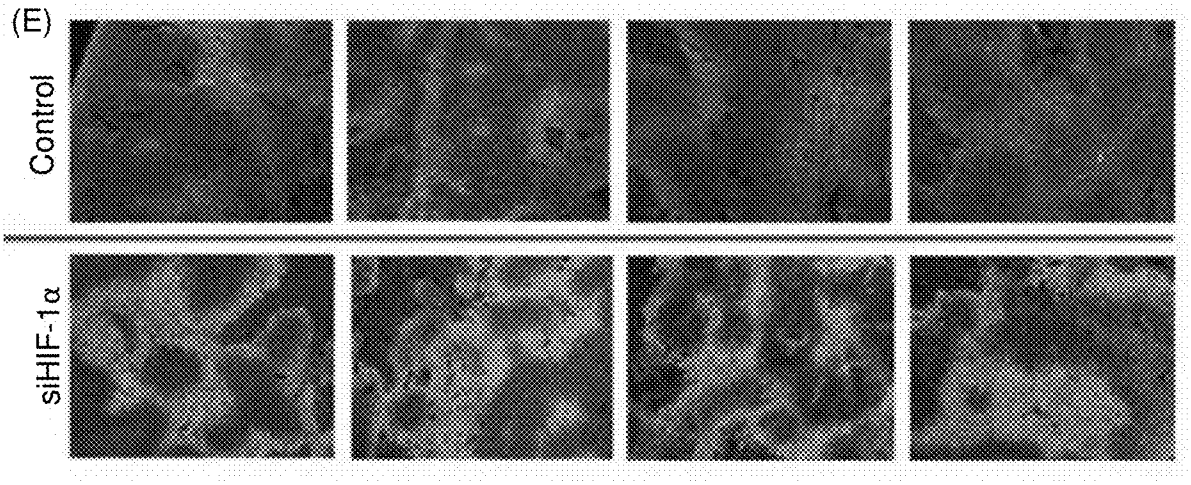
Figure 21D:
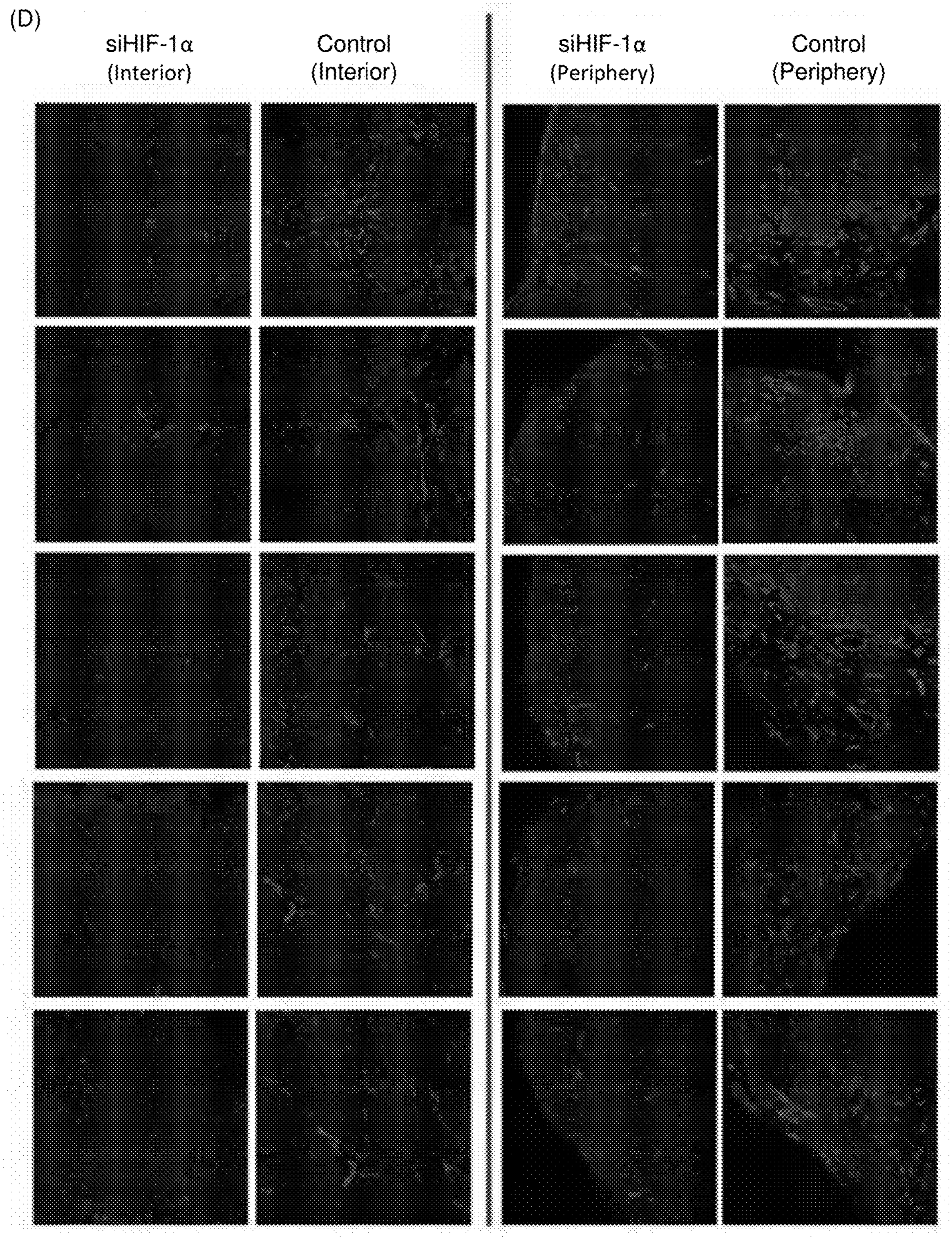

More specifically, the confocal images of CD31 expression in FIG. 21*d* show that the ECO/siHIF-1α therapy greatly reduces the vascular network in both the peripheral and core regions of the tumor lesion. In both groups, the degree of vascular coverage was much lower in the tumor core as opposed to the periphery. Although the control and siHIF-1α tumors each contained areas of interior necrosis, only the viable core tissue was imaged for CD31 expression. The figures obtained from such analysis revealed that the vascular network actually appeared to be largely absent from the cores of siHIF-1α treated tumors. Since a decrease in vessel density usually impairs sufficient tissue oxygenation, it was not surprising to see from the pimonidazole staining in FIG. 21*e* that the lower levels of CD31 expression in siHIF-1α tumors corresponded to greater levels of tumor hypoxia in the non-necrotic parts of the lesion.

Figure 22A:
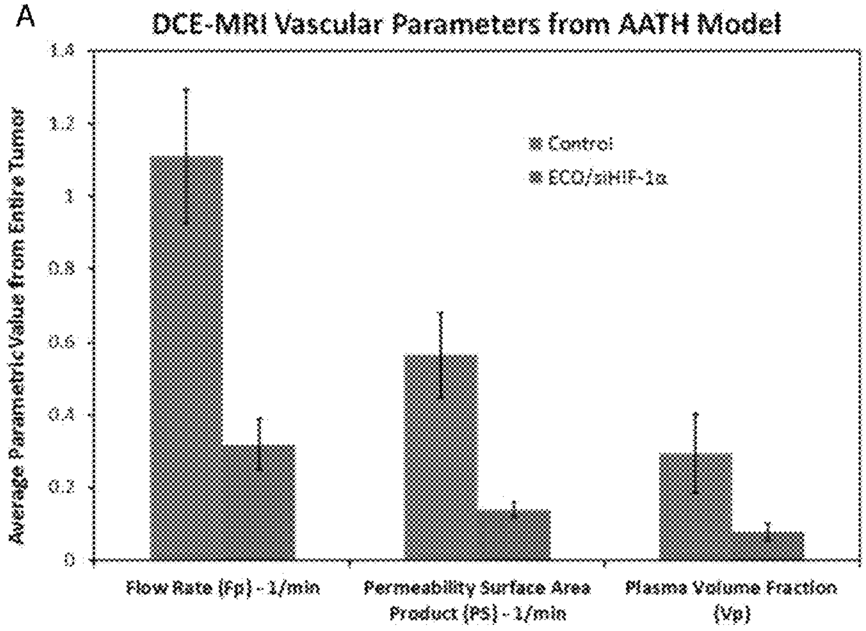
FIGS. 22(A-C) illustrate graphs showing DCE-MRI analysis using the AATH tracer kinetic model revealed significant decreases in average tumor blood flow (71.2%), permeability-surface area product (75.3%), and plasma volume fraction (73.2%) after the ECO/siHIF-1α therapy. The apparent regression in tumor vasculature was corroborated by significant decreases in average AUC (70.1%) and iAUC (66.9%) calculations.
Figure 22B:
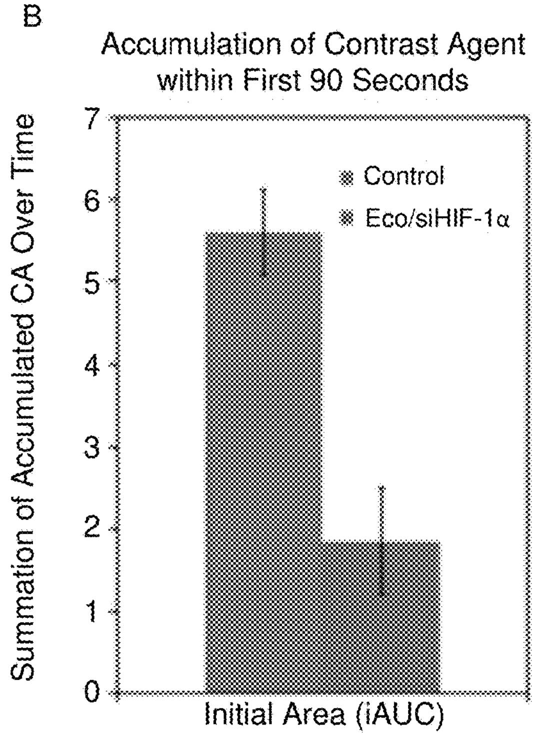
Figure 22C:
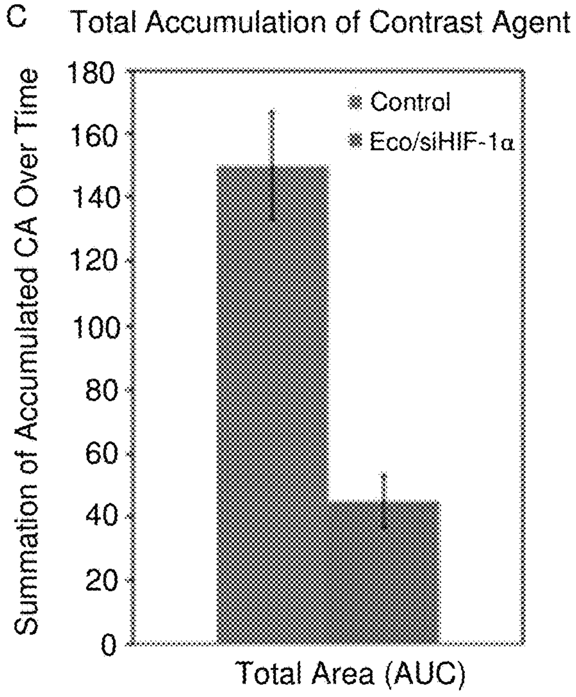

Dynamic Contrast Enhanced-MRI Verifies Anti-Angiogenic Effects of siHIF-1α Therapy We were interested in exploring the use of dynamic-contrast enhanced MRI (DCE-MRI) to aid in the non-invasive evaluation of the potential anti-angiogenic effects of the ECO/siHIF-1α therapy prior to tumor resection. DCE-MRI employs rapid imaging acquisition techniques to analyze the uptake of intravenously administered contrast agents into a tissue of interest over time. Once an uptake curve is generated, pharmacokinetic (PK) tracer kinetic modeling approaches can be utilized to calculate parametric values that characterize the pathophysiology of the vascular network and serve as relevant biomarkers. Here, we utilized the adiabatic approximation to the tissue homogeneity model to obtain information pertaining to blood flow (Fp), permeability (PS), and fractional blood volume (Vp). Following completion of the ECO/siHIF-1α treatment regimen, DCE-MRI analysis on 4 subjects from each group revealed that the siHIF-1α tumors possessed significantly lower Fp, PS, and Vp parametric values when MRI signal intensities were averaged over the entire tumor. These three parameters were 71.2%, 75.3%, and 73.2% lower, respectively, in the siHIF-1α treated tumors than their saline control counterparts (FIG. 22*a*), implicating the suppression angiogenic activity in response to the RNAi therapy. In concert with these changes, area-under-the-curve calculations over the entire imaging sequence (AUC) or just within the first 90 seconds (iAUC) also significantly decreased by 70.1% and 66.9%, respectively (FIG. 22B-C).

Figure 23A:
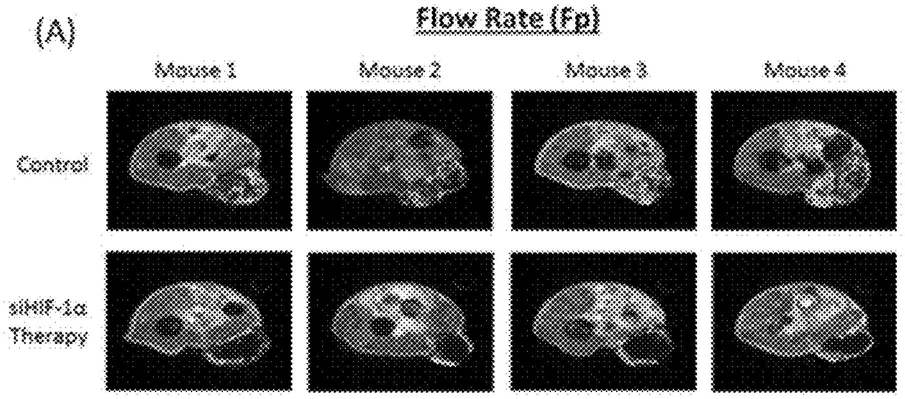
FIGS. 23(A-D) illustrate images showing significant reductions in the Fp (A), PS (B), Vp (C), and AUC (D) parameters throughout the siHIF-1α treated tumors. The spatial distribution also changes compared to the control saline therapy, whereby most of the vasculatures appear to be confine to the tumor periphery and not throughout the lesions.
Figure 23B:
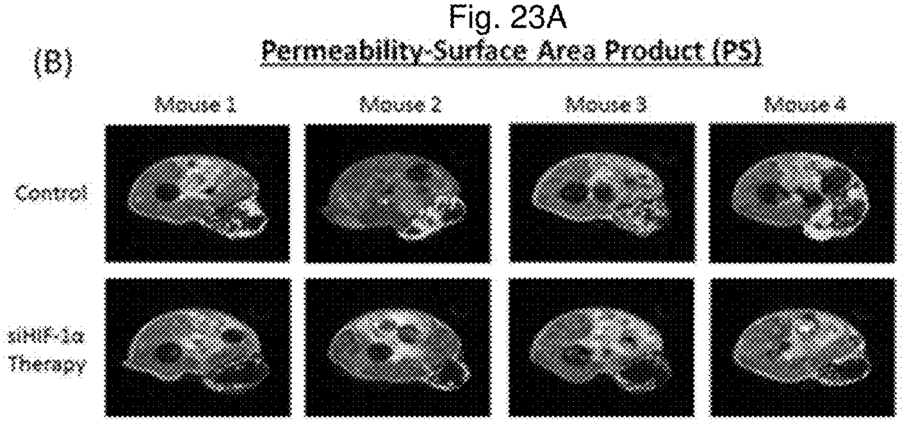
Figure 23C:
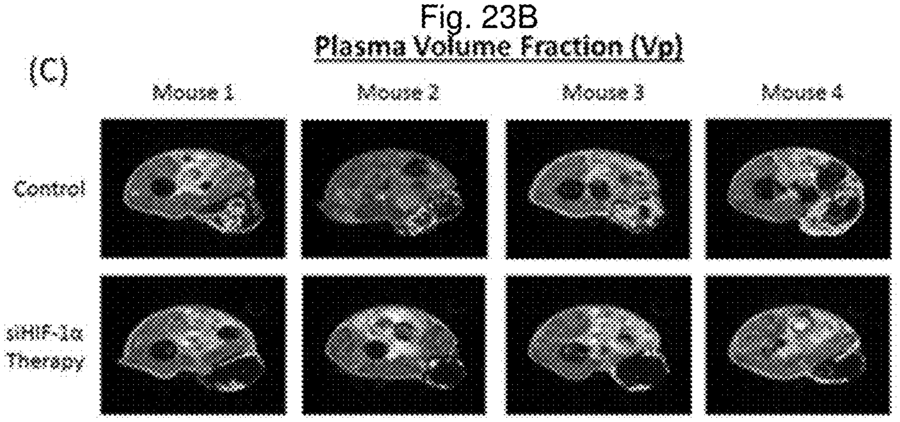
Figure 23D:
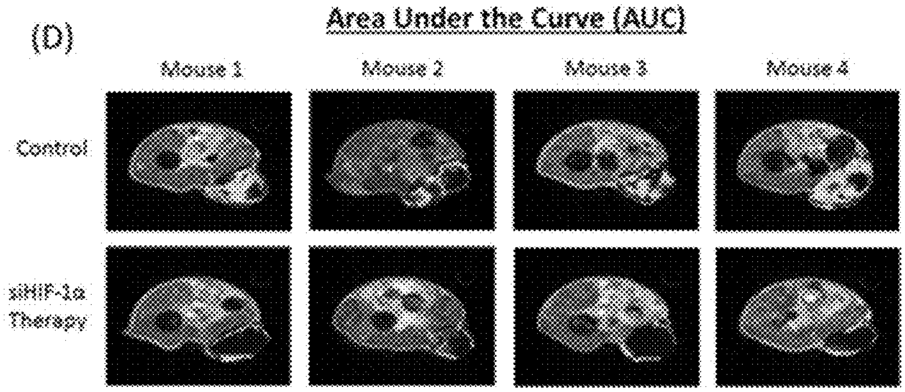

These results were verified when PK parameter estimation was performed on a pixel-by-pixel basis. The parametric Vp map shown in FIG. 8*a* reveals that the vasculature is confined to the periphery of the primary lesion in each of the siHIF-1α tumors we analyzed. However, control tumors were shown to have a substantial vascular network throughout the tissue, and not just in the outer regions. Similar spatial distributions were observed in the Fp, PS, and area-under-the-curve mappings due to the high degree of vascular collapse in the tumor core following siHIF-1α therapy (FIG. 23B-D). H&E stains of the control and siHIF-1α tumors correlated with the spatial distribution patterns observed in the parameter mapping to verify this observation. In FIG. 23E, we can see that there is much more necrotic tissue in the center of the siHIF-1α tumors than in the control group, and the presence of this necrotic tissue appears to coincide with areas low, or even non-existent, vascular activity in the DCE-MRI parametric maps. This suggests that the anti-angiogenic behavior of the ECO/siHIF-1α therapy can result in severe vascular regression, and that the prolonged, chronic lack of blood vessels can induce prolific cell death throughout the lesion. Overall, the siHIF-1α therapy possesses anti-angiogenic capabilities that may ultimately contribute to the decline of tumor progression in HT29 colon cancer xenografts.

Methods

Synthesis of Multifunctional Lipids

ECO

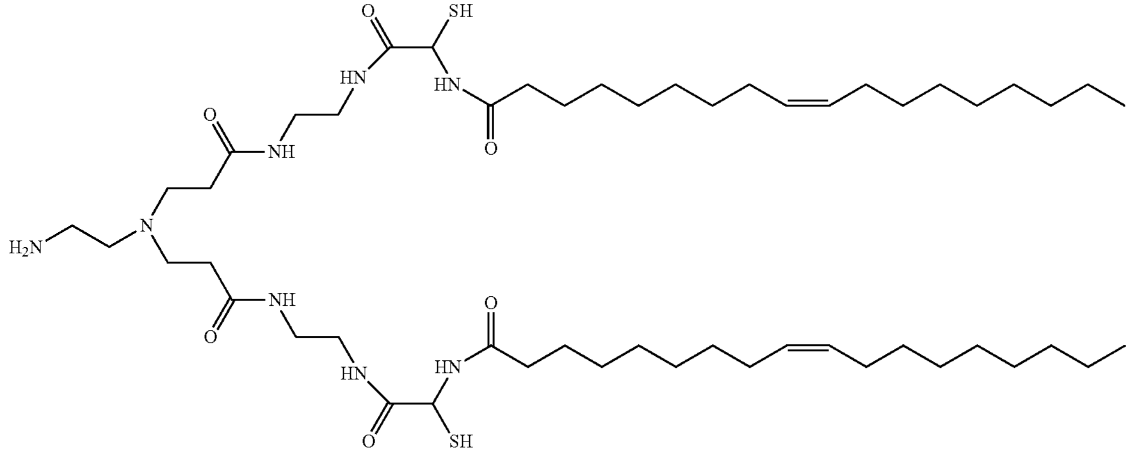

-continued

ECL

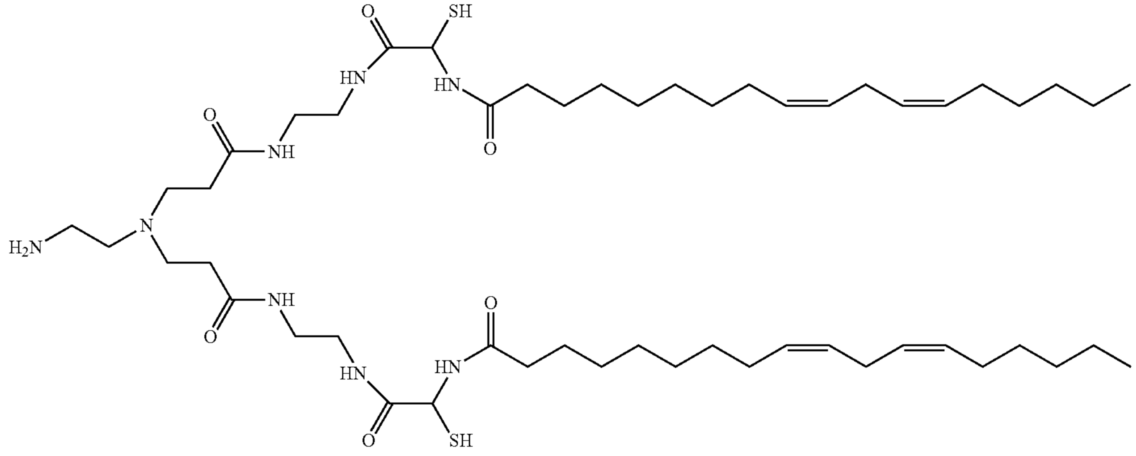

The chemical structures of ECO and ECL.

The synthesis of (1-aminoethyl)imino-bis[N-(oleicyl-cysteinyl-1-aminoethyl)propionamide] (ECO) was done by liquid-phase chemistry and is described below. The reaction scheme can be seen in FIG. 24. The ethylenediamine head group was synthesized first followed by the cysteine/oleic acid tail groups. Once these two groups were synthesized they were reacted together to arrive at the final ECO product. Each reaction intermediate was confirmed through $^1$H NMR.

SiRNA Nanoparticle Preparation and Characterization

Once each lipid carrier was purified and ready to be used for in-vitro testing, it was dissolved in ethanol at a 2.5 mM concentration. The lipid carriers were cationic in nature, and thus could form charge-based complexes with anionic siRNA, which was diluted to create a 0.25 mg/mL stock concentration. Particles were formed by first determining the quantity of siRNA required for each study, and then properly mixing volumes of both the lipid and siRNA stocks together according to pre-determined N/P ratios (N is the number of protonable amines on lipid carrier, P is the number of phosphates on siRNA). After mixing for 30 minutes, the particles were ready to be used for further biological and physiochemical evaluation.

Nanoparticle Characterization

Figure 25:
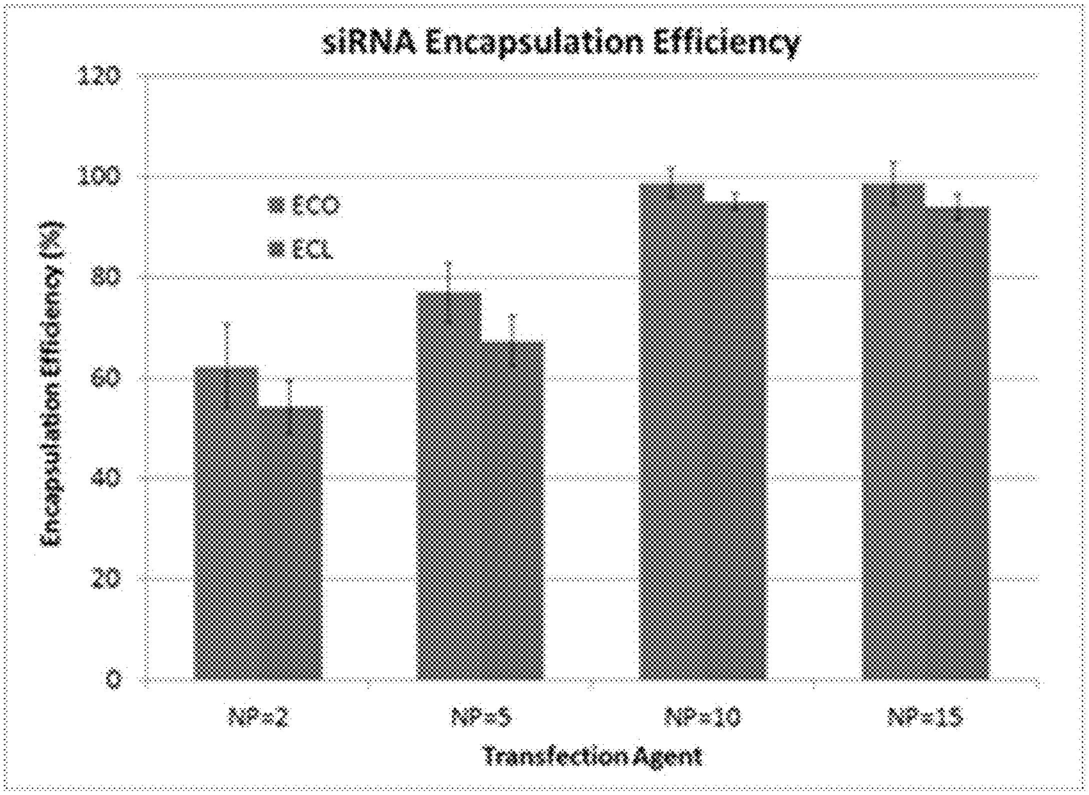
FIG. 25 illustrates a graph showing siRNA encapsulation efficiency of the ECO and ECL delivery systems. An Invitrogen RiboGreen assay was used to quantify free nucleic acid after particle formation.

FIG. 25 illustrates a graph showing siRNA encapsulation efficiency of the ECO and ECL delivery systems. An Invitrogen RiboGreen assay was used to quantify free nucleic acid after particle formation.

pH-Sensitive Membrane Disruption

Hemolytic activity of each carrier was measured in order to verify the pH-sensitive membrane disruption capabilities of our proposed delivery system. In particular this assay allowed us to determine if our nanoparticles disrupt membranes of the endosomal compartments (pH=5-6), without affecting the integrity of the outer cell membrane prior to endocytosis (pH=7.4).

Figure 26:
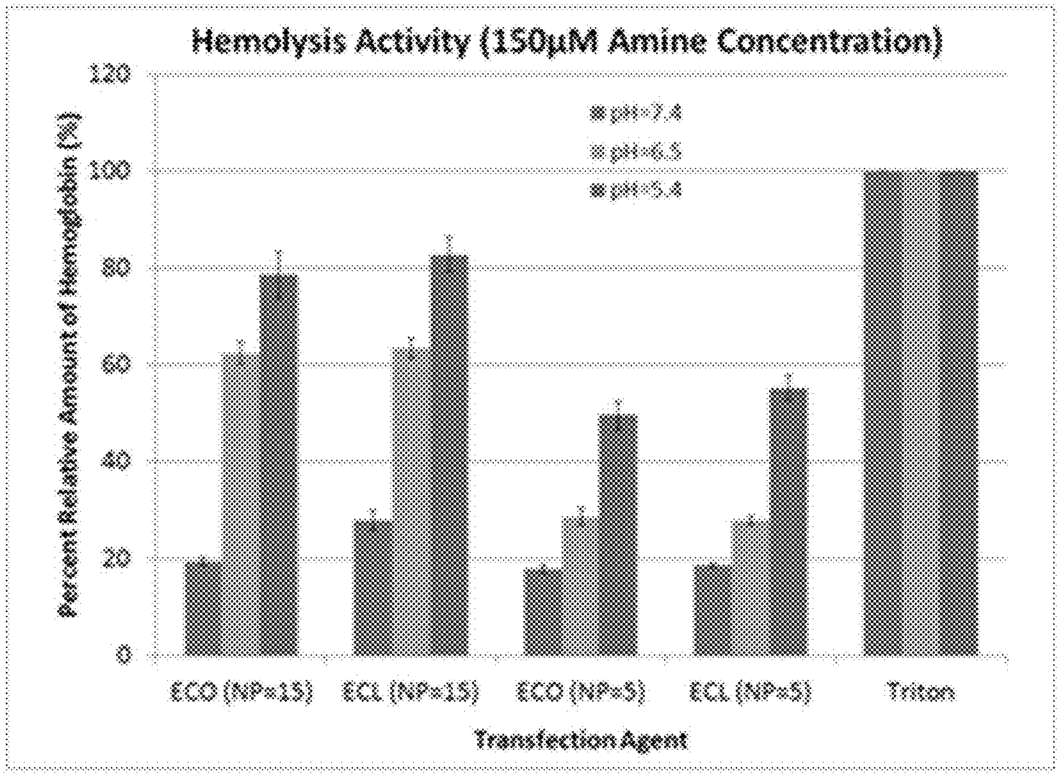
FIG. 26 illustrates a graph showing the relative amount of hemoglobin that was released from red blood cells during a 2 hour incubation period with the ECO and ECL nanoparticles. Both agents effectively displace significant membrane destabilizing capabilities following a pH drop, which typically occurs in endosomes.

To accomplish this, we created nanoparticles at different N/P ratios and incubated them with red blood cells extracted from rats at a 100× dilution. All samples were incubated at 37° C. for 2 hours in PBS buffer at pH=5.4, 6.5, or 7.4. The concentration of amines was 150 μM for each sample we tested. Theoretically, membrane destabilization causes red blood cells to release their hemoglobin, causing a significant increase in the absorbance of the sample at 540 nm following the incubation period. The surfactant triton X-100 was also added to red blood cells to serve as a positive to allow us to calculate the degree of hemolytic activity both delivery systems exhibit. The data presented in FIG. 26 shows a selective increase in the membrane destabilization capabilities of the ECO and ECL delivery systems as the pH of their surrounding medium is decreased, thus implicating their potential endosomolytic activity upon cellular uptake.

Evaluation of Intracellular siRNA Dispersion via Confocal Microscopy

Figure 27:
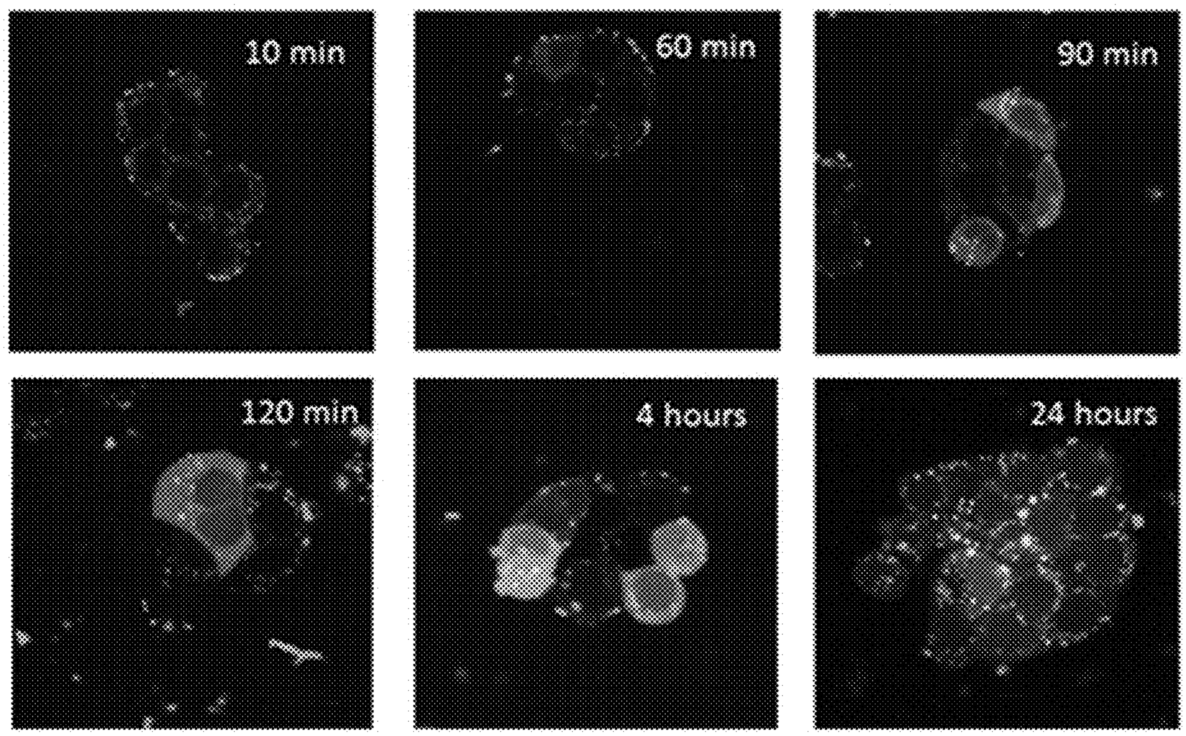
FIG. 27 illustrates a confocal image showing that the ECO delivery system is able promote intracellular dispersion of siRNA (labeled green with Alexafluor-488) within the cytosol, preventing degradation within lysosomes (labeled red with Lysotracker Red-DND99). This is evident by the minimal co-localization seen at the later time points.

Confocal microscopy was utilized to perform a time course study that analyzed the uptake and intracellular release kinetics of siRNA using the ECO delivery platform. Intracellular release and dispersion of siRNA is essential in RNA interference since the RNAi machinery is found in the cytosol. The images in FIG. 27 reveal that upon cellular uptake, the ECO nanoparticles are able to facilitate the escape of its siRNA payload from the endocytic pathway within the first 2 hours after transfection, avoiding lysosomal degradation. Such results are in congruence with the hemolytic activity data showing the membrane disruptive properties of the delivery system in pH environments characteristic of both endosomes and lysosomes.

In Vitro Gene Silencing Efficiency and Cytotoxicity

Figure 28:
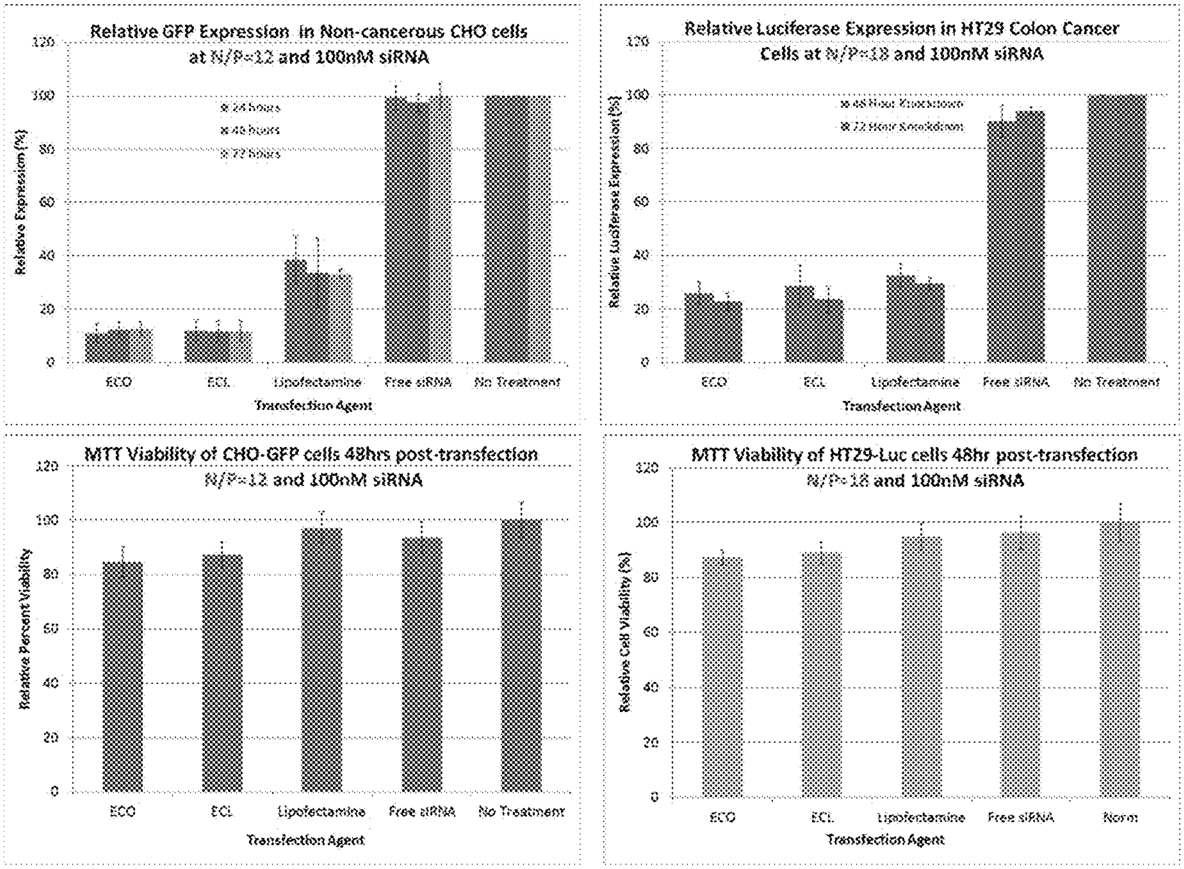
FIG. 28 illustrates graphs showing siRNA silencing efficiency and MTT viability in a cancerous (HT29) and noncancerous (CHO) cell line post-transfection. The data presented here are the results obtained at the optimal N/P ratios.
Figure 29:
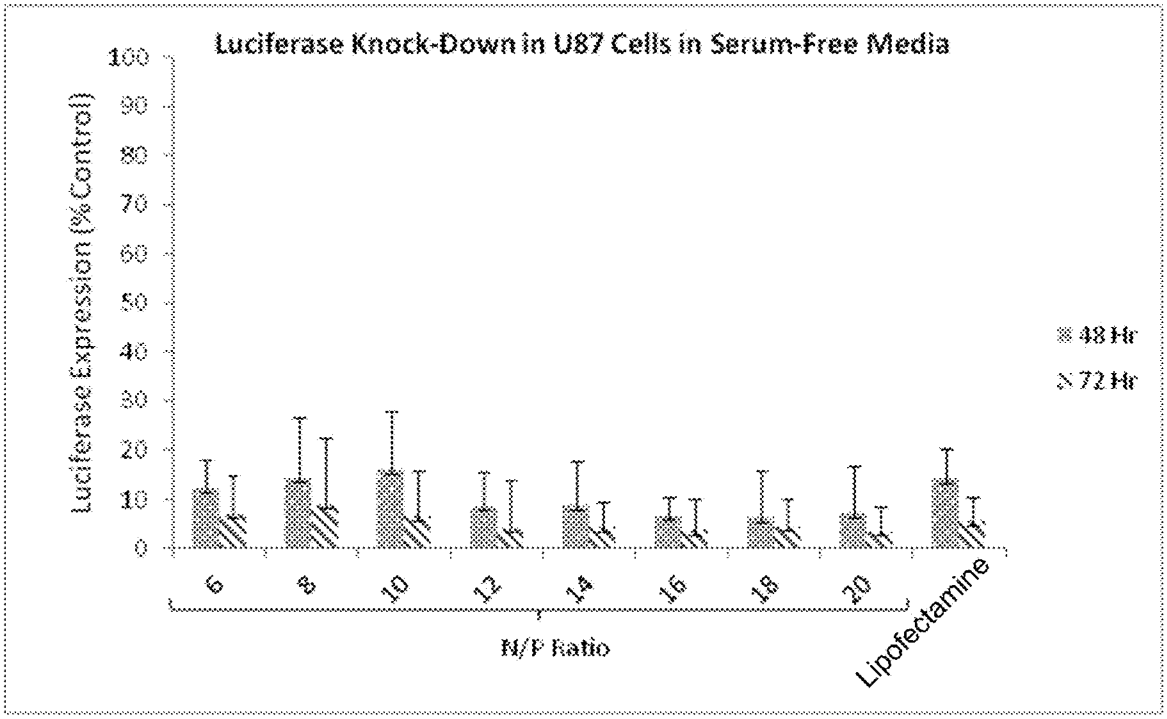
FIG. 29 illustrates a graph showing luciferase knockdown of U87-Luc cells with ECO at varying N/P ratios in serum-free media.
Figure 30:
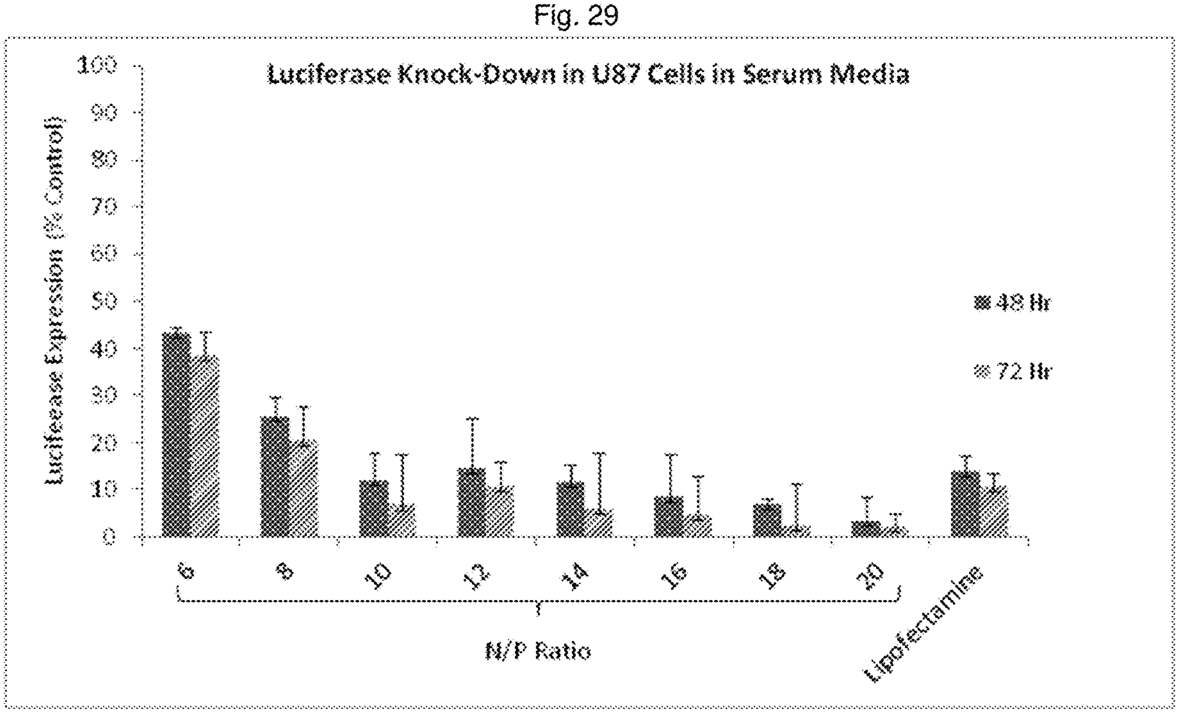
FIG. 30 illustrates a graph showing luciferase knockdown of U87-Luc cells with ECO at varying N/P ratios in serum-containing media.

The RNAi capabilities of each carrier were investigated by analyzing the silencing of a luciferase (Luc) reporter in HT29 cancer cells after anti-Luc siRNA therapy. To perform this study, we seeded HT29-Luc cells in 12 well plates at a density of 20,000 cells per well. When 25% confluency, the cells were incubated with fresh serum-free transfection media containing nanoparticles at a dose of 100 nM siRNA. After 4 hours, the media was replaced with fresh complete growth media, so that the cells could continue to grow for an additional 48-72 hours, at which point they were lysed for protein collection. The lysis buffer was compatible with the BCA protein assay so that we could normalize luciferase expression in our samples. Negative controls included cells that were treated with 1) particles encapsulating non-specific siRNA, 2) naked anti-Luc siRNA, or 3) plain serum-free media. Luciferase expression was determined using a Spectra Max luminometer upon the addition of a light-inducing substrate to the collected protein. A similar knockdown experiment was also conducted in non-cancerous CHO cells expressing a GFP reporter. Flow cytometry was utilized to assess the silencing efficiency of the ECO and ECL delivery systems in this cell line. Cytotoxicity of the carriers 48 hours post-transfection was also investigated in both cell lines using an MTT colorimetric assay. FIG. 28 shows that 80% and 75% silencing efficiency was achieved for the ECO and ECL delivery systems respectively in the HT29-Luc cells at an N/P ratio of 18, while 85-90% knockdown was achieved in the CHO-GFP cell line at an N/P ratio of 12, over the course of 72 hours. These RNAi silencing levels surpassed those obtained with a Lipofectamine RNAiMax commercial transfection agent. FIG. 28 also reveals that both delivery systems possess minimal cytoxicity, as seen by cell viability level greater than 85%.

U87-Luciferase cells were seeded on 24-well plates at a density of 20,000 cells/well and grown for 48 hours. ECO was added to RNase-free water at varying concentrations depending on N/P ratio. Anti-luciferase siRNA was diluted in RNase-free water to give a total transfection concentration of 40 nM. Equal volumes of ECO and siRNA were mixed together, mixed gently with pipette and incubated for 30 minutes. The particles were added to either serum-free or serum-containing media to give a total transfection volume of 400 μL and the cells were incubated for 4 h in cell culture conditions. After 4 h, the media was removed and replaced with 400 μL serum-containing media. After 48 h and 72 h, the cells were lysed and a luciferase assay was conducted to quantify the expression of luciferase and a BCA assay was conducted to quantify protein content in each well. Lipofectamine RNAiMAX was used to compare the efficacy of ECO to a commercially available carrier and all data was normalized to a control group that received no treatment.

Example 4

Figure 31A:
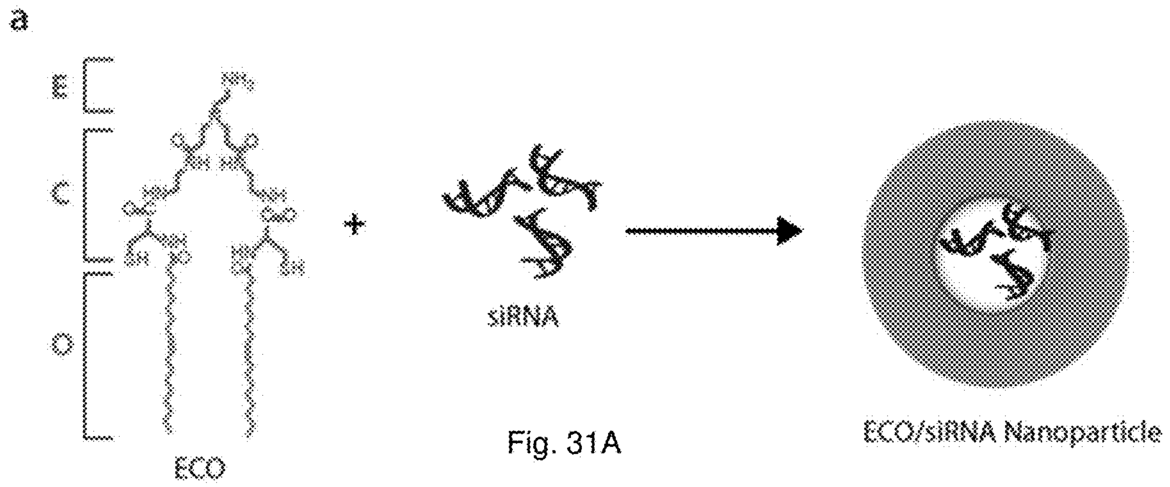
FIGS. 31(A-D) illustrate a schematic, plots, and immunoblots showing ECO/siβ3 nanoparticles induced sustained gene silencing of β3 integrin. A) ECO forms nanoparticles with siRNA through electrostatic interactions, disulfide cross-linking and hydrophobic interactions. B) integrin mRNA expression in quiescent or TGF-β stimulated (5 ng/mL, 72 hours) NME and MDA-MB-231 cells with the indicated treatment groups at 100 nM siRNA by semi-quantitative real-time PCR (n=3, mean±SE, p≤0.01 for all time points beyond 8 hours). Western blot analysis of β3 integrin expression in quiescent or TGF-β stimulated (5 ng/mL, 72 hours) NME c) and MDA-MB-231 d) cells at the indicated time points post-nanoparticle treatment with the indicated treatment groups.

RNAi-based therapeutic regimens hold tremendous potential for downregulating oncogene expression. However, clinical applications of RNAi have been limited by challenges associated with delivering siRNA, including potential immunogenicity, poor cellular uptake of unmodified siRNA, and degradation by serum nucleases. Nanoparticle-mediated delivery of siRNA is desirable due to its ability to protect siRNAs and facilitate their uptake into target cells. Although various delivery systems are reported to exhibit efficient transfection, concerns regarding their clinical safety and efficacy continue to prevent the advancement of RNAi-based therapeutics. Cationic lipid-based carriers have demonstrated remarkable delivery potential due to their ability to readily form complexes with negatively charged siRNAs, and to efficiently promote cellular uptake of the siRNA cargo. We developed a multifunctional cationic lipid-based carrier, (1-aminoethyl)iminobis[N-oleicylsteinyl-1-aminoethyl)propionamide](ECO), which facilitates effective siRNA-mediated RNAi in various cancer cell lines. ECO ionically complexes with siRNA and forms stable nanoparticles to protect the siRNA cargo from degradation (FIG. 31A). Once internalized and trafficked to the late endosomes, the pH-sensitive amphiphilicity of ECO promotes endo-lysosomal escape of the nanoparticles, and reduction of the disulfide linkages created during nanoparticle formation by cytosolic glutathione releases the siRNA to achieve potent gene silencing. ECO is also designed to facilitate facile and versatile functionalization of the surface of these nanoparticles with targeting moieties.

Considering the critical roles of β3 integrin in tumor progression and the urgent need for targeted therapies tailored specifically to TNBC, we sought to alleviate TNBC metastasis by silencing β3 integrin using ECO/siRNA nanoparticles. The present study demonstrates the efficacy of ECO/siβ3 nanoparticles in silencing β3 integrin expression and the consequent inhibition of TGF-β-mediated EMT and invasion of breast cancer cells in vitro. The nanoparticles were modified with RGD peptides via PEG spacers to improve biocompatibility and systemic target-specific delivery of the therapeutic siβ3 in vivo. The efficacy of the RGD-targeted ECO/siβ3 nanoparticles in alleviating primary and metastatic tumor burden was determined in tumor-bearing mice following multiple intravenous injections.

Preparation of ECO/siRNA Nanoparticles

ECO/siRNA nanoparticles were prepared at an N/P ratio of 8. ECO and siRNA were diluted in equal volumes in nuclease-free water from stock solutions of 2.5 mM in ethanol and 18.8 μM in nuclease-free water, respectively. The equal volumes of ECO and siRNA were mixed followed by a 30-mM incubation period at room temperature under gentle agitation. For RGD- and RAD-modified ECO/siRNA nanoparticles, RGD-PEG-Mal or RAD-PEG-Mal (MW=3,400 Da; NANOCS, New York, NY) was added into an ECO solution at 2.5 mol % for 30 mM under gentle agitation and subsequently mixed with an equal volume of siRNA in RNase-free water for an additional 30 mM. After the incubation, free peptide derivative was removed from RGD- and RAD-modified ECO/siRNA nanoparticles by ultrafiltration (Nanosep, MWCO=100 K, 5000×g, 5 min; Sigma Aldrich, St. Louis, MO). The following siRNAs were purchased from Integrated DNA Technologies (Coralville, IA): Mouse integrin β3 sense: [GCUCAUCUGGAAGCUACUCAUCACT], Mouse integrin β3 antisense: [AGUGAUGAGUAGCUUCCAGAUGAGCUC], Human integrin β3 sense: [GCUCAUCUGGAAACUCCUCAUCACC], and Human integrin β3 antisense:

[GGUGAUGAGGAGUUUCCAGAUGAGCUC].

Cell Lines and Reagents

MDA-MB-231 cells were obtained from ATCC (Manassas, VA) and cultured in Dulbecco's Modified Eagle Medium (DMEM; Gibco, Grand Island, NY) supplemented with 10% fetal bovine serum (FBS; Gibco, Grand Island, NY). NME were engineered as previously described[37] and cultured in DMEM supplemented with 10% FBS and 10 μg/mL of insulin. Both cell lines were engineered to stably express firefly luciferase by transfection with pNifty-CMV-luciferase and selection with Zeocin (500 μg/ml; Invitrogen, Carlsbad, CA).

Western Blot Analyses

Immunoblotting analyses were performed as previously described. Briefly, NME and MDA-MB-231 cells were seeded into 6-well plates ($1.5\times10^5$ cells/well) and allowed to adhere overnight. The cells were then incubated in the absence or presence of TGF-β1 (5 ng/mL) for 3 d and then treated with ECO/siRNA complexes for 4 h in complete growth medium. At each indicated time point, detergent-solubilized whole cell extracts (WCE) were prepared by lysing the cells in Buffer H (50 mM β-glycerophosphate, 1.5 mM EGTA, 1 mM DTT, 0.2 mM sodium orthovanadate, 1 mM benzamidine, 10 mg/mL leupeptin, and 10 mg/mL aprotinin, pH 7.3). The clarified WCE (20 mg/lane) were separated through 10% SDS-PAGE, transferred electrophoretically to nitrocellulose membranes, and immunoblotted with the primary antibodies, anti-β3 integrin (1:1000; Cell Signaling) and anti-β-actin (1:1000; Santa Cruz Biotechnology).

Flow Cytometry for Nanoparticle Cellular Uptake

Cellular uptake and intracellular delivery of ECO/siRNA and RGD-ECO/siRNA nanoparticles was evaluated quantitatively using flow cytometry. ECO/siRNA and RGD-ECO/siRNA nanoparticles were prepared with 40 nM Alexa Fluor 488-labeled siRNA (Qiagen; Valencia, CA). Approximately $2.5 \times 10^4$ U87 cells were seeded onto 12-well plates and grown for an additional 24 h. The cells were transfected with ECO/siRNA nanoparticles in 10% serum media. After 4 h, the transfection media was removed and each well was washed twice with PBS. The cells were harvested by treatment with 0.25% trypsin containing 0.26 mM EDTA (Invitrogen; Carlsbad, CA), collected by centrifugation at 1,000 rpm for 5 min, resuspended in 500 μL of PBS containing 5% paraformaldehyde, and finally passed through a 35 μm cell strainer (BD Biosciences; San Jose, CA). Cellular internalization of the nanoparticles was quantified by the fluorescence intensity measurement of Alexa Fluor 488 for a total of $1 \times 10^4$ cells per sample using a BD FACSCalibur flow cytometer. All the experiments were performed in triplicate and the data represent mean fluorescence intensity and standard deviation.

Semi-Quantitative Real-Time PCR Analyses

Real-time PCR studies were performed as described previously. Briefly, NME or MDA-MB-231 cells (100,000 cells/well) were seeded overnight onto 6-well plates and treated with TGF-β (5 ng/mL) for 3 days upon delivery of ECO nanoparticles with a non-specific siRNA or β3 integrin-specific siRNA. At each indicated timepoint, total RNA was isolated using the RNeasy Plus Kit (Qiagen, Valencia, CA) and reverse transcribed using the iScript cDNA Synthesis System (Bio-Rad, Hercules, CA). Semi-quantitative real-time PCR was conducted using iQ-SYBR Green (Bio-Rad) according to manufacturer's recommendations. In all cases, differences in RNA expression for each individual gene were normalized to their corresponding GAPDH RNA signals.

Invasion and Proliferation Assays

Invasion assays were conducted as described previously. Briefly, NME cells, unstimulated (Pre-) or stimulated with TGF-β for 3 d (Post-EMT), were treated with the ECO/siRNA complexes for an additional 2 d. The cells were then trypsinized and their ability to invade reconstituted basement membranes ($5 \times 10^4$ cells/well) was measured utilizing modified Boyden chambers, as previously described. For the proliferation assay, the NME cells were cultured ($1 \times 10^4$ cells/well) in the presence (post-EMT) or absence (pre-EMT) of TGF-β (5 ng/mL) for 3 d and then treated with ECO/siRNA. Cell proliferation was determined by $^3$H-thymidine incorporation as previously described.

3-Dimensional (3D)-Organotypic Cultures 3D-organotypic cultures utilizing the "on-top" method were performed as described previously. NME or MDA-MB-231 cells, which were unstimulated (Pre-EMT) or stimulated with TGF-β (5 ng/mL) for 3 d (Post-EMT), were cultured in 96-well, white-walled, clear bottom tissue culture plates (2,000 cells/well) with 50 μL of Cultrex cushions (Trevigen, Gaithersburg, MD) in media supplemented with 5% Cultrex. The cells were maintained in culture for 4 d with continuous ECO/siRNA treatment every 2 d. Growth was monitored by bright-field microscopy or bioluminescent growth assays (where indicated) using luciferin substrate.

Tumor Growth and Bioluminescent Imaging (BLI)

All the animal studies were performed in accordance with the Institutional Animal Care and Use Committee for Case Western Reserve University. NME cells were engineered to stably express firefly luciferase, and were subsequently injected into the lateral tail vein of female nude mice ($1 \times 10^6$ cells/mouse) after TGF-β stimulation (5 ng/mL) for 7 days. The pulmonary outgrowth was monitored and determined as described previously. MDA-MB-231 cells, also engineered to express firefly luciferase and stimulated with TGF-β for 7 days, were engrafted into the mammary fat pad of female nude mice.

Immunofluorescence and Immunohistochemical Staining

For visualization of the actin cytoskeleton, immunofluorescent analysis was performed as previously described. NME cells ($5 \times 10^4$ cells/well) were plated onto glass-bottom confocal dishes and allowed to adhere overnight, after which they were simultaneously stimulated with TGF-β (5 ng/mL) and treated with ECO/siRNA nanoparticles, either siβ3 or siNS at 100 nM siRNA concentration. After 48 and 72 h of simultaneous TGF-β stimulation and nanoparticle treatment, the cells were washed with PBS, fixed with 4% paraformaldehyde, permeabilized in 0.1% Triton-X 100, stained with Alexa Flour 488 phalloidin (25 μM; Invitrogen; Carlsbad, CA), and visualized under a fluorescent confocal microscope.

For immunohistochemistry, primary tumor samples were frozen in OCT, sectioned, fixed in paraffin, and maintained at −80° C. The samples were stained with H&E to evaluate the presence of tumor tissue. For immunofluorescence detection of fibronectin, the paraffin-embedded slides were first deparaffinized using a series of washes in xylene and decreasing concentrations of ethanol. Following heat-induced antigen retrieval, the samples were blocked in TBST solution containing donkey serum and washed three times with TBST. The primary antibody (Abcam; Cambridge, MA) was applied for 1 h followed by three rinses with TBST. The Alexa Fluor 488 secondary antibody (Jackson; West Grove, PA) was applied for 1 h followed by three washes with TBST and counterstained with DAPI. After washing with TBST and mounting in an anti-fade mounting solution (Molecular Probes), the samples were imaged using a confocal microscope.

Results

ECO/Siβ3 Nanoparticles Induce Sustained Silencing of β3 Integrin

Figure 31B:
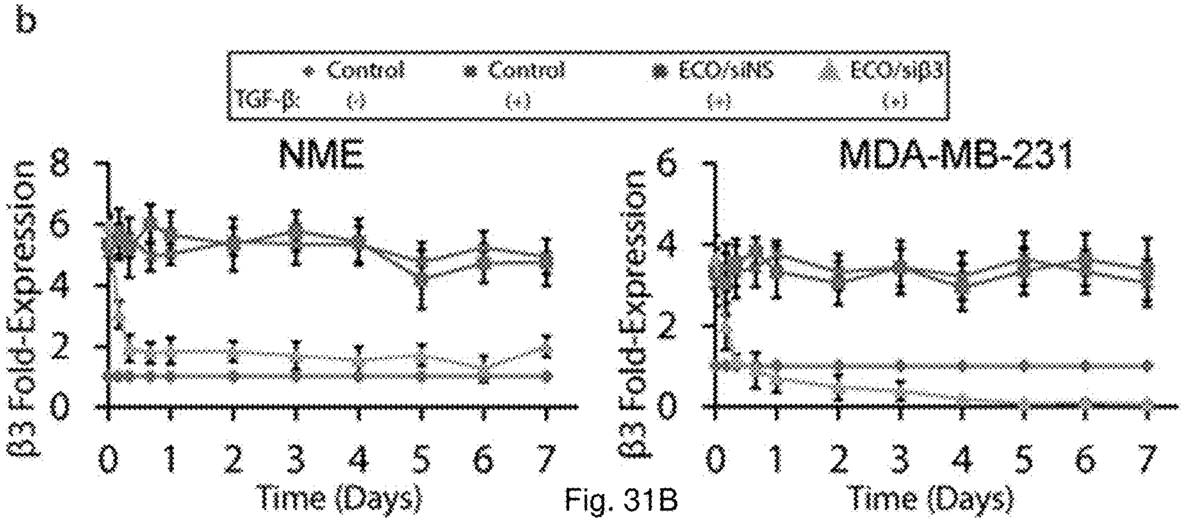
Figure 31C:
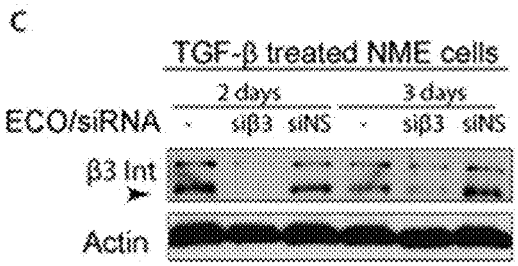
Figure 31D:
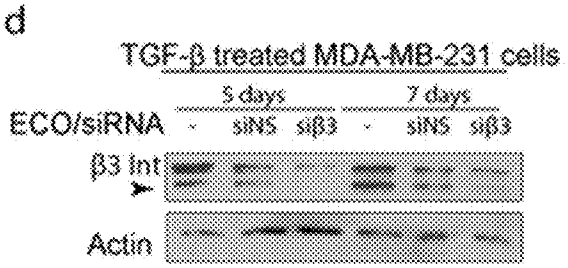

We examined the ability of ECO/β3 integrin-specific siRNA nanoparticles (ECO/siβ3) to silence β3 integrin expression in mouse NMuMG-EGFR (NME) breast cancer cells, reminiscent of a basal-like breast cancer cell line, and human MDA-MB-231 breast cancer cells, a mesenchymal-like TNBC cell line. The expression of β3 integrin was elevated in both cell lines after stimulation with TGF-β for 72 h. Subsequent treatment of the stimulated cells with ECO/siβ3 nanoparticles resulted in the rapid loss of β3 integrin mRNA within the first 16 h following treatment (FIG. 31B). β3 integrin expression was reduced by ~75% and this downregulation was sustained for up to 7 d in NME cells treated with TGF-β (FIGS. 31B and C). ECO/siβ3 treatment of MDA-MB-231 cells reduced β3 integrin expression level to that of the unstimulated cells (FIGS. 31B and D). Importantly, treatment with ECO/nonspecific siRNA nanoparticles (ECO/siNS) failed to alter β3 integrin expression in both cell lines (FIGS. 31B, C, and D). Collectively, these results demonstrate the ability of ECO/siβ3 nanoparticles to induce efficient and prolonged silencing of β3 integrin expression in breast cancer cells.

Figure 32A:
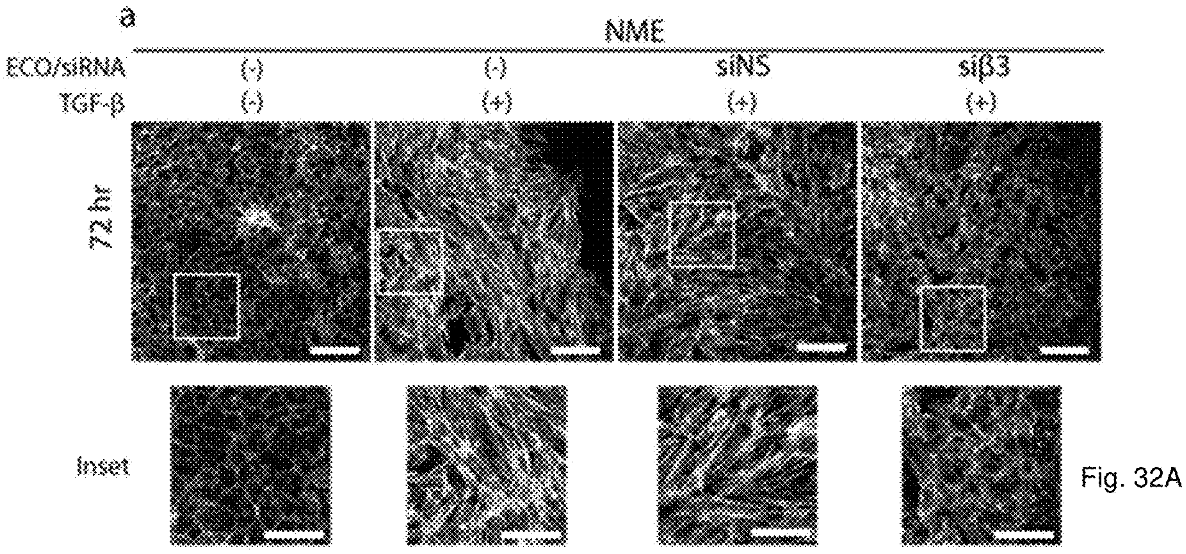
FIG. 32(A-E) illustrate images, graphs, and an immunoblot showing ECO/siβ3 nanoparticles attenuated TGF-β-mediated EMT, invasion and proliferation. A) Immunofluorescent images of actin cytoskeleton visualized with rhodamine-conjugated phalloidin in mouse NME cells with different treatments (scale bar, 100 μm; inset scale bar, 50 μm). B) Semi-quantitative real-time PCR analysis (n=3) of EMT markers in NME cells (**p≤0.01). C) Western blot analysis of E-cadherin and N-cadherin in NME cells. D) Invasion assay of quiescent or TGF-β stimulated NME cells (n=3, *p≤0.05, **p≤0.01). E) Proliferation as measured by [$^3$H]thymidine incorporation of either quiescent or TGF-β stimulated NME cells (n=3, *p≤0.05, **p≤0.01). For all experimental groups, NME cells were pre-treated with TGF-β (5 ng/mL; 72 hours) followed by ECO/siRNA nanoparticle treatment using 100 nM siRNA. For panels b-e, data represent mean±SE. Results for panels c-e are representative of three independent experiments.
Figure 32B:
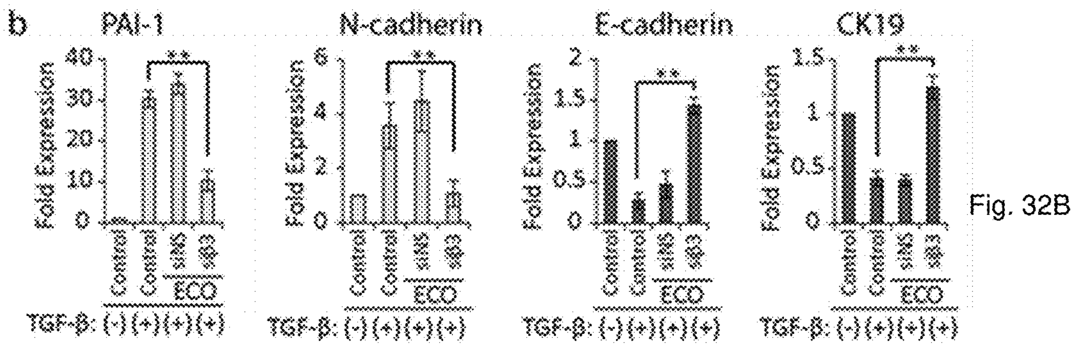
Figure 32C:
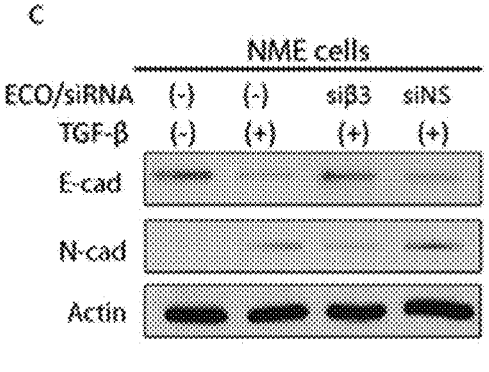

ECO/Siβ3 Nanoparticles Attenuate TGF-β-Mediated EMT, Invasion, and Proliferation Next, we investigated the effects of ECO/siβ3 nanoparticles on EMT, invasion, and proliferation of breast cancer cells. Phalloidin staining of the actin cytoskeletal architecture revealed that quiescent NME cells displayed the epithelial hallmark of densely packed and well-organized cortical actin network, while those stimulated with TGF-β exhibited dissolved junctional complexes and acquired an elongated morphology consistent with stress fiber formation that are characteristic of mesenchymal cells (FIG. 32A). Treatment of NME cells with ECO/siβ3 nanoparticles at the time of TGF-β stimulation inhibited dissolution of the junctional complexes and stress fiber formation, while treatment with ECO/siNS nanoparticles failed to impact TGF-β-induced morphological changes (FIG. 32A). Moreover, the phenotypic changes in post-EMT cells were accompanied by alterations in the expression of EMT-related genes. Silencing of β3 integrin with ECO/siβ3 nanoparticles significantly reduced TGF-β-mediated upregulation of the mesenchymal markers, N-cad and PAI-1, and inhibited TGF-β-mediated downregulation of the epithelial markers, E-cad and CK-19 (FIGS. 32B and C). ECO/siNS nanoparticles did not alter the effect of TGF-β on the aforementioned EMT markers.

Figure 32D:
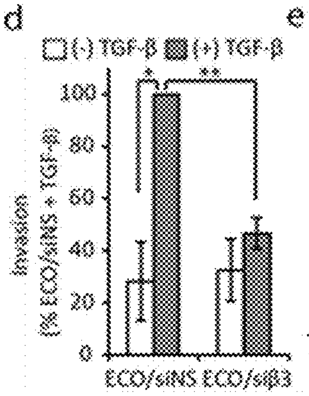
Figure 32E:
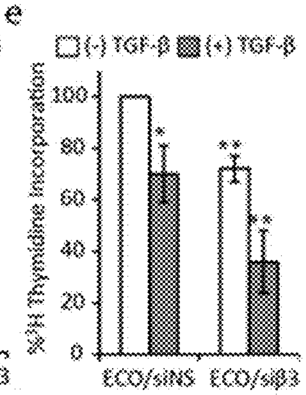

TGF-β-mediated EMT is also associated with increased invasiveness and cell cycle arrest. TGF-β-stimulated NME cells treated with ECO/siNS readily invaded reconstituted basement membrane, while ECO/siβ3 nanoparticles significantly inhibited invasion (FIG. 32D). Conversely, treatment of quiescent NME cells with ECO/siβ3 nanoparticles had no effect on basal invasiveness, an event that is uncoupled from β3 integrin expression. Previous studies demonstrate that parental NMuMG cells readily undergo proliferative arrest when stimulated with TGF-β[40]. We found that EGFR overexpression in the NME cells overrides these cytostatic effects of TGF-β (FIG. 33E), while treatment with ECO/siβ3 partially restores TGF-β-mediated cytostasis (FIG. 32E). Collectively, these findings indicate that ECO/siβ3 nanoparticle-mediated silencing of β3 integrin attenuates TGF-β-induced EMT and invasion, and partially restores TGF-β-mediated cytostasis.

Figure 33A:
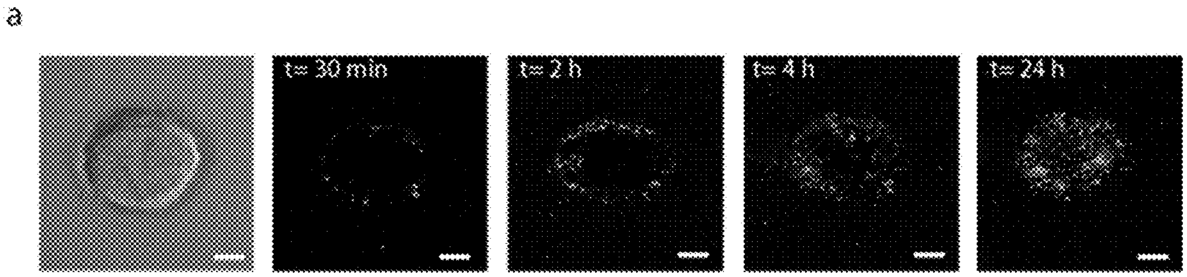
FIGS. 33(A-C) illustrate images and graphs showing ECO/siβ3 nanoparticles attenuated 3D organoid outgrowth. NME and MDA-MB-231 cells were grown in a compliant 3D-organotypic microenvironment and treated with ECO nanoparticles containing Alexa Fluor 488-labeled siRNA. Cellular uptake of ECO/siRNA nanoparticles monitored by fluorescence confocal microscopy (scale bar, 100 μm). A) Bright-field microscopic image of a single organoid and fluorescence confocal microscopic images of ECO/siRNA nanoparticle uptake in the organoid over the course of 24 hours. B) NME and c) MDA-MB-231 cells were grown in a compliant 3D-organotypic microenvironment for up to 10 days with or without prior TGF-β stimulation (5 ng/mL) for 72 h. On day 4, 6 and 8, cells were treated with ECO/siNS or ECO/siβ3 nanoparticles at 100 nM siRNA. Organoid growth at day 10 was monitored via longitudinal bioluminescence (n=4, *p≤0.05, **p≤0.01). For panels c-d, data represent mean±SE.
Figure 33B:
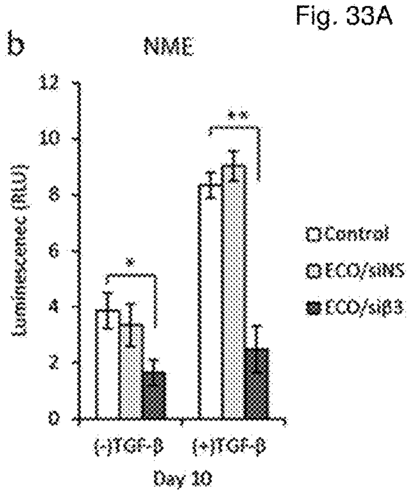
Figure 33C:
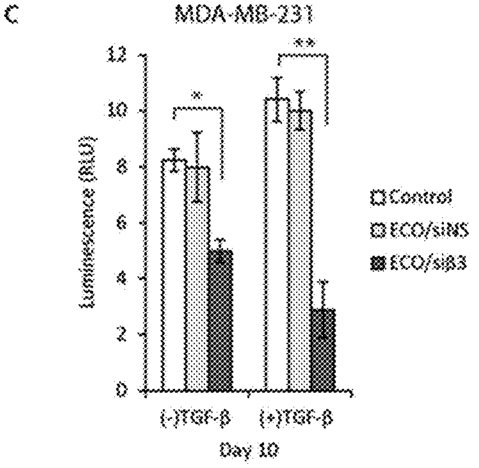
Figure 34A:
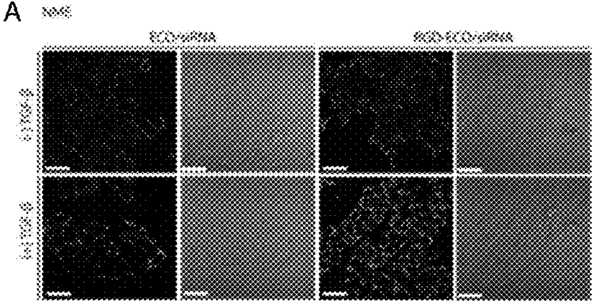
FIGS. 34(A-E) illustrate images and a graph showing RGD modification of ECO/siRNA nanoparticles enhances uptake in post-EMT breast cancer cells. A) confocal microscopy (scale bar, 50 μm) and B) quantified by flow cytometry (n=3, p≤0.01). Quantitative analysis of β3 integrin mRNA levels following treatment with siβ3 nanoparticles by real-time PCR (n=3, p≤0.01) in (C) NME and (D) MDA-MB-231 cells revealed RGD-targeted ECO/siRNA nanoparticles maintain gene silencing. E) Cellular uptake in NME cells, both with and without TGF-β stimulation (5 ng/mL; 72 hours), was quantified by flow cytometry for RGD-ECO/siRNA nanoparticles containing Alexa Fluor 488-labelled siRNA 4 hours after treatment. One group of TGF-β stimulated NME cells (TGF-β+ECO/siβ3) was treated with ECO/siβ3 nanoparticles at 100 nM siRNA for 48 hours prior to cellular uptake with the RGD-targeted nanoparticles to quantify the effect of β3 integrin silencing on targeted uptake (n=3, ±SE, *p≤0.05, **p≤0.01). For panels B-E, data represent mean±SE.
Figure 34B:
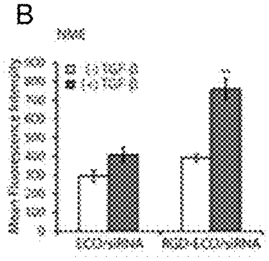
Figure 34C:
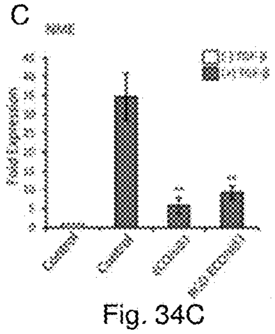
Figure 34D:
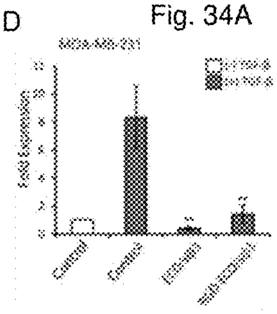
Figure 34E:
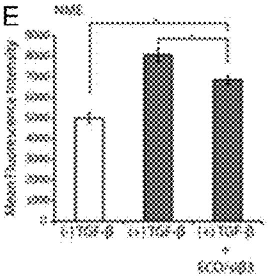
Figure 35A:
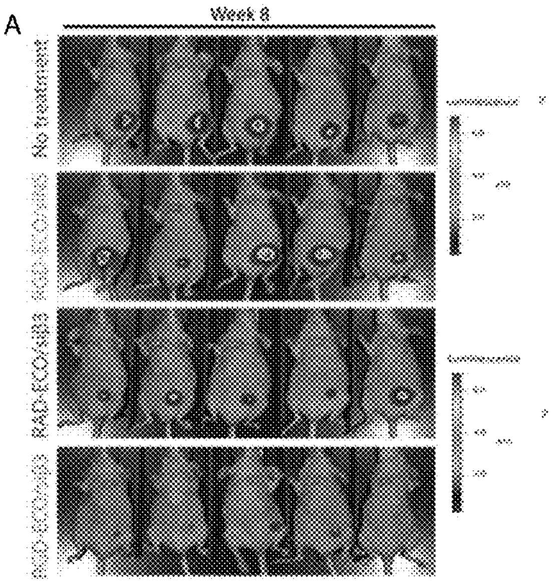
FIGS. 35(A-F) illustrate RGD-targeted ECO/siβ3 nanoparticles inhibited primary tumor growth and EMT in mice after systemic administration. A) and quantified by B) BLI (data represents mean±SE, n=5, *p≤0.05, **p≤0.01), and C) caliper measurements (data represents mean±SE, n=5, *p≤0.05, p≤0.01). D) Primary tumors were resected at week 9, and final tumor weights of the indicated treatment groups were obtained (data represents mean±SE, n=5, p≤0.01). E) Semi-quantitative real-time quantification of β3 integrin mRNA expression from resected primary tumors of the indicated groups (data represents mean±SE, n=5, **p≤0.01). F) H&E, DAPI and fibronectin immunostaining of the indicated primary tumors (scale bar, 300 μm).
Figure 35B:
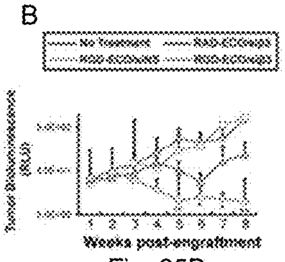
Figure 35C:
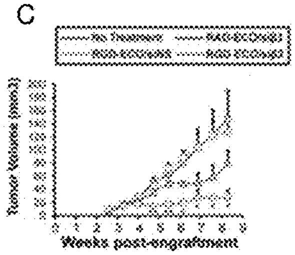
Figure 35D:
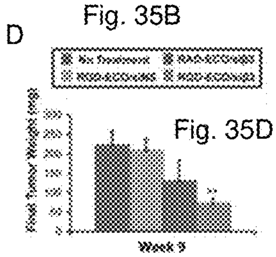
Figure 35E:
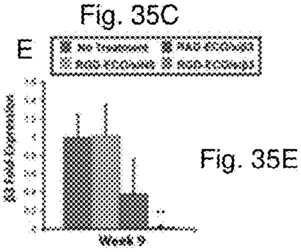
Figure 35F:
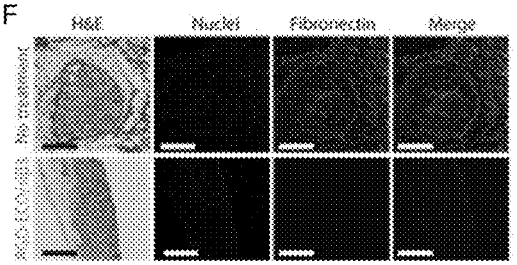

ECO/Siβ3 Nanoparticles Attenuate Outgrowth of Murine and Human MECs in 3D-Organotypic Culture To study the effects of ECO/siβ3 nanoparticles in a physiologically relevant system, we cultured NME and MDA-MB-231 cells in 3D-organotypic cultures to recapitulate the elastic modulus of a distant metastatic site such as the pulmonary microenvironment. This culture method presented additional obstacles in the delivery and uptake of nanoparticles, since these organoids were compact and surrounded by a dense matrix. Using confocal microscopy, we confirmed that ECO/siRNA nanoparticles formulated with fluorescently-labeled siRNA (AF-488) readily gained access to NME organoids by first penetrating into the periphery within 30 min after treatment, and further dispersing throughout the entirety of the organoid to reach a near-uniform distribution within 24 h (FIG. 33A). The dispersion of ECO/siRNA nanoparticles into the inner cell layers of the organoids suggests that ECO/siRNA uptake by these cells may result from diffusion through intercellular spaces or through transcytosis. FIGS. 33B and C show that NME and MDA-MB-231 organoids stimulated with TGF-β exhibited rapid growth as compared to their quiescent counterparts. Treatment with ECO/siβ3 nanoparticles inhibited the growth of both quiescent and TGF-β-stimulated NME and MDA-MB-231 organoids (FIGS. 33B and C) in comparison to treatment with ECO/siNS nanoparticles. These results demonstrate the effectiveness of ECO/siβ3 nanoparticles in attenuating the 3D outgrowth of post-EMT breast cancer cells.

Surface Modification of ECO/siRNA Nanoparticles with RGD Peptide Promotes Cellular Uptake and Sustains Gene Silencing An essential goal of in vivo siRNA delivery is to increase siRNA localization at the disease site while minimizing its accumulation in non-target tissues. We modified ECO/siRNA nanoparticles with RGD peptides via PEG spacers (3,400 Da), and examined their cellular uptake in both unstimulated and TGF-β-stimulated NME cells. TGF-β stimulation had no effect on the cellular uptake of unmodified ECO/siRNA nanoparticles, while cellular uptake of RGD-ECO/siRNA nanoparticles was robustly enhanced (FIG. 34), leading to effective silencing of β3 integrin in TGF-β-treated cells (FIG. 34). Since $\alpha_v\beta3$ is a major receptor that recognizes the RGD targeting peptide, we sought to determine whether 03 integrin silencing impacts cellular uptake of RGD-ECO/siRNA nanoparticles. Although cellular uptake of RGD-targeted nanoparticles was diminished upon β3 integrin silencing, uptake was nonetheless elevated consistently, because of the presence of other receptors for the peptide (FIG. 34). Taken together, these results show that RGD-targeted ECO/siRNA nanoparticles efficiently promote cellular uptake and robust gene silencing, particularly in post-EMT and metastatic breast cancer cells.

RGD-ECO/Siβ3 Nanoparticles Safely Inhibit Pulmonary Outgrowth of Mouse MECs In Vivo To address safety concerns, we examined the acute inflammatory response of intravenously injected PEGylated ECO/siRNA nanoparticles. We examined the acute inflammatory response of intravenously injected PEGylated ECO/siRNA nanoparticles, to address potential safety concerns. Compared to unmodified nanoparticles, PEGylated nanoparticles, which harbor a reduced surface zeta potential, attenuated the elevation of serum interleukin-6 (IL-6) and tumor necrotic factor-α (TNF-α) levels at 4 h post-injection, which were resolved within 24 h. To evaluate the effect of β3 integrin silencing on pulmonary outgrowth, we inoculated TGF-β-treated NME cells into the lateral tail vein of nude mice and subsequently monitored pulmonary outgrowth. Systemic injections of RGD-targeted ECO/siβ3 nanoparticles dramatically inhibited pulmonary outgrowth of post-EMT NME cells, as compared to non-specific RAD-ECO/siβ3 and RGD-ECO/siNS treatment groups. These results demonstrate that PEGylated ECO/siRNA nanoparticles exhibit a good safety profile for systemic siRNA delivery, and that RGD-targeted ECO/siβ3 nanoparticles with PEG spacers can effectively inhibit pulmonary outgrowth of TGF-β-stimulated NME cells, when targeted for in vivo delivery applications.

RGD-ECO/Siβ3 Nanoparticles Effectively Inhibit Primary Tumor Growth and Metastasis of Malignant Human MECs To further evaluate the in vivo effect of our targeted ECO/siβ3 nanoparticles, MDA-MB-231 cells pretreated with TGF-β were engrafted into the mammary fat pad of nude mice. Mice were treated with RGD-ECO/siβ3 (1.5 mg/kg siRNA) every 5 days, starting at day 17. Primary tumor burden was monitored by bioluminescence imaging (BLI) and caliper measurements. Compared to the untreated control, RGD-ECO/siNS or RAD-ECO/siβ3 treatment groups, RGD-ECO/siβ3 treated mice exhibited significantly reduced primary tumor burden (FIG. 35). The primary tumors were resected at week 9 (FIG. 35) and weighed. FIG. 35 shows that RGD-ECO/siβ3 treatment resulted in significantly reduced tumor weights as compared to the control groups. Importantly, the therapeutic efficacy of RGD-ECO/siβ3 was reflected by decreased mRNA expression of β3 integrin in the primary tumors, relative to that in the control groups (FIG. 35). RAD-ECO/siβ3 treatment resulted in marginally reduced 133 integrin expression (FIG. 35), which was consistent with the marginally reduced primary tumor burden, which were not statistically significant (FIG. 35). These data reflect partial uptake of the RAD-ECO/siβ3 nanoparticles by primary tumors as a result of passive tumor accumulation attributed to tumor vascular hyperpermeability. H&E staining of tissue sections demonstrated similar histopathological patterns in RGD-ECO/siβ3-treated and control groups, while untreated mice developed tumors that were more vascularized than RGD-ECO/siβ3-treated tumors. Further immunostaining of tissue sections indicated that RGD-ECO/siβ3-treated primary tumors exhibited decreased expression of the mesenchymal marker, fibronectin (FIG. 35), which is associated with poor overall survival.

Figure 36A:
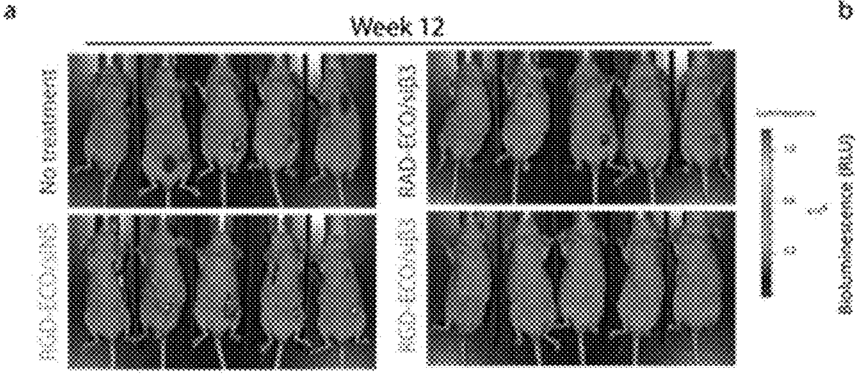
FIGS. 36(A-E) illustrate RGD-ECO/siβ3 nanoparticles inhibited breast cancer metastasis and primary tumor recurrence. A) BLI images of mice at week 12 revealed differences in metastasis and primary tumor recurrence for the different treatment groups after primary tumor resection on week 9. B) Quantification of primary tumor recurrence (data represents mean±SE, n=5, *p≤0.05). C) Quantification of thoracic metastasis by BLI (data represents mean±SE, n=5, *p≤0.05, **p≤0.01). Mice were released from ECO/siRNA therapeutic regimen at week 12. D) Representative BLI of mice on week 16.
Figure 36B:
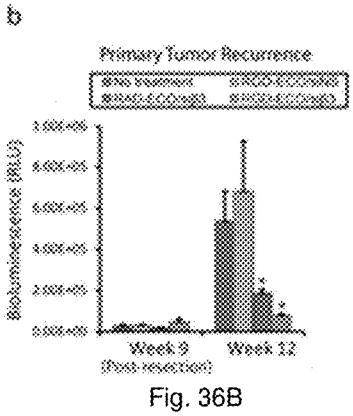
Figure 36C:
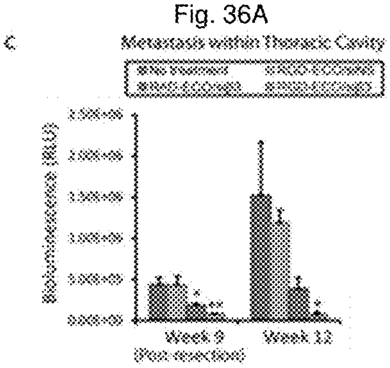
Figure 36D:
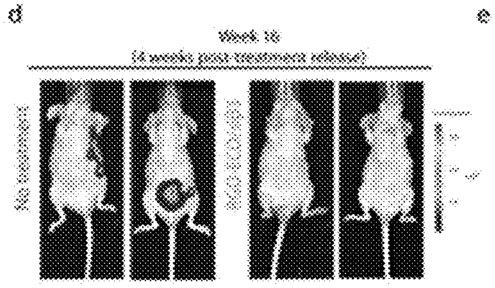
Figure 36E:
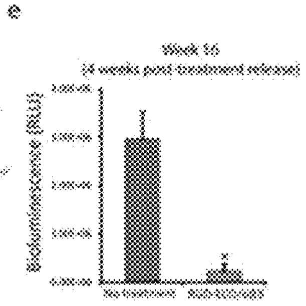

RGD-ECO/siβ3 treatment resulted in robust inhibition of tumor metastasis (FIGS. 36A and C) and primary tumor recurrence (FIG. 36B), as compared to control groups at week 12 post-engraftment. Interestingly, RAD-ECO/siβ3 treatment also mediated significant inhibition of tumor metastasis and primary tumor recurrence as compared to RGD-ECO/siNS treatment, but to a lesser extent than RGD-ECO/siβ3. This decrease in the efficacy of RAD-ECO/siβ3 could be attributed to the lack of specific targeting and binding of the nanoparticles to the cancer cells. At 12 weeks post-engraftment, the RGD-ECO/siβ3 group was released from nanoparticle treatment to evaluate the lasting effects of therapeutic β3 integrin silencing on tumor recurrence and metastasis in comparison with the untreated control group. At 4 weeks post-treatment release (16 weeks post-engraftment), the RGD-ECO/siβ3-treated mice remained tumor-free, while the tumor burden of untreated mice continued to increase (FIGS. 36D and E). Finally, throughout the entire course of treatment, no significant difference was observed in the body weights across the different treatment groups, demonstrating the low toxicity of the intravenously administered, targeted PEGylated ECO/siRNA nanoparticles. Collectively, these data highlight the safety and effectiveness of the systemic administration of RGD-ECO/siβ3 nanoparticles for the inhibition of TNBC tumor progression and metastasis.

The data demonstrates that the RGD-ECO/siβ3 nanoparticles constitute an effective targeted therapy to combat TNBC. Cancer metastasis involves a cascade of events, including EMT and local invasion, intravasation, survival in circulation, extravasation, and outgrowth of disseminated cells at the secondary site. In order to alleviate metastasis, it is essential to eliminate post-EMT cells and prevent their metastatic dissemination and outgrowth. Silencing EMT-related genes by RNAi has the potential to revolutionize current treatment standards. β3 integrin has been implicated as a powerful inducer of EMT, potentiating the oncogenic effects of TGF-β by inducing invasion and metastasis of MECs. Although functional disruption of β3 integrin was shown to attenuate TGF-β-mediated EMT and tumor progression, the utilization of β3 integrin siRNA as a therapeutic regimen was previously limited due to the lack of a clinically feasible approach. Here, we highlight how RGD-ECO/siβ3 nanoparticles inhibit TNBC metastasis by silencing the expression of β3 integrin. The inhibition of TGF-β-mediated EMT with ECO/siβ3 nanoparticles was evident by the obstruction of TGF-β-mediated morphological changes, downregulation of epithelial markers, and upregulation of mesenchymal markers. More importantly, the attenuated EMT phenotype, decreased invasiveness resulted in reduced outgrowth of breast cancer cells in 3D-cultures and in vivo, as well as abrogated metastatic dissemination, and subsequently decreased metastatic burden.

Example 5

In this Example, we developed a dual pH-sensitive and peptide-targeted siRNA delivery system. While various attempts have been made to create eIF4E therapies, siRNA-mediated strategies have yet to be employed in vivo. Furthermore, the effect of eIF4E silencing in a drug-resistant TNBC cell line has yet to be established or be translated into a viable systemically-administered therapeutic regimen. The inclusion of the acid-labile hydrazone bond within a peptide-targeted PEG moiety (RGD-PEG(HZ)-ECO/siRNA) created a pH-cleavable coating that sheds from the core ECO/siRNA nanoparticle in response to the acidic endolysosomal environment following uptake into tumor cells (FIG. 44). Once the core ECO/siRNA nanoparticle has been re-exposed, the intrinsic pH-sensitive amphiphilicity of ECO/siRNA nanoparticles enables endolysosomal membrane disruption and escape to achieve potent gene silencing. Accordingly, the pH-cleavable nanoparticles will be leveraged to silence eIF4E and resensitize drug-resistant TNBC to paclitaxel therapy.

Materials and Methods

Cell Culture

Human triple-negative breast cancer MDA-MB-231 cells expressing a luciferase reporter enzyme (MDA-MB-231-Luc) were obtained from ATCC (American Type Culture Collection) and cultured in Dulbecco's modified Eagle's media (Invitrogen) and supplemented with 10% fetal bovine serum (Invitrogen), 100 μg/mL streptomycin, and 100 unites/mL penicillin (Invitrogen). The cells were maintained in a humidified incubator at 37° C. and 5% $CO_2$. A paclitaxel-resistant subline of the MDA-MB-231 cell line (MDA-MB-231.DR) was induced by chronic exposure of MDA-MB-231 cells to 5 nM paclitaxel (PTX, Sigma Aldrich) with increasing concentration at each passage over 8 weeks to reach a final concentration of 20 nM. Initially, cells were maintained at 5 nM PTX with increasing concentration in increments of 5 nM after every other passage over 8 weeks to reach a final concentration of 20 nM. Once resistance to paclitaxel was confirmed, the MDA-MB-231.DR cells were maintained at 5 nM PTX.

Synthesis of mPEG(HZ)-Mal and RGD-PEG(HZ)-Mal

NHS-PEG-SH (MW 3400) and mPEG-HZ (MW 5000) were obtained from Nanocs, cRGDfk was obtained from Peptides International.

To synthesize the non-targeted, pH-cleavable PEG spacer, mPEG5000-hydrazide (Laysan Bio) was reacted with N-4-acetylphenyl maleimide (APM). First, 87.8 mg (MW=5000, 1 equivalent, 17.56 μmol) of the hydrazide-derivatized mPEG5000 was dissolved in 10 mL DCM/MeOH (50/50) and 100 mg Na2SO4 was added. Next, 11.7 mg (MW=215.2, 3.1 equivalent, 54.44 μmol) of APM was dissolved in 1 mL DCM/MeOH (50/50) and added dropwise into the mPEG-hydrazide solution. After the addition of APM, acetic acid (1.77 μL of 34% v/v solution in DCM, 0.6 equivalent, 10.54 μmol) was added. The reaction was stirred for 24 hours at room temperature under nitrogen. After 24 hours, the solution was precipitated into cold diethyl ether (3×) to obtain a purified product. The H1 NMR spectrum (Solvent: CDCl3) of mPEG5000 (HZ)-maleimide was used to confirm the correct structure using the following characteristic peaks: 8.43 (s, 1H, —NH—), 8.06 (d, 2H, in phenyl), 7.54 (d, 2H, in phenyl), 6.91 (2, 2H, two olefinic protons of maleimide), 3.48-3.58 (m, 438H, PEG).

A three-step reaction was used to synthesize the cRGD-targeted pH-cleavable PEG-hydrazone moiety. First, cRGDfk was first conjugated to the heterobifunctional NHS-PEG3400-SH: 25 mg (MW=603.7, 2 equivalent, 41.4 μmol) of c(RGD)fk was dissolved in 5 mL DMF. Cyclic (RGD)fk was used at 2× molar excess to the NHS-PEG3400-SH. Next, 70.4 mg (MW=3400, 1 equivalent, 20.7 μmol) of NHS-PEG3400-SH was dissolved in 1 mL of DMF and added drop-wise into the c(RGD)fk/DMF solution. After addition, 100 μL of DIPEA was added to the solution. The solution was stirred gently at room temperature for 4 hours. The solution was precipitated into an excess of diethyl ether (3×) to remove excess c(RGD)fk and obtain the purified cRGD-PEG3400-SH product. To ensure free thiol availability, 100 mg of dithiothreitol (DTT) was added to the solution and stirred overnight to reduce any disulfide bonds present in the synthesized cRGD-PEG-SH. Free DTT was removed using a desalting spin column (1.8K MWCO). The product was lyophilized, resuspended in chloroform and stored at −80° C. Conjugation of cRGD to PEG was confirmed by an observed shift of ~600 in the maldi-tof spectrum. To create a hydrazide-activated cRGD-PEG, 25.2 mg (MW≈4000, 1 equivalent, 6.3 μmol) of cRGD-PEG-SH was dissolved 5 mL chloroform and reacted with 4.25 mg (N-ε-maleimidocaproic acid) hydrazide (EMCH, MW=225.24, 3 equivalents, 18.9 μmol), 4.39 μL of trimethylamine was added to the reaction (TEA, 5 equivalents, 31.5 μmol). The reaction was carried out for 4 hours at room temperature under stirring. After, the reaction solution was purified using a spin column (1.8K MWCO). The product was lyophilized, resuspended in chloroform and stored at −80° C. For the final step, 12 mg cRGD-PEG(HZ) (1 equivalent, 2.84 μmol) was reacted with 1.2 mg N-4-acetylphenyl maleimide (APM, 2 equivalent, 5.68 μmol) overnight at room temperature under constant stirring. The reaction mixture was purified on a silica gel column using chloroform:methanol mobile phase (9:1 v/v). The final product was concentrated and lyophilized. The H1 NMR spectrum (Solvent: DMSO) of cRGD-PEG3400 (HZ)-maleimide was used to confirm the structure with the following characteristic peaks: 8.48 (s, 1H, —NH—), 8.0 (d, 2H, in phenyl), 7.6-7.8 (m, cRGD), 7.45 (d, 2H, in phenyl), 7.2 (2, 2H, two olefinic protons of maleimide), 3.1-3.5 (m, 304H, PEG).

Preparation of PEG-Modified ECO/siRNA Nanoparticles

The ECO lipid carrier was synthesized as described previously. ECO (MW=1023) was dissolved in 100% ethanol at a stock concentration of 2.5 mM for in vitro experiments and 50 mM for in vivo experiments. The siRNA was reconstituted in RNase-free water to a concentration of 18.8 μM for in vitro experiments and 25 μM for in vivo experiments. For in vitro experiments, an siRNA transfection concentration of 100 nM was used. ECO/siRNA nanoparticles were prepared at an N/P ratio of 8 by mixing predetermined volumes of ECO and siRNA for a period of 30 minutes in RNase-free water (pH 5.5) at room temperature under gentle agitation to enable complexation between ECO and siRNA. The total volume of water was determined such that the volume ratio of ethanol:water remained fixed at 1:20. For RGD-PEG(HZ)-modified ECO/siRNA nanoparticles, RGD-PEG(HZ)-Mal was first reacted with ECO in RNase-free water at 2.5 mol % for 30 minutes under gentle agitation and subsequently mixed with siRNA in RNase-free water for an additional 30 min RGD-PEG(HZ)-mal was prepared at a stock solution concentration of 0.32 mM in RNase-free water. Again, the total volume of water was determined such that the volume ratio of ethanol:water remained fixed at 1:20.

Nanoparticle Characterization

The zeta potential of unmodified, mPEG- and mPEG (HZ)-modified ECO/siRNA nanoparticle formulations at different pHs in PBS was determined with a Brookhaven ZetaPALS Particle Size and Zeta Potential Analyzer (Brookhaven Instruments). For each formulation, the nanoparticles were diluted in PBS solutions at pH 7.4, 6.5, or 5.4. The zeta potential measurement was taken at each indicated time point up to 4 hours. Data represents the mean of three independently conducted experiments.

pH-Dependent Membrane Disruption Hemolysis Measurement

The hemolytic activity was measured to determine the membrane-disruptive ability of unmodified, mPEG- and mPEG(HZ)-modified ECO/siRNA nanoparticle formulations at pH levels corresponding to various stages of intracellular trafficking. Red blood cells (RBCs) isolated from rats (Innovative Research Inc.) were diluted 1:50 in PBS solutions at pH 7.4, 6.5, and 5.4. ECO/siRNA nanoparticles were prepared at a volume of 150 μL and incubated with an equal volume of the various RBC solutions in a 96-well plate at 37° C. for 2 hours. Following incubation, samples were centrifuged and the absorbance of the supernatants was determined at 540 nm. Hemolytic activity was calculated relative to the hemolytic activity of 1% Triton X-100 (Sigma Aldrich), a non-ionic surfactant. Each pH was conducted in triplicate and the data presented represents the mean and standard deviation.

Flow Cytometry for Nanoparticle Cellular Uptake Measurements

Cellular uptake and intracellular delivery of various ECO/siRNA nanoparticle formulations include mPEG-maleimide, mPEG(HZ)-maleimide, RGD-PEG-maleimide, RGD-PEG (HZ)-maleimide were evaluated quantitatively with flow cytometry. The ECO/siRNA nanoparticle formulations were prepared with 25 nM AlexaFluor647-labeled siRNA (Qiagen). Approximately $2.5\times10^4$ MDA-MB-231 cells were seeded onto 12-well plates and grown for an additional 24 hours. The cells were transfected with each ECO/siRNA nanoparticle formulation in 10% serum media. After 4 hours, the transfection media was removed and each well was washed twice with PBS. The cells were harvested by treatment with 0.25% trypsin containing 0.26 mM EDTA, (Invitrogen) collected by centrifugation at 1000 rpm for 5 min, resuspended in 500 μL of PBS containing 5% paraformaldehyde, and finally passed through a 35 μm cell strainer (BD Biosciences). Cellular internalization of ECO/siRNA nanoparticles was quantified by the fluorescence intensity measurement of AlexaFluor 647 fluorescence for a total of 10,000 cells per each sample using a BD FACSCalibur flow cytometer. Each formulation conducted in triplicate and the data presented represents the mean fluorescence intensity and standard deviation.

For studying the endocytic trafficking pathway, the following inhibitors were used 1 hour prior to transfection in MDA-MB-231 cells with the various ECO/siRNA nanoparticles: 4° C., Cytochalasin D (5 μm/mL; Sigma Aldrich), Genistein (200 μM; Sigma Aldrich), and Nocadozole (20 μM; Sigma Aldrich). After 1 hour, the various ECO/siRNA nanoparticles formulated with the fluorescent AF647-labeled siRNA, as described above, were added to the cells. After an additional 2 hours, the cells were harvested and processed as described above. Similarly, cellular internalization of ECO/siRNA nanoparticles was quantified by the fluorescence intensity measurement of AlexaFluor 647 fluorescence for a total of 10,000 cells per each sample using a BD FACSCalibur flow cytometer. Each formulation was conducted in triplicate and the data presented represents the mean fluorescence intensity and standard deviation.

Confocal Microscopy of Nanoparticle Uptake and Intracellular Release of siRNA

Live cell confocal microscopy was used to assess the cellular uptake, endolysosomal escape, and intracellular release of siRNA. Approximately $1\times10^5$ MDA-MB-231 cells were seeded onto glass-bottom micro-well dishes. After 24 hours, the cells were stained for 30 minutes each with 5 μg/mL Hoechst 33342 (Invitrogen) and with 50 nM Lysotracker Green DND-26 (Molecular Probes). RGD-PEG- and RGD-PEG(HZ)-modified ECO/siRNA nanoparticles were formed at an N/P ratio of 8 and a 25 nM siRNA concentration with an AlexaFluor 647-labelled siRNA. Images were taken using an Olympus FV1000 confocal microscope while the cells were housed in a humidified weather station under 5% $CO_2$.

In Vitro Luciferase Silencing Efficiency

MDA-MB-231-Luc cells were seeded in 24-well plates at a density of $2\times10^4$ cells and allowed to grow for 24 hours. Transfections were carried out in 10% serum media with an N/P ratio of 8 and 100 nM anti-luciferase siRNA concentration (Dharmacon: sense sequence: 5'-CUUACGCUGAGUACUUCGAdTdT-3', anti-sense sequence: 5'-UCGAAGUACUCAGCGUAAGdTdT-3'). Following a 4 hour transfection period, the media was replaced with fresh serum-containing media and the cells continued to grow for up to 72 hours. For experiments using chloroquine (Sigma Aldrich), transfections were conducted in a similar manner either with or without 100 μM chloroquine. As above, following a 4 hour transfection period, the media was replaced with fresh serum-containing media and the cells continued to grow for up to 48 hours. At each time point for luciferase silencing experiments, the cells were rinsed twice with PBS and lysed using the reporter lysis buffered provided in the Promega Luciferase Assay kit. Following lysis, the cells were centrifuged at 10,000 g for 5 minutes and 20 μL cell lysate was transferred to a 96-well plate. To quantify luciferase expression, 100 μL Luciferase Assay Reagent was added to each well and the luminescence was read using a SpectraMax microplate reader (Molecular Devices). Luciferase activity was normalized to the total protein content measured from the cell lysate of each well using the BCA assay (Thermo Scientific). Data was presented relative to the control, which received no siRNA treatment.

In vivo Luciferase Silencing Efficiency

MDA-MB-231-Luc cells were engrafted into the mammary fat pad of female nude mice ($2\times10^6$ cells/mouse). Once the tumors reached an average of 250 $mm^3$, the mice were randomly sorted into 5 groups (n=3): 1) PBS control, 2) PEG-ECO/siLuc, 3) PEG(HZ)-ECO/siLuc, 4) RGD-PEG-ECO/siLuc, 5) RGD-PEG(HZ)-ECO/siLuc. All siRNA nanoparticle variations were formulated at 1.0 mg/kg siRNA in a total injection volume of 150 μL. All mice received a single intravenous tail vein injection of the various nanoparticle formulations following bioluminescent imaging on day 0. Expression of luciferase was quantified using bioluminescence imaging on day 0, 1, 3, 5, and 7. The bioluminescence signal intensity was quantified from a region of interest (ROI) placed over the tumor area. Data was normalized to the average signal intensity of day 0.

Fluorescence Molecular Tomography

Fluorescence imaging of siRNA accumulation within primary MDA-MB-231 mammary fat pad tumors was performed using the FMT 2500 quantitative fluorescence tomography system (Perkin-Elmer). Mice were treated with an intravenous tail vein administration of AlexaFluor 647-conjugated siRNA (1.0 mg/kg) with the various ECO nanoparticle formulations in a total injection volume of 150 μL. The mice were imaged before and after intravenous injection of the nanoparticles at 30 min, 1 h, 2 h, 4 h, 8 h, and 24 h.

Ex Vivo Flow Cytometry and Confocal Microscopy

Mice treated with AF 647-loaded ECO nanoparticles were sacrificed at 48 hours post-injection whereupon the primary tumor was resected and disaggregated into single cell suspensions using mechanical force and disaggregation solution as described previously. The cell suspension was stained with FITC-conjugated mouse MAb against human epithelial antigen (EpCAM) (HEA125; Miltenyi Biotec, Auburn, CA) in the dark and on ice for 10 minutes. After staining, the cells were washed and centrifuged, fixed with paraformaldehyde, and finally passed through a 35 μm cell strainer (BD Biosciences). Flow cytometry was conducted using the fluorescein channel for HEA-FITC and Cy5 channel for AF647-conjugated siRNA delivered by the ECO nanoparticles for a total of 10,000 cells per each sample using a BD FACSCalibur flow cytometer. Gating within the fluorescein channel was used to identify EpCAM (+) and EpCAM (−) populations. Each formulation was conducted in triplicate and the data presented represents the mean fluorescence intensity and standard deviation. Following flow cytometry, the cell suspensions were examined under an Olympus FV100 confocal microscope.

Semi-Quantitative Real-Time PCR Analyses

Real-time PCR studies were performed as described previously. Briefly, MDA-MB-231 or MDA-MB-231.DR cells (100,000 cells/well) were seeded overnight onto 6-well plates. The cells were then treated with ECO nanoparticles with a non-specific siRNA or eiF4E-specific siRNA (eIF4E: AAGCAAACCUGCGGCUGAUCU. At each indicated time point, total RNA was isolated using the RNeasy Plus Kit (Qiagen) and reverse transcribed using the iScript cDNA Synthesis System (Bio-Rad). Semi-quantitative real-time PCR was conducted using iQ-SYBR Green (Bio-Rad) according to manufacturer's recommendations. In all cases, differences in RNA expression for each individual gene were normalized to their corresponding GAPDH RNA signals. Primer sequences:

```
eIF4E:
Sense 5'- CTACTAAGAGCGGCTCCACCAC-3'

Antisense 5'- TCGATTGCTTGACGCAGTCTCC-3'

GAPDH
Sense 5'-ACGGATTTGGTCGTATTGGGCG-3';

Antisense 5'-CTCCTGGAAGATGGTGATGG-3'.
```

Western Blot Analyses

Immunoblotting analyses were performed as previously described. Briefly, MDA-MB-231 and MDA-MB-231.DR cells were seeded into 6-well plates ($1.5\times10^5$ cells/well) and allowed to adhere overnight. The cells were then treated with RGD-PEG(HZ)-ECO/siRNA complexes (N/P=8, siRNA concentration of 100 nM) in complete growth medium. After 5 days, detergent-solubilized whole cell extracts (WCE) were prepared by lysing the cells in Buffer H (50 mM β-glycerophosphate, 1.5 mM EGTA, 1 mM DTT, 0.2 mM sodium orthovanadate, 1 mM benzamidine, 10 mg/mL leupeptin, and 10 mg/mL aprotinin, pH 7.3). The clarified WCE (20 mg/lane) were separated through 10%

SDS-PAGE, transferred electrophoretically to nitrocellulose membranes, and immunoblotted with the primary antibodies, anti-eIF4E (1:1000; Abcam) and anti-β-actin (1:1000; Santa Cruz Biotechnology).

Cytotoxicity Assay

Cytotoxicity assays were performed in a 96-well plate as described previously, by seeding 2,000 MDA-MB-231 or MDA-MB-231.DR cells/well. First, RGD-PEG(HZ)-modified ECO/siRNA nanoparticles were used to transfect MDA-MB-231 or MDA-MB-231.DR with either siNS or sieIF4E for 48 hours. Next, the wells were washed twice with PBS and incubation with various concentrations of PTX in fresh media. After 2 additional days, the MTT reagent (Invitrogen) was added to the cells for 4 hours followed by the addition of SDS-HCl and further incubation for 4 hours. The absorbance of each well was measured at 570 nm using a SpectraMax spectrophotometer (Molecular Devices). Cellular viability was calculated as the average of the set of triplicates for each PTX concentration and was normalized relative to the no treatment control. Drug resistance was confirmed with an MTT assay to determine the $IC_{50}$ of paclitaxel. The $IC_{50}$ was defined as the dose of drug required to inhibit cell viability by 50%.

In Vivo Tumor Growth Inhibition Study

For in vivo anti-tumor efficacy studies, MDA-MB-231.DR cells ($2\times10^6$ cells/mouse) were inoculated in the mammary fat pads of female nu/nu mice. When the tumors reached and average of 150 $mm^3$, the mice were randomly sorted into 4 groups (n=5): 1) PBS control, 2) RGD-PEG(HZ)-ECO/siNS (1.5 mg/kg siRNA)+PTX (5 mg/kg), 3) RGD-PEG(HZ)-ECO/sieIF4E (1.5 mg/kg siRNA)+PTX (5 mg/kg), 4) RGD-PEG(HZ)-ECO/sieIF4E (1.5 mg/kg siRNA). RGD-PEG(HZ)-ECO/siRNA nanoparticles were administered by intravenous injection into the lateral tail vein while PTX was administered in 10% DMSO/PBS with an intraperitoneal injection. Tumor growth was monitored by BLI and tumor size was monitored with caliper measurements. Three days after the final treatment, the mice were sacrificed to harvest tumor tissues.

Bioluminescent Imaging

Longitudinal imaging of the mice was performed using the Xenogen IVIS 100 imaging system. D-luciferin (Xenogen) was dissolved in PBS (15 mg/mL), and 200 μL of the luciferin stock solution (15 mg/mL) was injected i.p. 5 minutes before measuring the light emission. Mice were anesthetized and maintained under 2.5% isoflurane. Bioluminescent signals were quantified using Living Image software (Xenogen) by drawing an ROI over the tumor area.

Immunofluorescence and Immunohistochemical Staining

For immunohistochemistry, primary tumor samples were embedded in optimum cutting temperature (O.C.T.) compound (Tissue-TeK; Torrence, CA) in preparation for cryostat sectioning and immediately frozen. The samples were then sectioned, fixed in paraffin, and maintained at −80° C. The samples were stained with H&E to evaluate the presence of tumor tissue. Briefly, the samples were fixed in 10% formalin, rehydrated in 70% ethanol and rinsed in deionized water prior to hematoxylin staining. Samples were then rinsed in tap water, decolorized in acid alcohol, immersed in lithium carbonate and rinsed again in tap water. Next, the eosin counterstain was applied and slides were dehydrated in 100% ethanol, rinsed in Xylene and finally mounted on a coverslip with Biomount.

For immunofluorescence detection of eIF4E (Abcam: ab1126), survivin (Abcam: ab76424), Cyclin D1 (Abcam: ab16663), and VEGF (Abcam: ab46154), the paraffin-embedded slides were first deparaffinized using a series of washes in xylene and decreasing concentrations of ethanol. Heat-induced antigen retrieval was performed using a pressure cooker in sodium citrate buffer (10 mM Sodium citrate, 0.05% Tween 20, pH 6.0) for 20 minutes. Following heat-induced antigen retrieval, the samples were blocked in TBST solution containing donkey serum and washed three times with TBST. The primary antibody was applied at dilution of 1:100 in blocking solution for 1 h followed by three rinses with TBST. The Alexa Fluor 647 secondary antibody (Abcam: ab150079) was applied at a dilution of 1:1000 in blocking solution for 1 h followed by three washes with TBST and counterstained with DAPI at a dilution of 1:2500 in blocking solution. After washing with TBST and mounting in an anti-fade mounting solution (Molecular Probes), the samples were imaged using a confocal microscope.

Toxicity, Immune Response, and Pathology Studies

Female BALB/c mice (Jackson Laboratories) were used to study the toxicity and immune response of systemic treatment with ECO/siRNA and RGD-PEG(HZ)-ECO/siRNA nanoparticles. Following 1, 3 and 5 injections (n=5 for each amount of injections) spaced 5 days apart, blood was collected at 2 h and 24 h post-injection. Plasma was isolated from blood samples using Microtainer tubes (Becton Dickinson). To measure plasma cytokine levels, TNFα, IL-6, IL1-2, INFγ were quantified by ELISA according to the manufacturer's instructions (Invitrogen).

Statistical Analyses

Statistical values were defined using unpaired Student's t-test, with $p<0.05$ considered to be statistically significant.

Results

Figure 37A:
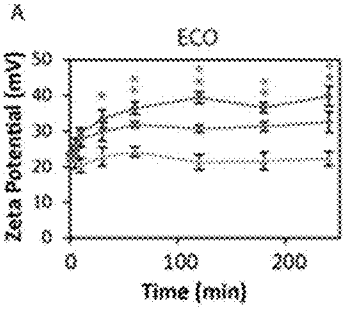
Figure 37B:
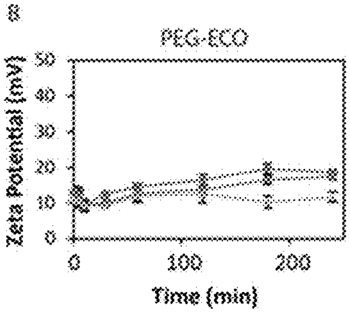

Surface Modification of ECO/siRNA Nanoparticles with pH-Cleavable PEG Layer Restores Intrinsic pH-Sensitive Activity The chemical structure of ECO contains various amino groups such that it carriers a net positive charge at neutral pH. These amine groups electrostatically complex with the siRNA cargo and contribute towards the pH-sensitive amphiphilic characteristic of the delivery system. The amino groups, across a range of pKa's, become protonated in an acidic environment to promote pH-dependent membrane disruption to allow for endolysosomal escape. At an N/P ratio of 8, ECO/siRNA nanoparticles exhibit a zeta potential of 22.3±1.73 mV at neutral pH. With increasing acidity, unmodified ECO/siRNA nanoparticles exhibit a pH-sensitive and time-dependent increase in zeta potential correlating to the protonation of the cationic ethylenediamine head group (FIG. 37A). This protonation is hypothesized to enhance the electrostatic interactions between the ECO carrier and the anionic membrane lipids to promote bilayer destabilization to enable escape into the cytosol. It was observed that modification of the siRNA nanoparticle surface with mPEG3400 at a 2.5 mol % through thiol-maleimide chemistry decreased the overall zeta potential to 12.3±1.39 mV (FIG. 37B). While unmodified ECO/siRNA nanoparticles exhibited pH-sensitivity at pH 6.5 and 5.4, this behavior was attenuated in PEG-modified nanoparticles. After 4 hours of incubation in PBS solutions at pH 6.5 and 5.4, PEGylated ECO/siRNA nanoparticles carried a zeta potential of 17.4±1.1 mV and 18.6±2.9 mV, respectively, compared to 32.5±2.7 mV and 39.8±3.1 mV for unmodified ECO/siRNA nanoparticles. This suggests that the surface aqueous phase formed by PEGylation may impede the protonation of the cationic head group. This was confirmed with the observation that the pH-sensitivity is further diminished towards neutrality by increasing the PEG surface density to 10 mol % (FIG. 46).

Figure 37C:
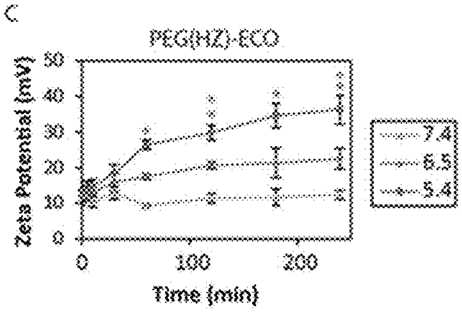

The insertion of the acid-labile hydrazone linkage within the PEG moiety created a pH-cleavable PEG layer to restore the pH-sensitivity of the core ECO/siRNA nanoparticles (FIG. 37C). Hydrazone is a well-characterized linkage known to hydrolyze at pH levels corresponding to the environment of the endolysosomal compartments. The hydrolysis of hydrazone occurs when the —C═N nitrogen is protonated causing a nucleophilic attack of water and the ultimate cleavage of the C—N bond. Previously, the hydrazone linkage has found popularity as a means to conjugate chemotherapeutics, such as doxorubicin, to a wide array of drug delivery systems and prodrugs to enhance intracellular release. This particular hydrazone-modified PEG linkage has also been used previously to create PEG(HZ)-phosphatidylethanolamine conjugates capable of forming micelles. The hydrazone-based micelles were found to be stable at physiological pH but highly sensitive to mildly acidic pHs, resulting in robust degradation of micelles at pH 5.5. Similarly, the observed increase in zeta potential at pH 6.5 and 5.4 presumably corresponds to the acid-catalyzed hydrolysis of the hydrazone linkage and subsequent shedding of the PEG layer whereupon the cationic ECO/siRNA core nanoparticle surface is exposed. Once exposed, the ethylenediamine head group within the ECO/siRNA nanoparticles becomes protonated. At pH 7.4, the zeta potential remains constant at ~12 mV indicating that the PEG layer remains intact as a result of the hydrazone linkage stability. Importantly, the stability of surface charge at pH 7.4 suggests the ECO/siRNA nanoparticles will remain PEGylated within the bloodstream at the normal physiological pH. Following exposure to pH 5.4, the hydrazone bond is degraded to remove the PEG layer. In turn, the surface zeta potential of PEG(HZ)-ECO/siRNA nanoparticles gradually increases and after 4 hours is similar to that of the unmodified ECO/siRNA nanoparticles, 36.3±1.9 mV and 39.8±2.8 mV, respectively. However, the time to reach the maximum zeta potential is prolonged, possibly due to the slower kinetics involved with the hydrolysis of the hydrazone linkage.

We have previously shown that the protonation of the cationic head group of ECO is directly coupled with the ability to induce pH-sensitive membrane disruption, a key step for successful and efficient cytosolic delivery of siRNA. To compare the effect of pH-cleavable to non-cleavable PEGylation, we examined the pH-sensitive hemolytic activity of ECO/siRNA nanoparticles modified with both PEGylation strategies (FIG. 38). Non-cleavable PEG-ECO/siRNA nanoparticles had a significantly lowered ability to induce hemolysis at pH 6.5 and 5.4 compared to unmodified ECO/siRNA nanoparticles. Again, this is indicative of the PEG layer inhibiting the interactions with the lipid membrane of the blood cells and also the protonation of the cationic head group of ECO. In alignment, increasing the PEG surface density further inhibited the hemolytic activity of the non-cleavable PEGylated nanoparticles. Conversely, the pH-cleavable PEG(HZ)-ECO/siRNA nanoparticles induced pH-sensitive hemolysis on par with unmodified ECO/siRNA nanoparticles. As the hemolytic activity was evaluated 2 hours following exposure of the red blood cells to the nanoparticles, both formulations of nanoparticles would have reached similar levels of protonation, as observed in FIGS. 37A and C, indicating the cleavage of the hydrazone linkage and subsequent shedding of the PEG layer.

pH-Cleavable RGD-PEG Modification Induces Potent In Vitro Silencing Efficiency

Figure 39A:
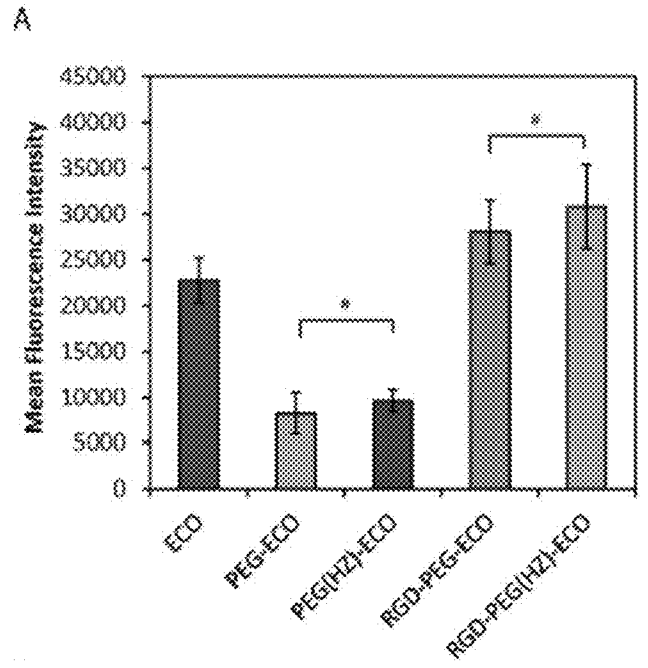

To facilitate ligand-specific uptake of the ECO/siRNA nanoparticles into the target population of cells, a cyclic-RGD (RGD) peptide was conjugated to both pH-cleavable and non-cleavable PEG moieties. Cellular uptake into MDA-MB-231 human breast cancer cells was quantified using flow cytometry with nanoparticles formulated with fluorescently labelled siRNA (FIG. 39A). The inclusion of the hydrazone linkage in both RGD-targeted and non-targeted ECO/siRNA nanoparticles had no significant difference in the ability of the nanoparticles to gain internalization into the cells when compared to the non-cleavable counterparts. Unmodified ECO/siRNA nanoparticles exhibited robust cellular uptake due to strong ionic interactions with the anionic cellular membrane. PEGylation endows neutrality to the nanoparticle surface and impedes such interactions with the cell surface. The addition of the RGD targeting peptide enhanced the cellular uptake and internalization due to specific binding of the RGD peptide to the $\alpha_v\beta_3$ integrin known to be present on the cellular surface of the MDA-MB-231 cells.

Surface modification of nanoparticles has been shown to influence the endocytic mechanism through which they are internalized by cells. Further, the endocytic mechanism can dictate the fate of nanoparticles within the intracellular trafficking pathways. By using a series of known pharmacological inhibitors of various endocytic pathways, the primary mechanism of uptake was elucidated for the various formulations of ECO/siRNA nanoparticles in MDA-MB-231 cells: 1) incubation of cells at 4° C. to inhibit energy-dependent endocytic mechanisms, 2) cytochalasin D is generally classified as an inhibitor of macropinicytosis/phagocytosis but recently has been implicated with inhibition of clathrin- and caveolae-mediated pathways, 3) Genistein inhibits caveolae-mediated endocytosis and 4) Nocodazole inhibits clathrin-mediated pathways. PEGylated ECO/siRNA nanoparticles were found to be internalized primarily via clathrin-mediate endocytosis while RGD-targeted nanoparticles entered primarily via caveolae-mediated endocytosis. Interestingly, unmodified ECO/siRNA nanoparticles were found to rely on both energy-dependent and independent mechanisms suggesting that the ECO lipid may be able to directly fuse with the phospholipid membrane of cells. Nanoparticles internalized by Clathrin- and caveolae-dependent mechanisms are often transferred to the lysosomes for degradation, therefore, the ability of both RGD-targeted and non-targeted nanoparticles to escape from the endolysosomal pathway is an important step for achieving gene silencing. No significant difference was observed in endocytic pathways between pH-cleavable and non-cleavable surface modifications.

Figure 39B:
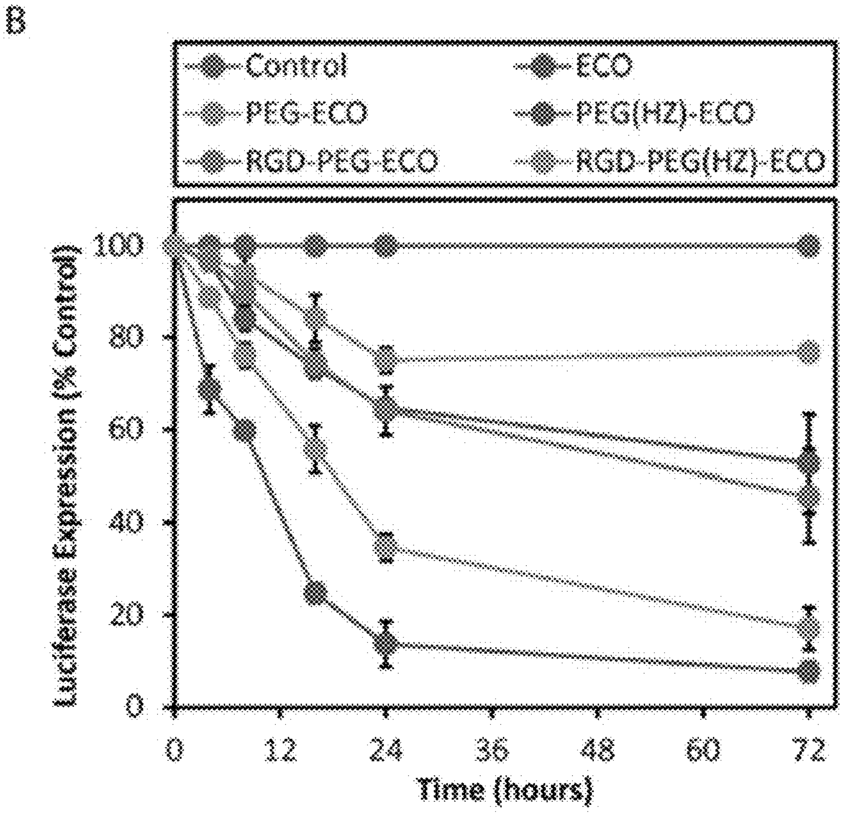

The in vitro luciferase silencing efficacy of the surface modified ECO/siRNA nanoparticles was evaluated in the MDA-MB-231-Luc cell line (FIG. 39B). We have shown that unmodified ECO/siRNA nanoparticles induce potent and sustained gene silencing upwards of 95% due to their ability to readily become internalized, escape from the endolysosomal pathway, and release the cargo siRNA into the cytosol. Accordingly, ECO/siRNA nanoparticles achieved 92.33±2.08% luciferase silencing 72 hours post-treatment in MDA-MB-231-Luc cells. The luciferase silencing efficiency was significantly inhibited upon non-cleavable PEGylation of the nanoparticles (PEG-ECO/siRNA) to only 23.45±1.52% after 72 hours. While decreased cellular uptake contributes to the attenuated silencing efficiency, our hemolysis assay data suggests PEGylation also interferes with the ability of the nanoparticles to escape from the endolysosomal pathway (FIG. 38). Indeed, the silencing efficiency significantly increased to 47.86±10.59% when the pH-cleavable PEG was used when compared to PEG-ECO/siRNA. This observation was highlighted with the addition of the RGD targeting peptide. Non-cleavable RGD-PEG-ECO/siRNA nanoparticles only achieved 54.17±10.01% luciferase silencing while the pH-cleavable RGD-PEG(HZ)-ECO/siRNA formulation reached 83.64±4.58% luciferase silencing 72 hours post-treatment.

Inclusion of Hydrazone Linkage Enhances Endosomal Escape

Figure 39C:
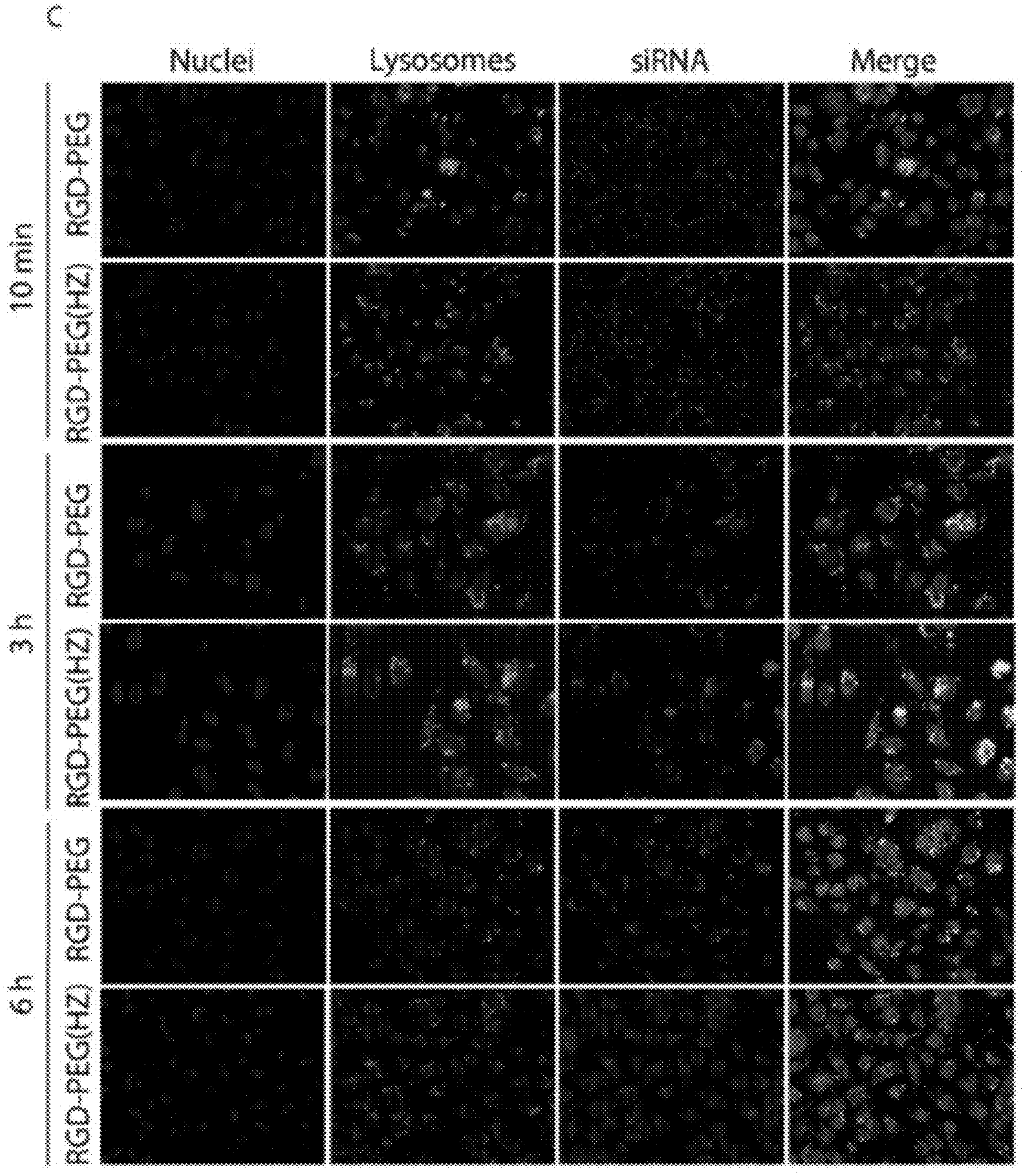

The ability of the hydrazone linkage to enable successful endolysosomal escape was confirmed through live cell confocal imaging (FIG. 39C). MDA-MB-231 cells were transfected with pH-cleavable and non-cleavable RGD-targeted ECO nanoparticles formulated with a fluorescently labelled siRNA (red) while co-stained with Lysotracker (green) to visualize the acidic compartments of the endosomes and lysosome Images taken after 10 minutes reveal that both RGD-targeted nanoparticle formulations have similar interactions with the cellular membranes. At 3 hours, both formulations exhibit strong co-localization (yellow) with the late endosomes and lysosomes, consistent with the intracellular trafficking of caveolae-mediated endocytosis. However, 6 hours post-treatment, the non-cleavable RGD-targeted nanoparticles appear contained within the endolysosomes as evident by the co-localization of the siRNA and Lysotracker fluorescent signal. In contrast, the pH-cleavable RGD-targeted nanoparticles appear to have successfully escaped from the endolysosomal pathway. Minimal co-localization of the siRNA and Lysotracker signal is observed and the dispersed siRNA signal within the cytosol indicates the siRNA has been released from the nanoparticles, as seen with unmodified ECO/siRNA nanoparticles. The inability of the non-cleavable RGD-targeted nanoparticles to escape into the cytosol further validates the observed discrepancy in gene silencing efficiency when compared with the pH-cleavable counterpart (FIG. 39C).

The endosomolytic agent chloroquine that causes endosome rupture and content release into the cytosol was used to further verify the role the hydrazone linkage plays in promoting escape. For both targeted and non-targeted nanoparticles, the silencing efficiency of pH-cleavable nanoparticles was not affected by chloroquine whereas non-cleavable nanoparticles exhibited a significantly enhanced silencing efficiency. The data suggests that upon treatment with chloroquine, complexes modified with the non-cleavable PEG that were trapped within endolysosomes were then freed into the cytosol while nanoparticles modified with the pH-cleavable PEG moiety had already escaped from the endolysosomes.

Figures 40A, 40B, 40C, 40D:
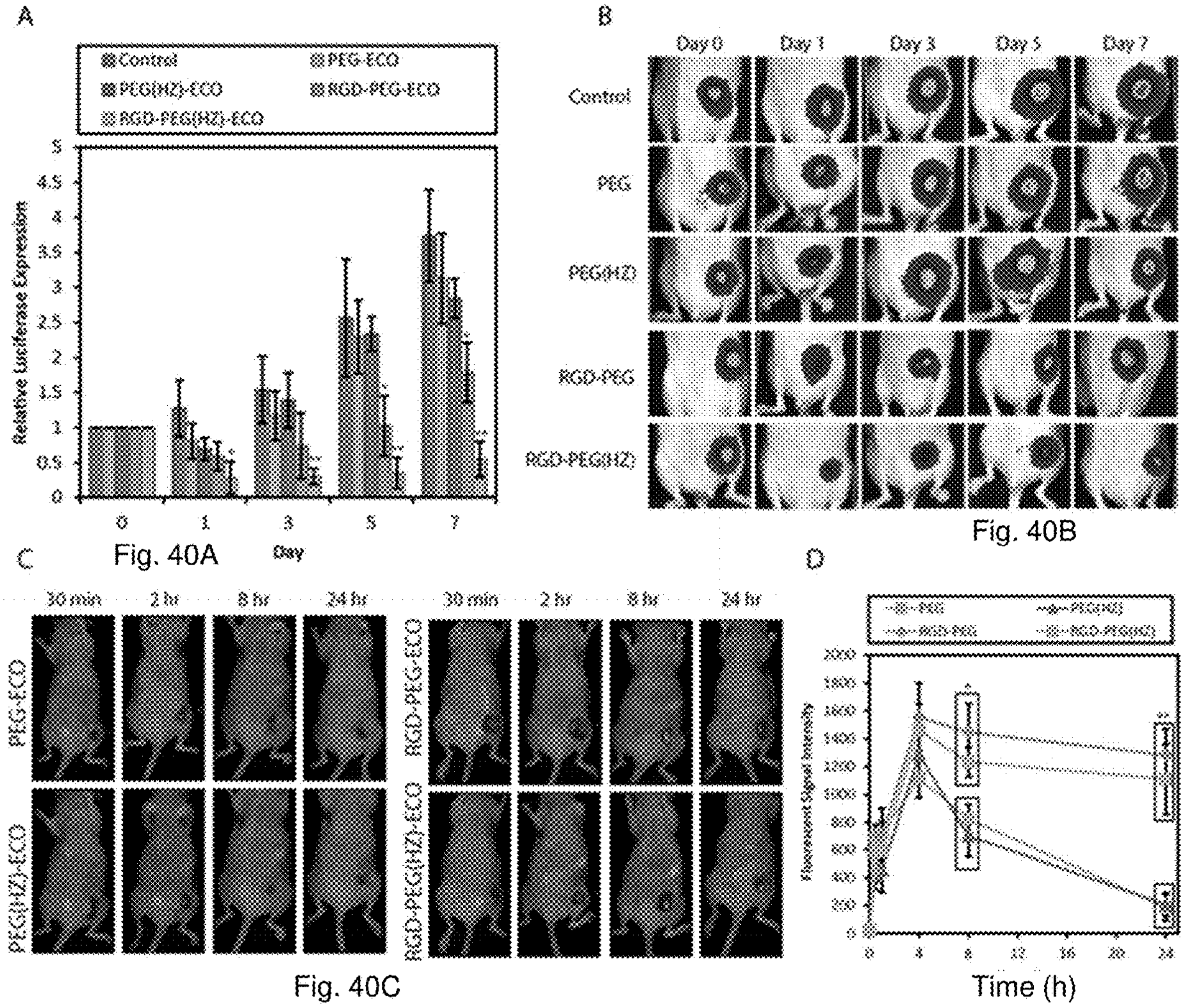

Targeted pH-Sensitive Nanoparticles Exhibit Potent and Sustained In Vivo Gene Silencing To study differences in the in vivo gene silencing efficiency of the developed pH-cleavable surface modification strategy, the delivery of anti-luciferase siRNA (1.0 mg/kg) following a single systemic administration was investigated using bioluminescent imaging in a primary mammary fat pad MDA-MB-231 breast cancer tumor model (FIGS. 40A and B). Unlike the in vitro luciferase silencing findings, the non-targeted ECO/siRNA nanoparticles, both pH-cleavable and non-cleavable formulations, had a negligible silencing effect on luciferase expression, suggesting minimal cellular uptake of the siRNA into the tumor cells. In contrast, both RGD-targeted formulations induced luciferase silencing to varying degrees for up to 7 days: the non-cleavable RGD-targeted ECO achieved 52.04% luciferase silencing while the pH-cleavable RGD-targeted formulation achieved 85.17% silencing compared to the no treatment control on day 7. This trend is consistent with the enhancement of silencing efficiency observed in vitro (FIG. 39C).

Targeting Ligand Enhances Tumor Retention of Nanoparticles by Promoting Internalization within Tumor Cells The tumor localization and subsequent delivery of functional siRNA following systemic administration of the various siRNA nanoparticle formulations was investigated. Fluorescence molecular tomography (FMT) enabled the analysis of tumor accumulation and retention of the nanoparticle-delivered siRNA over time. Mice received a single systemically administered dose of fluorescently-labeled siRNA (AF 647) delivered by the various surface modified ECO/siRNA nanoparticle formulations. Recent studies have demonstrated that the presence of a targeting ligand does not necessarily impact the initial tumor accumulation of the nanomedicine delivery system, but rather may facilitate tumor cell targeting resulting in longer tumor retention. In alignment, longitudinal FMT imaging studies revealed that the initial tumor localization of siRNA delivered by the targeted and non-targeted nanoparticles was not significantly different for the first 4 hours following systemic administration (FIGS. 40C and D). By 8 hours however, RGD-targeted nanoparticles were observed to accumulate within the tumor to a greater extent than the non-targeted formulations, regardless of whether the PEG modification was pH-cleavable or not. At 24 hours, both RGD-targeted nanoparticle formulations were retained within the tumor while the non-targeted formulations appeared to be washed out, due in part to the inability of the non-targeted nanoparticles to promote cellular internalization, as evident by the minimal presence of siRNA signal from the tumor ROI.

Active targeting of the ECO/siRNA nanoparticles using the RGD peptide may aid in the specific selection of cancer cells within the tumor site and promote internalization of the nanoparticles to a greater extent inside the target cells compared to non-target cells. To evaluate if selective uptake dependent upon cell type occurred, ex vivo flow cytometry was used to quantify siRNA internalization to study differences in cellular uptake of the targeted and non-targeted nanoparticles between human tumor and murine stromal cells. At 48 hours, tumors from the systemically treated mice were excised, disaggregated into single cell suspensions, and stained for the epithelial cellular adhesion molecular (EpCAM) using HEA-FITC to distinguish between the human MDA-MB-231 cancer cells and the murine stromal cells. FACS analysis of the cell suspensions in the FITC channel revealed two distinct cellular populations: EpCAM (+), human cancer cells and EpCAM (−), murine stromal cells. Gating for EpCAM (−) cells in the AlexaFluor 647 channel revealed a minimal shift in fluorescence between both targeted and non-targeted nanoparticle formulations compared to the PBS negative control. A distinct shift was observed in EpCAM (+) cells for targeted nanoparticles compared to both the non-targeted and PBS control groups, suggesting that the RGD-targeted nanoparticles are internalized more efficiently and preferentially by the human cancer cells. Contour plots highlight the two distinct EpCAM (+) and EpCAM (−) cellular populations. While the siRNA signal from non-targeted nanoparticle formulations was evenly distributed throughout both populations, the siRNA signal in EpCAM (+) cells was markedly higher for the RGD-targeted nanoparticle formulations. No difference was observed between pH- and non-cleavable formulations (data not shown).

Following flow cytometry, the cell suspensions were observed under a confocal microscope. Microscopy analysis revealed both pH-cleavable and non-cleavable RGD-targeted nanoparticle formulations were readily internalized by EpCAM (+) cells whereas the non-targeted formulations showed minimal uptake. While the targeted ECO/siRNA nanoparticles did not initially transport the siRNA cargo to the tumor site more efficiently than non-targeted nanoparticles according to the FMT data (FIG. 40D), it appears that RGD peptide enabled cell-specific recognition and internalization of the siRNA. The enhanced cellular uptake correlated to the prolonged retention of fluorescent signal within the tumor ROI as determined by FMT (FIG. 40D) and also the sustained luciferase silencing efficiency of the targeted nanoparticles (FIGS. 40A and B). As internalization of siRNA from pH-cleavable and non-cleavable RGD-targeted nanoparticle formulations appeared similar according to FMT and ex vivo confocal microscopy, the improvement in silencing efficiency of the pH-cleavable formulation may be a direct result of enhanced endolysosomal escape.

A surface modification strategy that combines PEGylation and active targeting not only allows the ECO/siRNA nanoparticles to retain stealth properties during circulation and accumulate at the tumor site by passive targeting, but the PEG shielding moiety provides a tether for versatile incorporation of various active targeting ligands. When further combined with the pH-cleavable hydrazone linkage, the developed surface modification strategy may significantly improve the therapeutic efficacy of the ECO/siRNA nanoparticle delivery system compared to the non-targeted and non-cleavable systems. Taken together with the in vivo luciferase silencing data, the differences in silencing efficiency across all formulations suggest: i) targeted nanoparticles are internalized to a greater extent by the tumor cells and ii) once internalized, formulations with the pH-cleavable PEG modification are more effective in delivering siRNA into the cytosol due to enhanced endolysosomal escape.

Silencing eIF4E by RGD-Targeted pH-Cleavable PEG-Modified ECO/siRNA Nanoparticles Enhances Sensitivity to Paclitaxel in a Drug-Resistance Triple-Negative Breast Cancer Cell Line The ability of the pH-cleavable RGD-PEG(HZ)-ECO/siRNA nanoparticles to mediate knockdown of eIF4E mRNA and protein was next evaluated in vitro. To study the therapeutic consequence of eIF4E downregulation on drug-resistant breast cancer cells, a paclitaxel-resistant subline of the MDA-MB-231 cell line (MDA-MB-231.DR) was induced by chronic exposure of MDA-MB-231 cells to paclitaxel. Interestingly, PTX-resistant cells were found to upregulate eIF4E expression (FIGS. 41A and B). While a widely used chemotherapeutic agent, PTX has been shown to activate signaling pathways that both promote and inhibit cell death. Normally, binding of 4E-BP1 to eIF4E will prevent eIF4E from binding to eIF4G and initiating cap-dependent translation. PTX has been found to diminish the suppressive role of 4E-BP1 through hyperphosphorylation to reduce the association affinity with eIF4E and promote its release. By doing so, eIF4E activity is elevated through a regained association with eIF4G and initiation of translation. Along these lines, treatment of MDA-MB-231 cells with PTX has been demonstrated elsewhere to also increase eIF4E expression in a dose-dependent manner Importantly, treatment of both cell lines with sieIF4E delivered by targeted and pH-cleavable nanoparticles was able to sustain potent eIF4E mRNA and protein silencing for upwards of 5 days. Nanoparticles delivering a non-specific siRNA induced no significant downregulation of eIF4E expression suggesting that all silencing activity was due to the siRNA and not the ECO carrier.

Figure 41C:
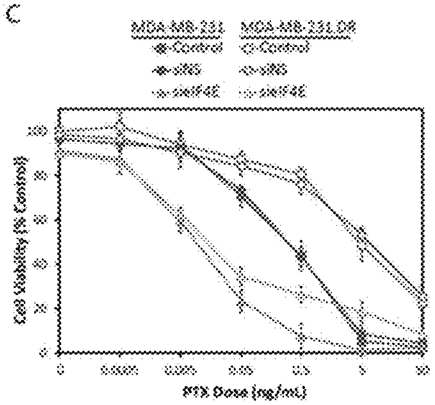

The therapeutic response of eIF4E silencing on enhancing the sensitivity of breast cancer cells to paclitaxel was determined by quantifying the cell viability after a combination of eIF4E silencing by the siRNA nanoparticles followed by treatment with PTX (FIG. 41C). Cells were first treated with RGD-PEG(HZ)-ECO/siRNA nanoparticles for 48 hours followed by treatment with varying concentrations of PTX for an additional 48 hours. For all conditions, cell viability decreased in a PTX concentration-dependent manner. The acquisition of resistance to PTX in the MDA-MB-231.DR subline was evident by a shift in the dose-response curve and the $IC_{50}$. A clear re-sensitization of MDA-MB-231.DR cells to PTX was observed when eIF4E was downregulated using siRNA delivered by RGD-PEG(HZ)-ECO/siRNA nanoparticles. For example, at 0.5 ng/mL PTX, treatment with PTX alone induced 44.6±6.6% viability in MDA-MB-231 cells and 80.7±2.9% viability in the drug-resistant subline. When coupled with silencing of eIF4E, viability dropped to 7.5±5.4% and 26.3±3.6% in MDA-MB-231 and MDA-MB-231.DR, respectively, using the same concentration of PTX.

Figure 42A:
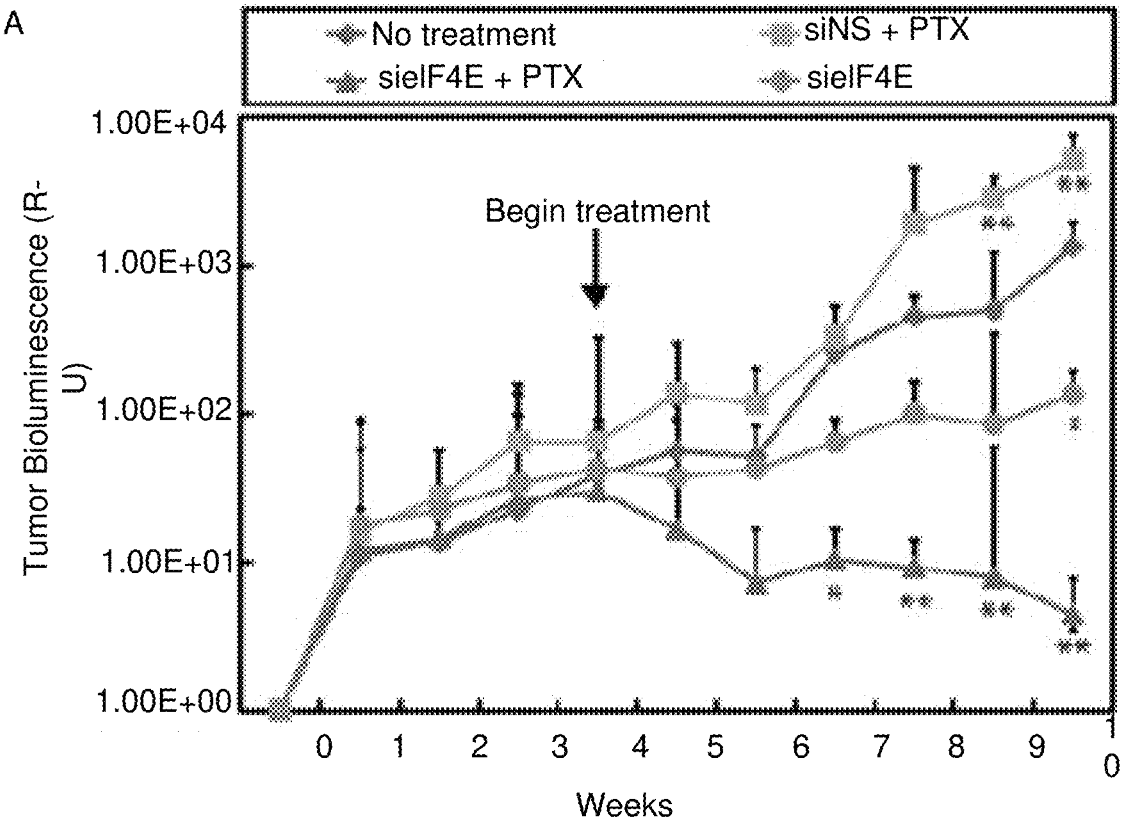
Figure 42B:
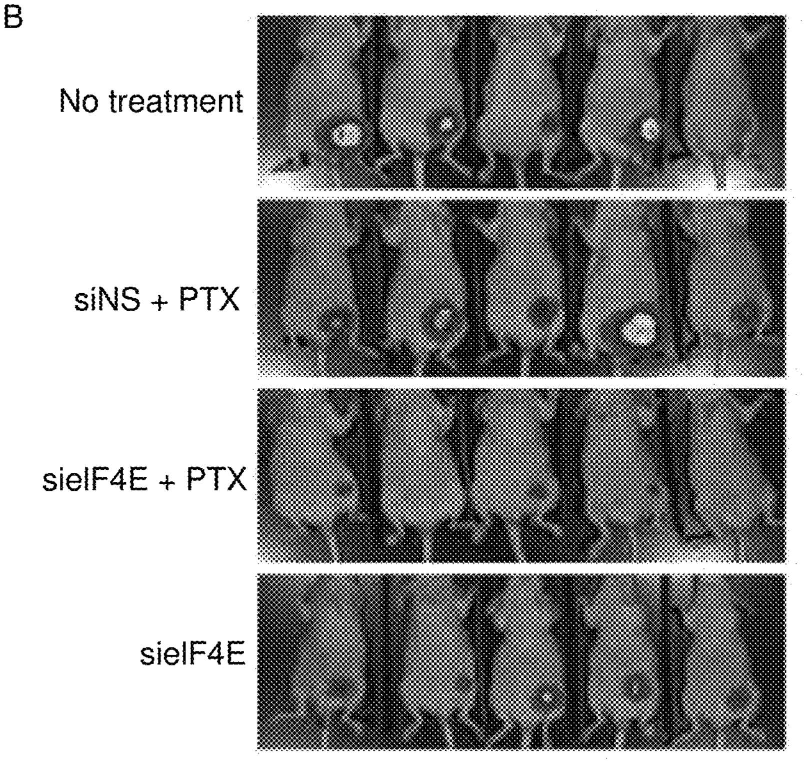
Figure 42C:
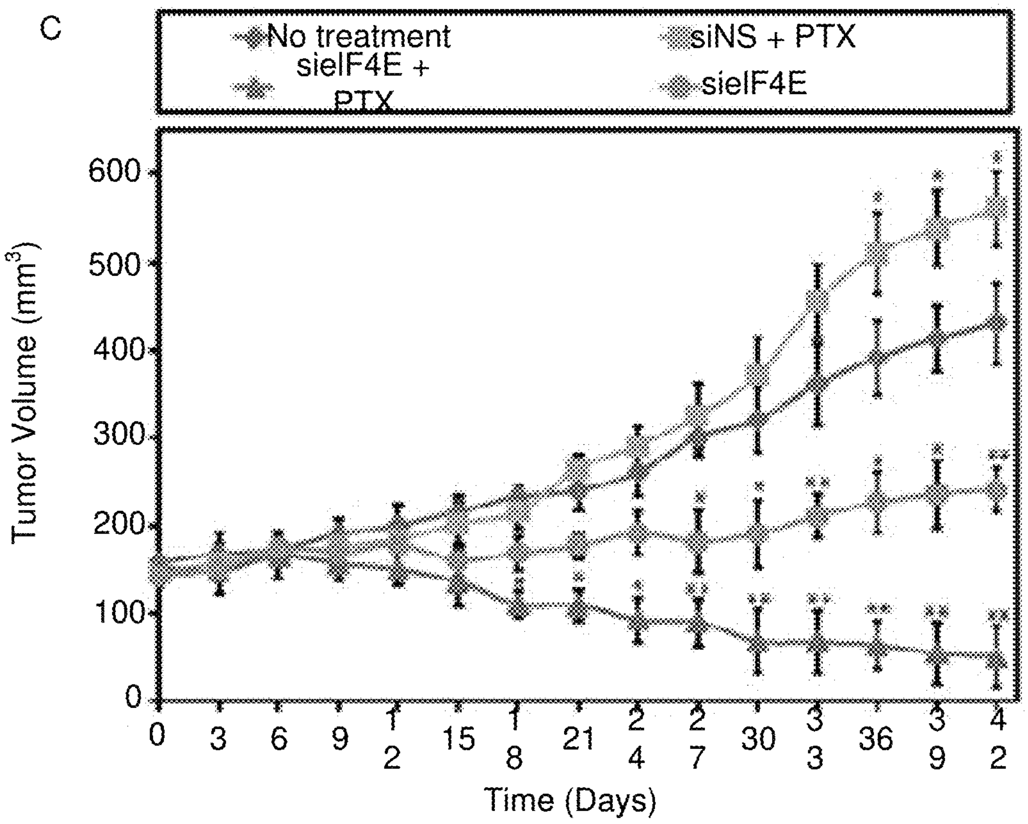
Figure 42D:
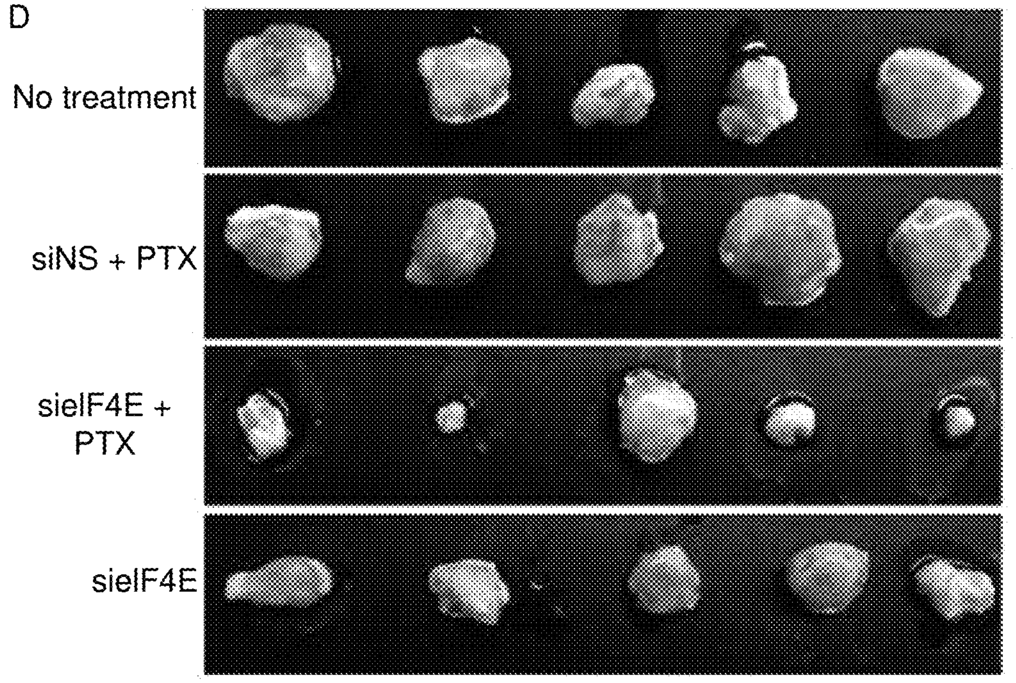
Figure 42E:
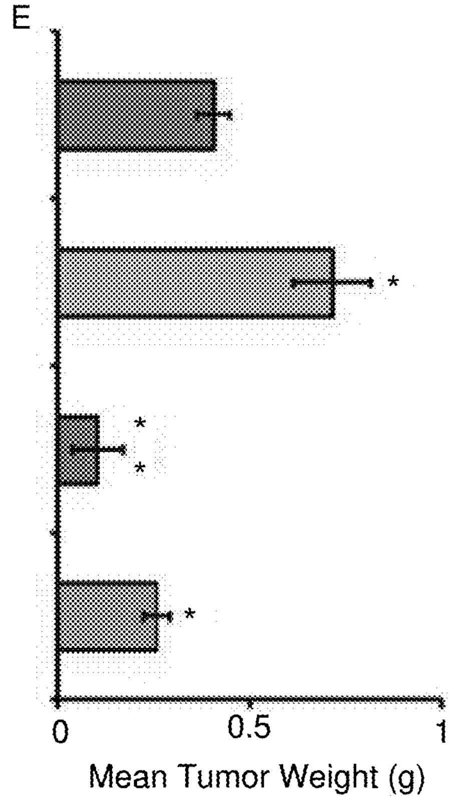
Figure 42F:
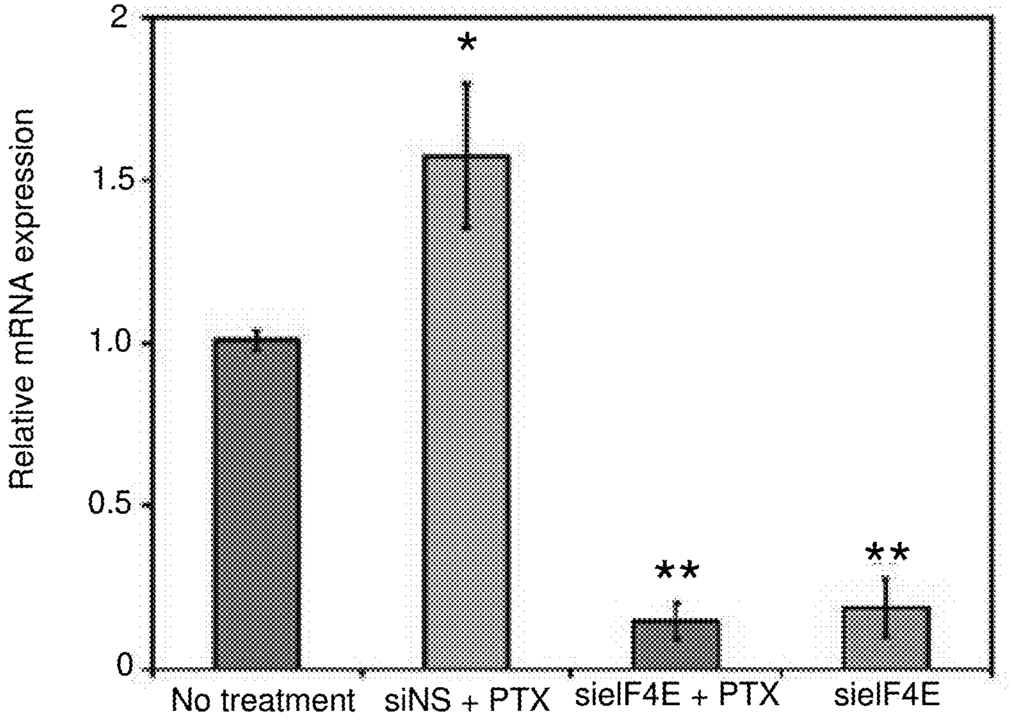
Figure 43A:
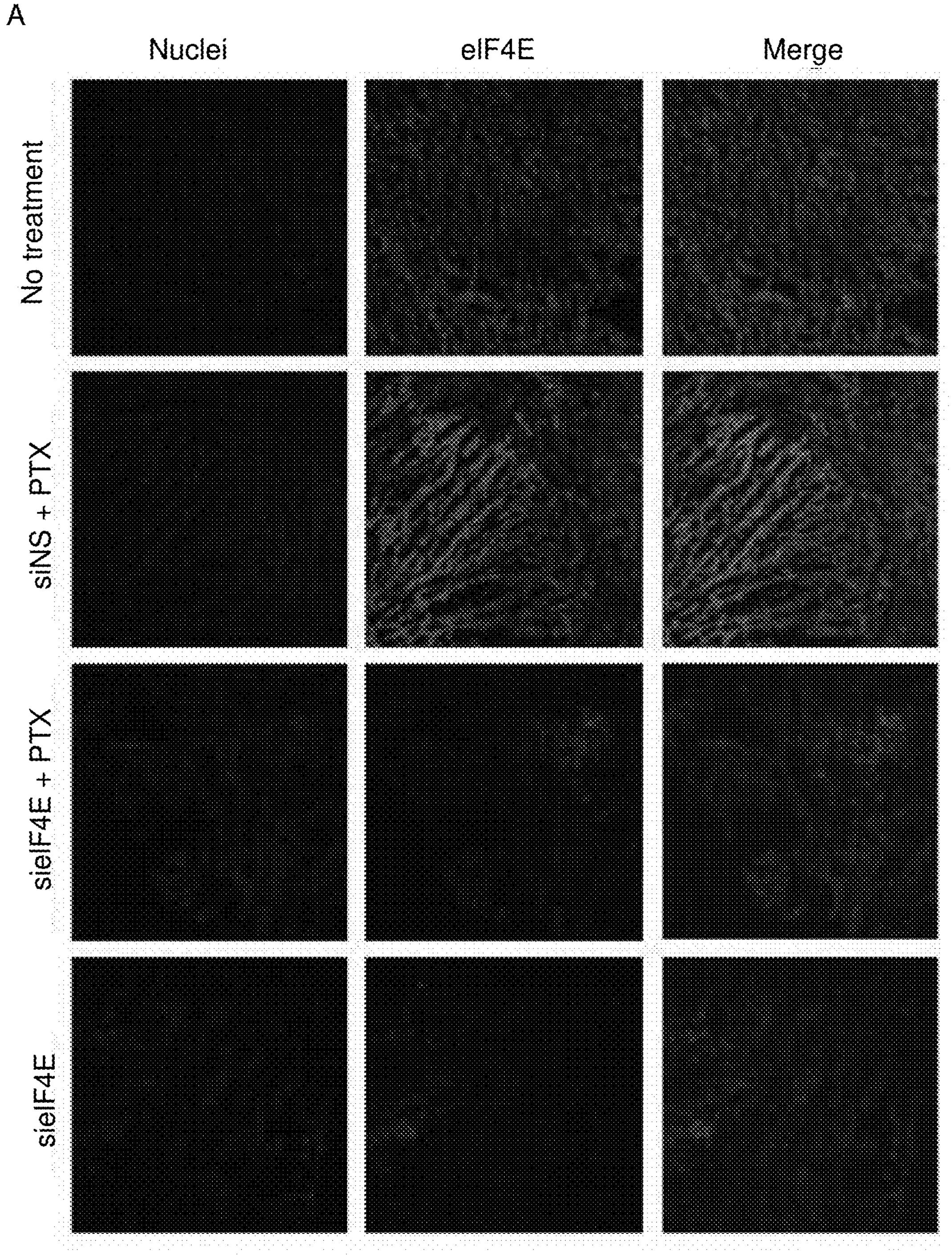
Figure 43B:
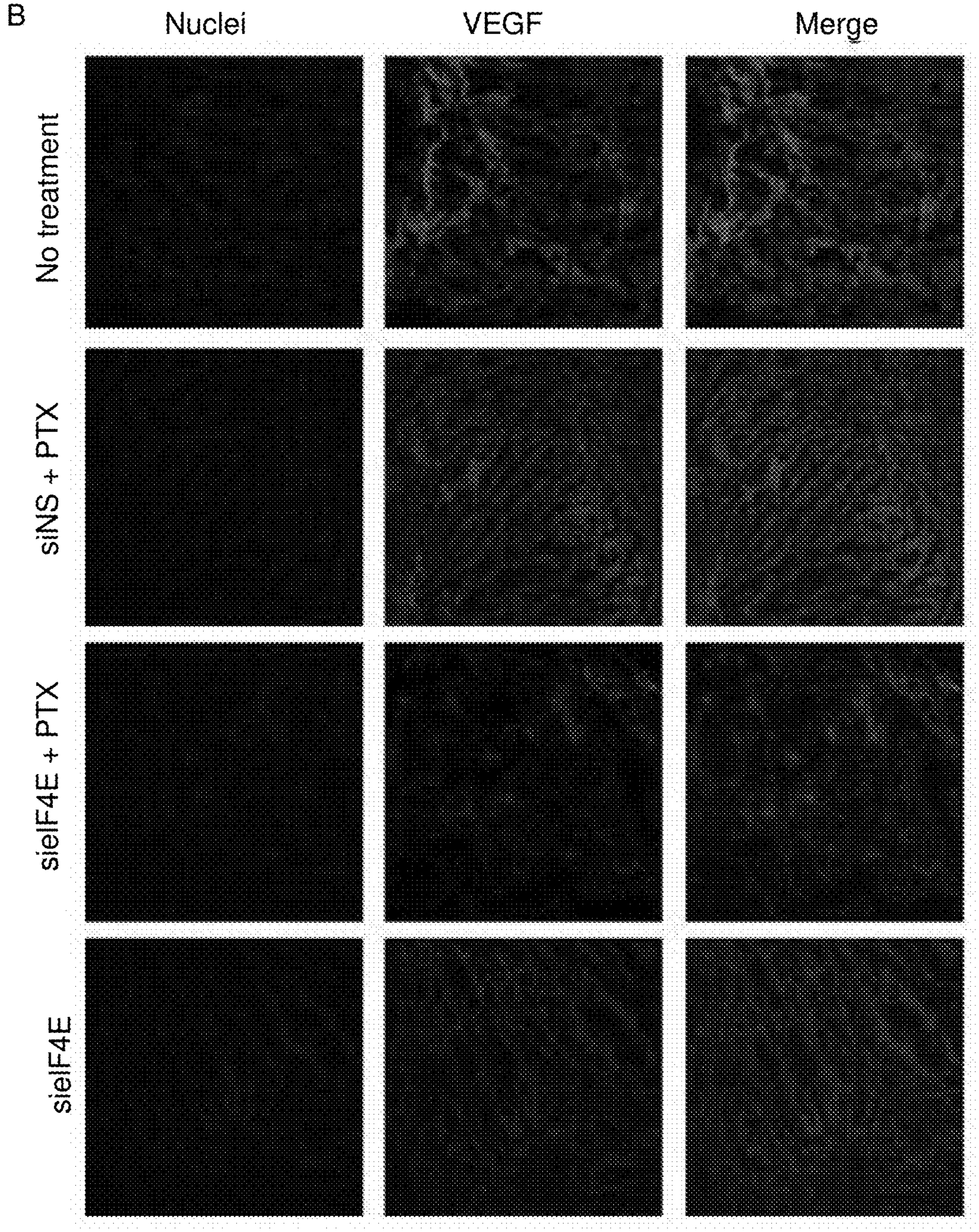
Figure 43C:
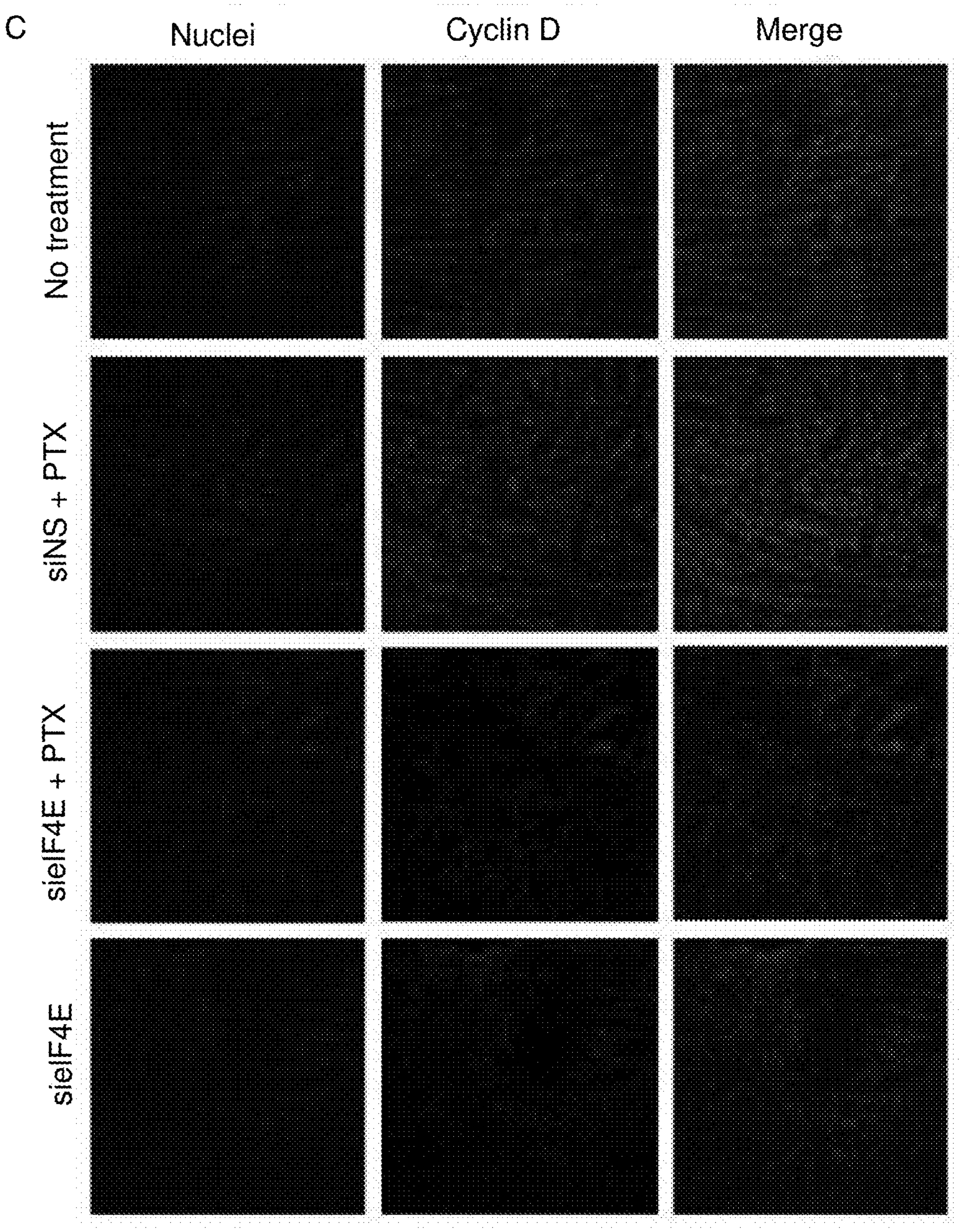
Figure 43D:
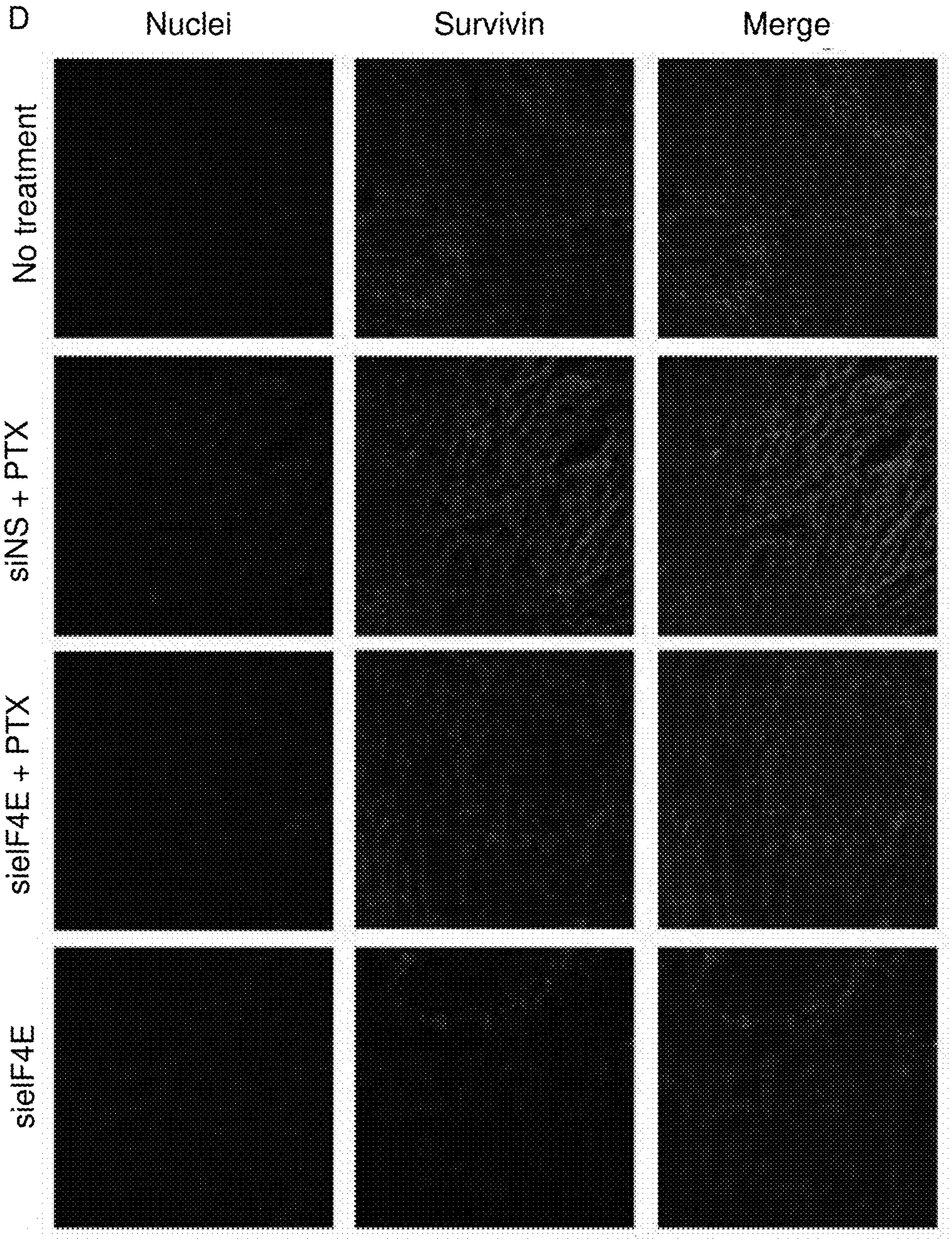

Combination of siRNA Targeting eIF4E and Paclitaxel Inhibits Primary Tumor Growth of Drug-Resistant MDA-MB-231 Cells The ability of the pH-cleavable RGD-PEG(HZ)-modified ECO/siRNA nanoparticles to re-sensitize PTX-resistant MDA-MB-231.DR tumors was evaluated in vivo. Female nude mice were engrafted with MDA-MB-231.DR cells in the mammary fat pad. When the tumors reached approximately 150 $mm^3$ in volume, the mice began receiving alternating treatments with siRNA nanoparticles (1.5 mg/kg siRNA dose) and PTX (5 mg/kg) every 6 days. Treatment with nanoparticles delivering non-specific siRNA (siNS) in combination with PTX had no inhibitory effect on tumor growth. In fact, after several weeks of treatment, the tumors of mice treated with siNS+PTX grew larger and more rapidly compared to the no treatment control, as determined by bioluminescent imaging and tumor volume measurements (FIG. 42A-C). After 42 days of treatment, the no treatment control tumors were an average of 430.1±37.8 $mm^3$ in volume and weighed 404.9±43.6 mg whereas siNS+PTX tumors were 560.3±46.2 $mm^3$ in volume and weighed 715.3±101.5 mg (FIG. 42C-E). Treatment of tumors with nanoparticles delivering anti-eIF4E siRNA alone significantly attenuated tumor growth to 240.4±35.7 $mm^3$ and 256.8±33.5 mg at day 42. This finding is supported by previously established data which demonstrates that silencing of eIF4E induces cell growth arrest. Likewise, Phase I clinical evaluation of the LY2275796 antisense oligonucleotide targeting eIF4E found only cytostasis, and not anti-tumor activity, was achieved upon eIF4E downregulation. A combination of sieIF4E and PTX significantly inhibited tumor growth and lead to tumor regression, 50.2±35.7 $mm^3$ and 103.2±67.4 mg. Significant knockdown of eIF4E mRNA was observed in both groups of mice treated with RGD-PEG(HZ)-ECO/sieIF4E nanoparticles (FIG. 42F).

Interestingly, from Immunofluorescent staining of primary tumor samples, siNS+PTX-treated tumors exhibited elevated levels of eIF4E, survivin, cyclin D1 and VEGF mRNA compared to the no treatment group, suggesting that treatment of drug-resistance cancers with PTX can further drive cancers to become more aggressive (FIG. 42C-E). This may occur through activation of the (PI3K)/akt signaling pathway implicated with both cell survival and drug resistance. As PTX relies upon apoptosis to induce tumor regression, elevated expression of survivin, an antiapoptotic factor, may contribute to the observed resistance to PTX therapy: experimental upregulation of survivin has been shown to confer taxol resistance. A downregulation of survivin exhibited in treatment groups receiving sieIF4E may help suppress tumor growth by increasing the susceptibility of cancer cells to apoptosis, particularly when coupled with PTX therapy. Tumor growth may also be suppressed through a reduction of angiogenesis, a consequence of VEGF downregulation also observed in groups receiving sieIF4E. These data in conjunction with the significant tumor regression observed for the sieIF4E+PTX treatment group indicates that knockdown of eIF4E re-sensitized the MDA-MB-231.DR cells to the cytotoxic effect of PTX.

Chemoresistance is a limitation in the treatment of patients with TNBC, where the lack of effective targeted therapies has left small-molecule based strategies as the sole option. Molecular targets exploited for targeted therapy against drug-resistant TNBCs could contribute significantly to an improved standard of care. While eIF4E has been explored as a therapeutic target in TNBCs before, the presented study represents the first evaluation of eIF4E in a drug-resistance TNBC cell line, therefore adding to the promising body of work surrounding eIF4E.

Long-Term Systemic Administration of RGD-PEG(HZ)-ECO/siRNA Nanoparticles Elicits No Chronic Immune Response or Organ Damage A concern of an RNAi-based approach to eIF4E therapy is the implication of non-specific silencing of eIF4E in healthy tissues. While the inclusion of the RGD-targeting peptide can enhance selective uptake within tumor cells, accumulation of the siRNA nanoparticles in non-specific tissues may lead to eIF4E downregulation outside of the tumor. In the current study, the expression of eIF4E following treatment with the siRNA nanoparticles was not evaluated in other vital organs, however, it has been reported elsewhere that no systemic toxicity was observed when 80% knockdown of eIF4E was achieved in essential organs using antisense technology. This may be explained by the phenomenon known as oncogene addition whereby cancer cells are overly dependent on the expression of a single gene for continued survival and proliferation. Under normal conditions, eIF4E is likely to be inactive due to being bound to the inhibitory 4E-BPs. A reduction in eIF4E levels would therefore have a minimal effect. Cancer cells characterized with elevated eIF4E expression, however, are more dependent on eIF4E expression than non-malignant cells or cancer cells with normal eIF4E expression.

Histopathological examination of liver and kidney tissues from mice receiving the long-term PTX and nanoparticle treatments was performed by hematoxylin and eosin (H&E) staining. No substantial toxicity or tissue damage to the liver or kidney was observed across all treatment groups. The absence of toxicity from treatment groups who received multiple administrations of PTX may be attributed to the relatively low and infrequent dosing: 5 mg/kg every 6 days compared to the conventional dose of 10 mg/kg. Treatment groups who received sieIF4E treatment also revealed no structural damage to the tissues, suggesting any systemic silencing of eIF4E harbors minimal toxicity.

As nude mice bear an inhibited immune system, such animals are not a suitable model to study potential immunogenic responses following systemic administration of ECO/siRNA nanoparticles. Accordingly, immunocompetent BALB/c mice were used to study the possible immune response following repeated tail-vein injections for RGD-PEG(HZ)-modified ECO/siRNA nanoparticles. Blood was collected at 2 h or 24 h following injections following 1, 3 and 5 injections spaced 5 days apart. Systemic treatment with unmodified ECO/siRNA nanoparticles elicited a robust activation of all cytokines measured at both the 2 h and 24 h timepoints due to the high surface charge of the nanoparticles. PEGylation in the form of RGD-PEG(HZ)-modification significantly attenuated the immune response for all tested cytokines. While cytokine levels increased at 2 h for IL-6, IL-12 and IFN-γ, the serum levels were reduced to basal levels at 24 h, indicative of a transient response. Importantly, serum levels were not compounded over the course of 5 repeated injections. These data, in conjunction with pathological examination of the liver and kidneys are indicative of the long-term safety of PEGylated ECO/siRNA nanoparticles.

From the above description of the invention, those skilled in the art will perceive improvements, changes and modifications. Such improvements, changes and modifications within the skill of the art are intended to be covered by the appended claims. All references, publications, and patents cited in the present application are herein incorporated by reference in their entirety.

Having described the invention, we claim:

1. A compound comprising formula (I):

(I)

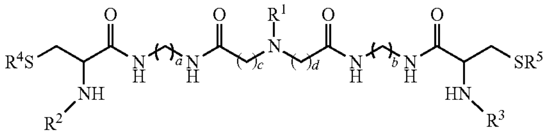

wherein $R^1$ is an alkylamino group or a group containing at least one aromatic group;

$R^2$ and $R^3$ are independently an aliphatic group or a hydrophobic group;

$R^4$ and $R^5$ are independently H, a substituted or unsubstituted alkyl group, an alkenyl group, an acyl group, an aromatic group, a substituted or unsubstituted polymer, a targeting group with an optional linker, or a detectable moiety;

a, b, c, and d are independently an integer from 1 to 10; and pharmaceutically acceptable salts thereof.

2. The compound of claim 1, wherein $R^1$ is:

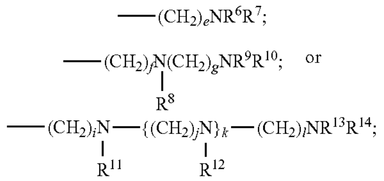

where $R^6$, $R^7$, $R^8$, $R^9$, $R^{10}$, $R^{11}$, $R^{12}$, $R^{13}$, and $R^{14}$ are independently hydrogen, an alkyl group, a hydrophobic group, or a nitrogen containing substituent; and e, f, g, i, j, k, and l, are an integer from 1 to 10.

3. The compound of claim 1, wherein $R^2$ and $R^3$ are independently a hydrophobic group derived from oleic acid or linoleic acid.

4. The compound of claim 3, wherein $R^2$ and $R^3$ are the same.

5. The compound of claim 1, wherein $R^4$ and $R^5$ are independently H, a substituted or unsubstituted polymer, a targeting group with an optional linker, or a detectable moiety.

6. The compound of claim 1, wherein a, b, c, and d are each 2.

7. The compound of claim 1, wherein $R^1$ is $CH_2CH_2NH_2$, $CH_2CH_2NHCH_2CH_2NHCH_2CH_2NH$, or $CH_2CH_2NHCH_2CH_2CH_2CH_2NHCH_2CH_2CH_2NH$.

8. The compound of claim 1, wherein the compound is (ECO)

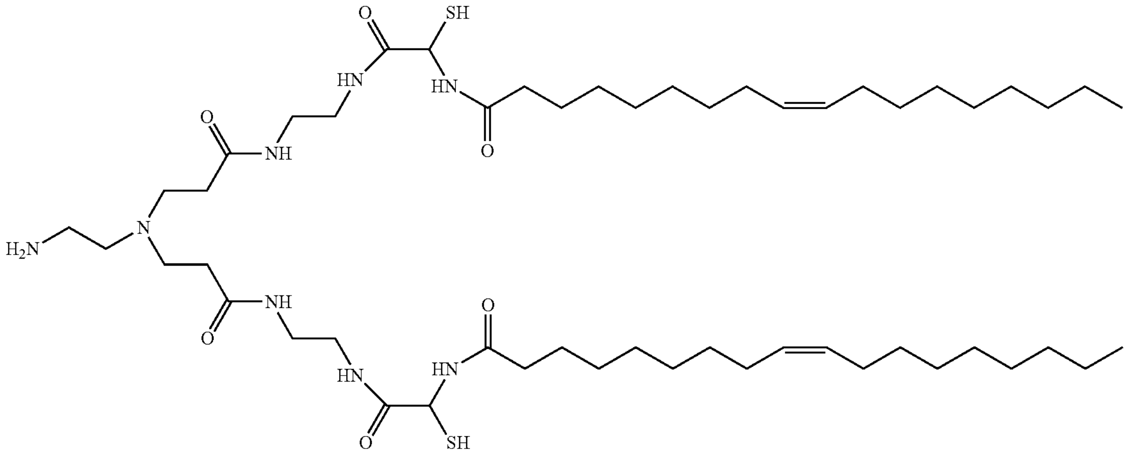

or

-continued (ECLn)

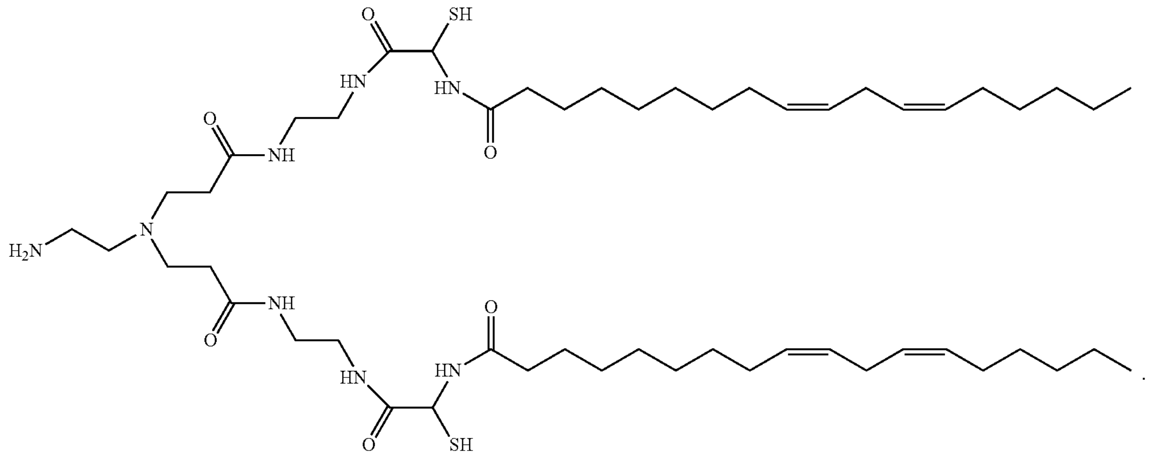

9. The compound of claim 1, wherein the linker is polyethylene glycol.

10. The compound of claim 1, wherein the targeting group is covalently attached to the compound by a linker.

11. The compound of claim 10, wherein the linker comprises a polyamino acid group, a polyalkylene group, or a polyethyelene glycol group.

12. The compound of claim 10, wherein the targeting group comprises a peptide, a protein, an antibody, or an antibody fragment.

13. The compound of claim 11, wherein the linker comprises an acid labile bond.

14. A nanosized complex comprising a nucleic acid and the compound of claim 1.

15. The nanosized complex of claim 14, wherein the nucleic acid comprises a natural or synthetic oligonucleotide, a DNA or fragment thereof, or an RNA or fragment thereof.

16. The nanosized complex of claim 14, wherein the nucleic acid comprises an siRNA or plasmid DNA.

17. The nanosized complex of claim 14, having an N/P ratio of at least about 6.

18. The nanosized complex of claim 14, wherein at least one of $R^4$ and $R^5$ is the targeting group with the optional linker.

19. The nanosized complex of claim 18, wherein the targeting group is covalently attached to the compound by the linker.

20. The nanosized complex of claim 19, wherein the linker comprises a polyamino acid group, a polyalkylene group, or a polyethyelene glycol group.

21. The nanosized complex of claim 18, wherein the targeting group comprises a peptide, a protein, an antibody, or an antibody fragment.

* * * * *

SEQUENCE LISTING

```
<160> NUMBER OF SEQ ID NOS: 8

<210> SEQ ID NO 1
<211> LENGTH: 23
<212> TYPE: DNA
<213> ORGANISM: Homo sapiens

<400> SEQUENCE: 1

cuuacgcuga guacuucgad tdt                                              23


<210> SEQ ID NO 2
<211> LENGTH: 23
<212> TYPE: DNA
<213> ORGANISM: Homo sapiens

<400> SEQUENCE: 2

ucgaaguacu cagcguaagd tdt                                              23
```

-continued

<210> SEQ ID NO 3
<211> LENGTH: 22
<212> TYPE: DNA
<213> ORGANISM: Homo sapiens

<400> SEQUENCE: 3
gcaagcugac ccugaaguuc au 22

<210> SEQ ID NO 4
<211> LENGTH: 22
<212> TYPE: DNA
<213> ORGANISM: Homo sapiens

<400> SEQUENCE: 4
gaacuucagg gucagcuugc cg 22

<210> SEQ ID NO 5
<211> LENGTH: 22
<212> TYPE: DNA
<213> ORGANISM: Homo sapiens

<400> SEQUENCE: 5
ctactaagag cggctccacc ac 22

<210> SEQ ID NO 6
<211> LENGTH: 22
<212> TYPE: DNA
<213> ORGANISM: Homo sapiens

<400> SEQUENCE: 6
tcgattgctt gacgcagtct cc 22

<210> SEQ ID NO 7
<211> LENGTH: 22
<212> TYPE: DNA
<213> ORGANISM: Homo sapiens

<400> SEQUENCE: 7
acggatttgg tcgtattggg cg 22

<210> SEQ ID NO 8
<211> LENGTH: 20
<212> TYPE: DNA
<213> ORGANISM: Homo sapiens

<400> SEQUENCE: 8
ctcctggaag atggtgatgg 20